(12) United States Patent
Chiang et al.

(10) Patent No.: US 12,102,479 B2
(45) Date of Patent: *Oct. 1, 2024

(54) ULTRASOUND 3D IMAGING SYSTEM

(71) Applicant: Teratech Corporation, Burlington, MA (US)

(72) Inventors: Alice M. Chiang, Wayland, MA (US); William M. Wong, Milton, MA (US); Steven R. Broadstone, Woburn, MA (US)

(73) Assignee: Teratech Corporation, Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/099,510

(22) Filed: Jan. 20, 2023

(65) Prior Publication Data
US 2023/0346344 A1  Nov. 2, 2023

Related U.S. Application Data

(63) Continuation of application No. 16/586,089, filed on Sep. 27, 2019, now Pat. No. 11,559,277, which is a
(Continued)

(51) Int. Cl.
*A61B 8/14* (2006.01)
*A61B 8/00* (2006.01)
(Continued)

(52) U.S. Cl.
CPC .............. *A61B 8/14* (2013.01); *A61B 8/145* (2013.01); *A61B 8/4444* (2013.01);
(Continued)

(58) Field of Classification Search
CPC ......... A61B 8/14; A61B 8/145; A61B 8/4444; A61B 8/4483; A61B 8/4488; A61B 8/466;
(Continued)

(56) References Cited

U.S. PATENT DOCUMENTS

| | | |
|---|---|---|
| 5,235,982 A | 8/1993 | O'Donnell |
| 5,295,485 A | 3/1994 | Shinomura et al. |
| | (Continued) | |

FOREIGN PATENT DOCUMENTS

| | | |
|---|---|---|
| EP | 1491913 A2 | 12/2004 |
| JP | 2004-008642 A | 1/2004 |
| | (Continued) | |

OTHER PUBLICATIONS

Leavens et al., Golay Pulse Encoding for Microbubble Contrast Imaging in Ultrasound, IEEE Transactions on Ultrasonics, Ferroelectrics, and Frequency Control. Oct. 2007;54(10):2082-2090.

(Continued)

*Primary Examiner* — Sanjay Cattungal
(74) *Attorney, Agent, or Firm* — McCarter & English, LLP

(57) ABSTRACT

The present invention related to an ultrasound imaging system win which the scan head includes a beamformer circuit that performs far field subarray beamforming or includes a sparse array selecting circuit that actuates selected elements. When using a hierarchical two-stage or three-stage beamforming system, three dimensional ultrasound images can be generated in real-time. The invention further relates to flexible printed circuit boards in the probe head. The invention furthermore related to the use of coded or spread spectrum signaling in ultrasound imagining systems. Matched filters based on pulse compression using Golay code pairs improve the signal-to-noise ratio thus enabling third harmonic imaging with suppressed sidelobes. The system is suitable for 3D full volume cardiac imaging.

34 Claims, 59 Drawing Sheets

Related U.S. Application Data continuation of application No. 13/899,320, filed on May 21, 2013, now Pat. No. 10,426,435, which is a continuation of application No. 13/498,043, filed as application No. PCT/US2010/050959 on Sep. 30, 2010, now abandoned, which is a continuation-in-part of application No. 12/570,856, filed on Sep. 30, 2009, now Pat. No. 10,080,544, which is a continuation-in-part of application No. PCT/US2009/056995, filed on Sep. 15, 2009, which is a continuation-in-part of application No. 12/286,555, filed on Sep. 30, 2008, now Pat. No. 8,551,000.

(60) Provisional application No. 61/192,063, filed on Sep. 15, 2008.

(51) Int. Cl.
  *A61B 8/08* (2006.01)
  *G01S 7/52* (2006.01)
  *G01S 15/89* (2006.01)
  *G10K 11/34* (2006.01)

(52) U.S. Cl.
  CPC .......... *A61B 8/4483* (2013.01); *A61B 8/4488* (2013.01); *A61B 8/466* (2013.01); *A61B 8/483* (2013.01); *A61B 8/488* (2013.01); *A61B 8/52* (2013.01); *A61B 8/54* (2013.01); *G01S 7/52079* (2013.01); *G01S 7/5208* (2013.01); *G01S 7/52082* (2013.01); *G01S 7/52085* (2013.01); *G01S 7/52095* (2013.01); *G01S 15/8925* (2013.01); *G01S 15/8927* (2013.01); *G01S 15/8961* (2013.01); *G10K 11/346* (2013.01); *A61B 8/08* (2013.01); *A61B 8/0883* (2013.01); *A61B 8/4411* (2013.01); *A61B 8/4472* (2013.01); *A61B 8/543* (2013.01); *A61B 8/565* (2013.01); *G01S 15/8913* (2013.01); *G01S 15/8959* (2013.01); *G01S 15/8993* (2013.01)

(58) Field of Classification Search
  CPC ........... A61B 8/483; A61B 8/488; A61B 8/52; A61B 8/54; A61B 8/08; A61B 8/0883; A61B 8/4411; A61B 8/4472; A61B 8/543; A61B 8/565; G01S 7/52079; G01S 7/5208; G01S 7/52082; G01S 7/52085; G01S 7/52095; G01S 15/8925; G01S 15/8927; G01S 15/8961; G01S 15/8913; G01S 15/8959; G01S 15/8993; G10K 11/346
  See application file for complete search history.

(56) References Cited

U.S. PATENT DOCUMENTS

| | | |
|---|---|---|
| 5,305,756 A | 4/1994 | Entrekin et al. |
| 5,435,313 A | 7/1995 | Noda et al. |
| 5,546,807 A | 8/1996 | Oxaal et al. |
| 5,590,658 A | 1/1997 | Chiang et al. |
| 5,608,690 A | 3/1997 | Hossack et al. |
| 5,622,177 A | 4/1997 | Breimesser et al. |
| 5,680,863 A | 10/1997 | Hossack et al. |
| 5,696,737 A | 12/1997 | Hossack et al. |
| 5,722,412 A * | 3/1998 | Pflugrath ............ G01S 15/8915 600/459 |
| 5,735,282 A | 4/1998 | Hossack |
| 5,740,128 A | 4/1998 | Hossack et al. |
| 5,817,024 A | 10/1998 | Ogle et al. |
| 5,832,923 A | 11/1998 | Engeler et al. |
| 5,840,032 A * | 11/1998 | Hatfield ............ G01S 7/52085 348/E13.064 |
| 5,893,363 A | 4/1999 | Little et al. |
| 5,911,692 A | 6/1999 | Hussain et al. |
| 5,938,611 A * | 8/1999 | Muzilla ............ G01S 15/8979 600/455 |
| 5,951,479 A | 9/1999 | Holm et al. |
| 5,964,708 A * | 10/1999 | Freeman ............ G01S 7/52028 600/447 |
| 5,997,479 A | 12/1999 | Savord et al. |
| 6,013,032 A * | 1/2000 | Savord ............ G01S 15/8927 600/443 |
| 6,039,690 A | 3/2000 | Holley et al. |
| 6,050,944 A | 4/2000 | Holley et al. |
| 6,086,537 A | 7/2000 | Urbano et al. |
| 6,089,096 A * | 7/2000 | Alexandru ........ G01S 15/8925 73/625 |
| 6,102,863 A | 8/2000 | Pflugrath et al. |
| 6,104,670 A | 8/2000 | Hossack et al. |
| 6,106,471 A | 8/2000 | Wiesauer et al. |
| 6,106,472 A | 8/2000 | Chiang et al. |
| 6,111,816 A | 8/2000 | Chiang et al. |
| 6,155,979 A | 12/2000 | Moser |
| 6,186,948 B1 | 2/2001 | Kamiyama et al. |
| 6,224,556 B1 * | 5/2001 | Schwartz ............ G01S 15/895 600/447 |
| 6,224,566 B1 | 5/2001 | Loeb |
| 6,245,017 B1 | 6/2001 | Hashimoto et al. |
| 6,279,399 B1 | 8/2001 | Holm |
| 6,292,433 B1 | 9/2001 | Gilbert et al. |
| 6,375,617 B1 | 4/2002 | Fraser |
| 6,419,633 B1 | 7/2002 | Robinson et al. |
| 6,468,216 B1 | 10/2002 | Powers et al. |
| 6,482,160 B1 * | 11/2002 | Stergiopoulos ..... G01S 7/52046 600/443 |
| 6,491,634 B1 | 12/2002 | Leavitt et al. |
| 6,497,663 B2 | 12/2002 | Fraser et al. |
| 6,537,220 B1 | 3/2003 | Friemel et al. |
| 6,552,964 B2 | 4/2003 | Chiang et al. |
| 6,558,325 B1 | 5/2003 | Pang et al. |
| 6,638,226 B2 | 10/2003 | He et al. |
| 6,645,150 B2 | 11/2003 | Angelsen et al. |
| 6,648,826 B2 | 11/2003 | Little et al. |
| 6,671,227 B2 | 12/2003 | Gilbert et al. |
| 6,679,847 B1 | 1/2004 | Robinson et al. |
| 6,705,995 B1 * | 3/2004 | Poland ............ G01S 7/52025 600/447 |
| 6,709,395 B2 | 3/2004 | Poland |
| 6,716,174 B1 * | 4/2004 | Li ............ G01S 15/8993 600/447 |
| 6,719,696 B2 | 4/2004 | Stergiopoulos et al. |
| 6,721,235 B2 * | 4/2004 | Chiang ............ H01Q 3/2682 367/138 |
| 6,730,033 B2 | 5/2004 | Yao et al. |
| 6,821,251 B2 | 11/2004 | Alexandru |
| 6,836,159 B2 | 12/2004 | Wodnicki |
| 6,852,081 B2 | 2/2005 | Sumanaweera et al. |
| 6,865,140 B2 | 3/2005 | Thomenius et al. |
| 6,867,720 B1 * | 3/2005 | Freeman ............ G01S 7/52028 341/172 |
| 6,869,401 B2 | 3/2005 | Gilbert et al. |
| 6,875,178 B2 | 4/2005 | Phelps et al. |
| 6,890,301 B2 | 5/2005 | Jago et al. |
| 6,891,311 B2 | 5/2005 | Phelps et al. |
| 6,967,975 B2 | 11/2005 | Van Stalen et al. |
| 6,974,417 B2 | 12/2005 | Lockwood et al. |
| 6,980,844 B2 | 12/2005 | Schoisswohl |
| 6,994,674 B2 | 2/2006 | Sheljaskow et al. |
| 7,037,263 B2 | 5/2006 | Sumanaweera et al. |
| 7,044,912 B2 | 5/2006 | Babu et al. |
| 7,079,132 B2 | 7/2006 | Sauer et al. |
| 7,115,093 B2 | 10/2006 | Halmann et al. |
| 7,131,947 B2 | 11/2006 | Demers |
| 7,141,020 B2 | 11/2006 | Poland et al. |
| 7,150,716 B2 | 12/2006 | Jones et al. |
| 7,169,108 B2 | 1/2007 | Little et al. |
| 7,217,243 B2 | 5/2007 | Takeuchi |
| 7,227,813 B2 | 6/2007 | Miller |
| 7,270,634 B2 | 9/2007 | Scampini et al. |
| 7,285,094 B2 | 10/2007 | Nohara et al. |

(56) References Cited

U.S. PATENT DOCUMENTS

| | | |
|---|---|---|
| 7,297,118 B2 | 11/2007 | Kristoffersen |
| 7,302,092 B1 | 11/2007 | Fenster et al. |
| 7,322,936 B2 | 1/2008 | Takeuchi |
| 7,331,234 B2 | 2/2008 | Tsujita et al. |
| 7,347,820 B2 | 3/2008 | Bonnefous |
| 7,448,998 B2 | 11/2008 | Robinson |
| 7,527,591 B2 | 5/2009 | Haugen et al. |
| 7,527,592 B2 | 5/2009 | Haugen et al. |
| 7,529,393 B2 | 5/2009 | Peszynski et al. |
| 7,563,228 B2 | 7/2009 | Ma et al. |
| 7,570,112 B2 | 8/2009 | Randall et al. |
| 7,714,855 B2 | 5/2010 | Brabec et al. |
| 7,724,928 B2 | 5/2010 | Glukhovsky et al. |
| 7,852,335 B2 | 12/2010 | Brabec et al. |
| 7,874,991 B2 | 1/2011 | Chiang et al. |
| 8,018,454 B2 | 9/2011 | Brabec et al. |
| 8,257,260 B2 * | 9/2012 | Savord ............... G01S 7/52017 600/443 |
| 8,551,000 B2 | 10/2013 | Chiang et al. |
| 10,080,544 B2 | 9/2018 | Chiang et al. |
| 2001/0044278 A1 | 11/2001 | Chiao et al. |
| 2002/0091317 A1 | 7/2002 | Chiao |
| 2002/0120193 A1 | 8/2002 | Chiang et al. |
| 2002/0183618 A1 * | 12/2002 | Hwang ............... G01S 7/52093 600/443 |
| 2003/0065262 A1 | 4/2003 | Stergiopoulos et al. |
| 2003/0067249 A1 * | 4/2003 | Lockwood ............ B06B 1/0622 310/324 |
| 2003/0097071 A1 | 5/2003 | Halmann et al. |
| 2003/0163046 A1 * | 8/2003 | Nohara ............... G01S 15/8927 600/443 |
| 2003/0216645 A1 | 11/2003 | Yao et al. |
| 2004/0000841 A1 | 1/2004 | Phelps et al. |
| 2004/0002435 A1 | 1/2004 | Petersen et al. |
| 2004/0181151 A1 | 9/2004 | Sumanaweera et al. |
| 2004/0267135 A1 | 12/2004 | Takeuchi |
| 2005/0043619 A1 | 2/2005 | Sumanaweera et al. |
| 2005/0057284 A1 | 3/2005 | Wodnicki |
| 2005/0090745 A1 * | 4/2005 | Steen ................... A61B 8/483 600/447 |
| 2005/0110793 A1 * | 5/2005 | Steen ................... G06T 15/005 345/536 |
| 2005/0113689 A1 | 5/2005 | Gritzky |
| 2005/0113698 A1 | 5/2005 | Kristoffersen et al. |
| 2005/0124884 A1 | 6/2005 | Bolorforosh et al. |
| 2005/0131295 A1 | 6/2005 | Li |
| 2005/0192499 A1 | 9/2005 | Lazenby et al. |
| 2005/0243812 A1 * | 11/2005 | Phelps ................. G01S 7/5208 370/360 |
| 2005/0253841 A1 | 11/2005 | Brabec et al. |
| 2005/0288588 A1 | 12/2005 | Weber et al. |
| 2006/0058667 A1 | 3/2006 | Lemmerhirt et al. |
| 2006/0064014 A1 | 3/2006 | Falco et al. |
| 2006/0071932 A1 | 4/2006 | Weese et al. |
| 2006/0074310 A1 | 4/2006 | Thiele |
| 2006/0241468 A1 | 10/2006 | Lu et al. |
| 2007/0088213 A1 | 4/2007 | Poland |
| 2007/0232910 A1 | 10/2007 | Hwang et al. |
| 2008/0009739 A1 * | 1/2008 | Chiang ................. G01S 7/5208 600/459 |
| 2008/0012852 A1 | 1/2008 | Brabec et al. |
| 2008/0018642 A1 | 1/2008 | Brabec et al. |
| 2008/0027320 A1 | 1/2008 | Bolorforosh et al. |
| 2008/0027323 A1 | 1/2008 | Freiburger |
| 2008/0106976 A1 | 5/2008 | Davidsen et al. |
| 2008/0242996 A1 | 10/2008 | Hall et al. |
| 2008/0262351 A1 * | 10/2008 | Scampini ............ A61B 8/4483 600/443 |
| 2008/0262357 A1 * | 10/2008 | Wodnicki ........... G01S 7/52017 600/459 |
| 2009/0003665 A1 | 1/2009 | Berg et al. |
| 2009/0005684 A1 | 1/2009 | Kristoffersen et al. |
| 2009/0024039 A1 | 1/2009 | Wang et al. |
| 2009/0030313 A1 * | 1/2009 | Prater ...................... A61B 8/54 600/443 |
| 2009/0149756 A1 | 6/2009 | Soler et al. |
| 2009/0156936 A1 | 6/2009 | Chiang et al. |
| 2009/0203996 A1 | 8/2009 | Thiele et al. |
| 2010/0160784 A1 * | 6/2010 | Poland ................. A61B 8/4444 600/459 |
| 2010/0160785 A1 * | 6/2010 | Poland ................. G01S 7/5208 600/459 |
| 2010/0160786 A1 * | 6/2010 | Nordgren ................. A61B 8/00 600/459 |
| 2010/0168576 A1 * | 7/2010 | Poland ................. G01S 7/5208 600/443 |
| 2010/0174194 A1 | 7/2010 | Chiang et al. |
| 2010/0262005 A1 | 10/2010 | Karasawa |
| 2010/0277305 A1 * | 11/2010 | Garner ................ A61B 8/4438 340/539.1 |
| 2012/0016243 A1 * | 1/2012 | Brown ................. G10K 11/346 600/472 |
| 2012/0179044 A1 | 7/2012 | Chiang et al. |

FOREIGN PATENT DOCUMENTS

| | | |
|---|---|---|
| JP | 2005-034634 A | 2/2005 |
| WO | 1998/34294 A2 | 8/1998 |
| WO | 2002/17298 A1 | 2/2002 |
| WO | 2006/038177 A1 | 4/2006 |
| WO | 2006/038178 A1 | 4/2006 |
| WO | 2006/038180 A1 | 4/2006 |
| WO | 2007/029199 A2 | 3/2007 |
| WO | 2007/099474 A1 | 9/2007 |
| WO | 2008/002464 A2 | 1/2008 |
| WO | 2008/038183 A1 | 4/2008 |

OTHER PUBLICATIONS

International Application No. PCT/US2009/056995, Search Report dated Dec. 2, 2009.

* cited by examiner

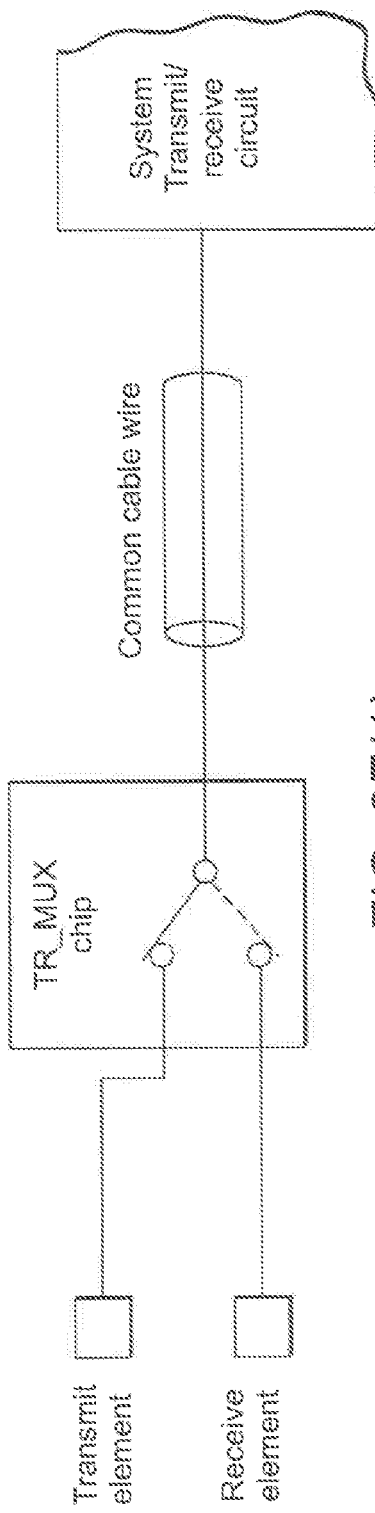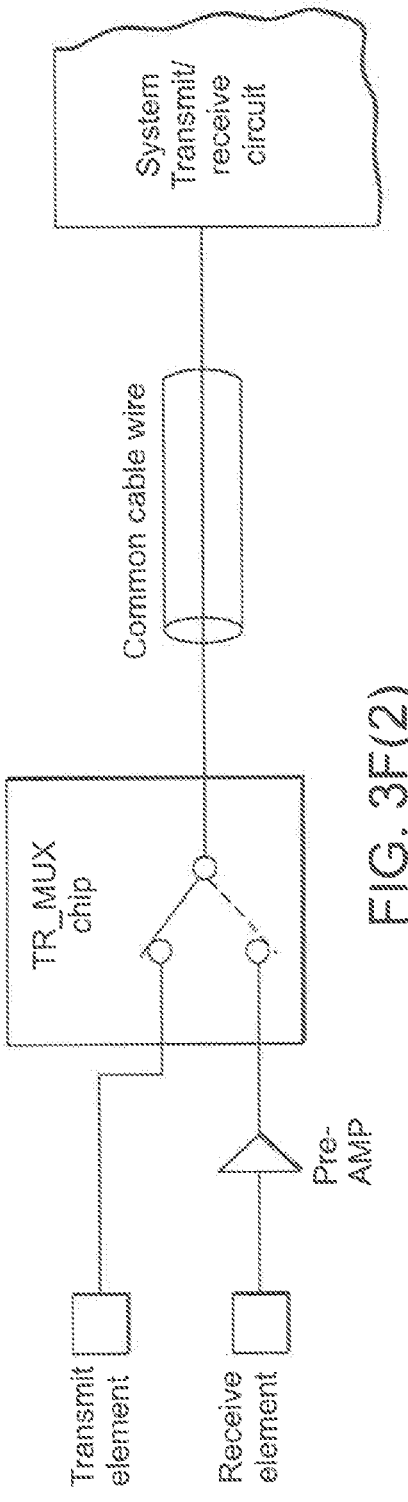
FIG. 3F(1)    FIG. 3F(2)

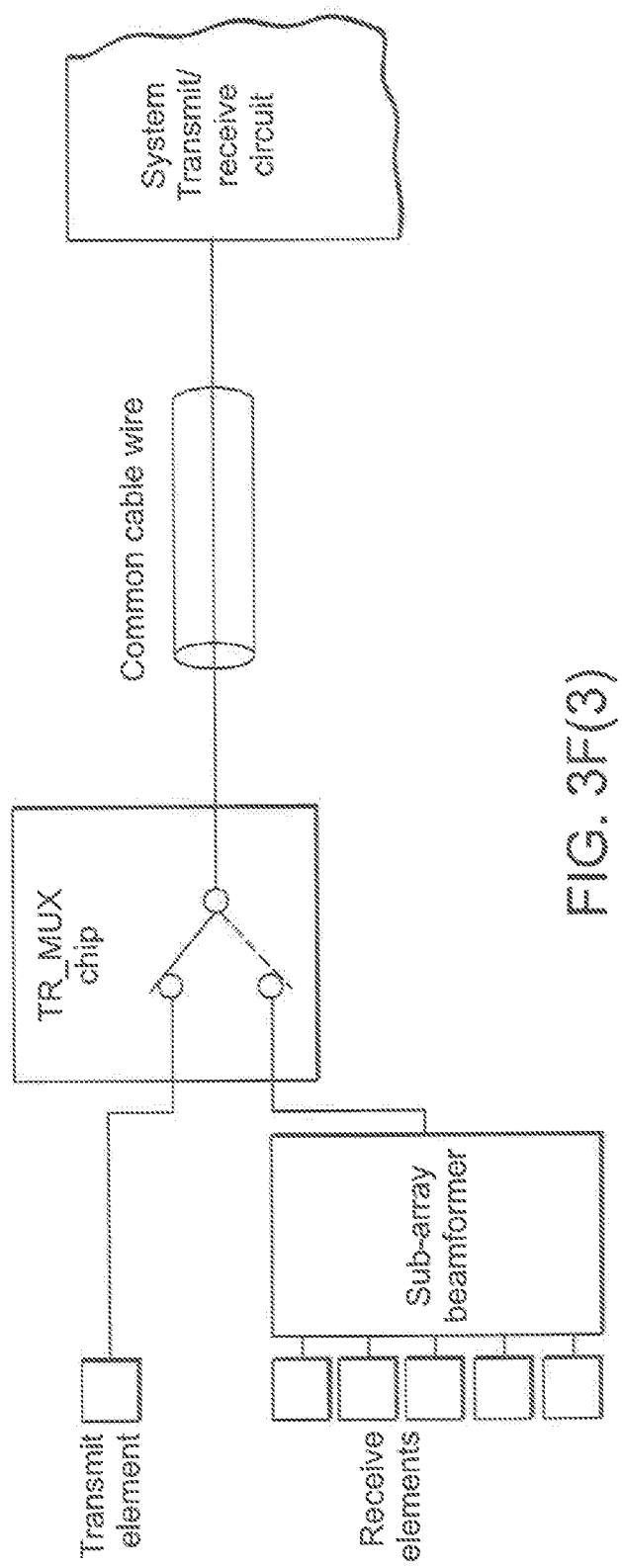
FIG. 3F(3)

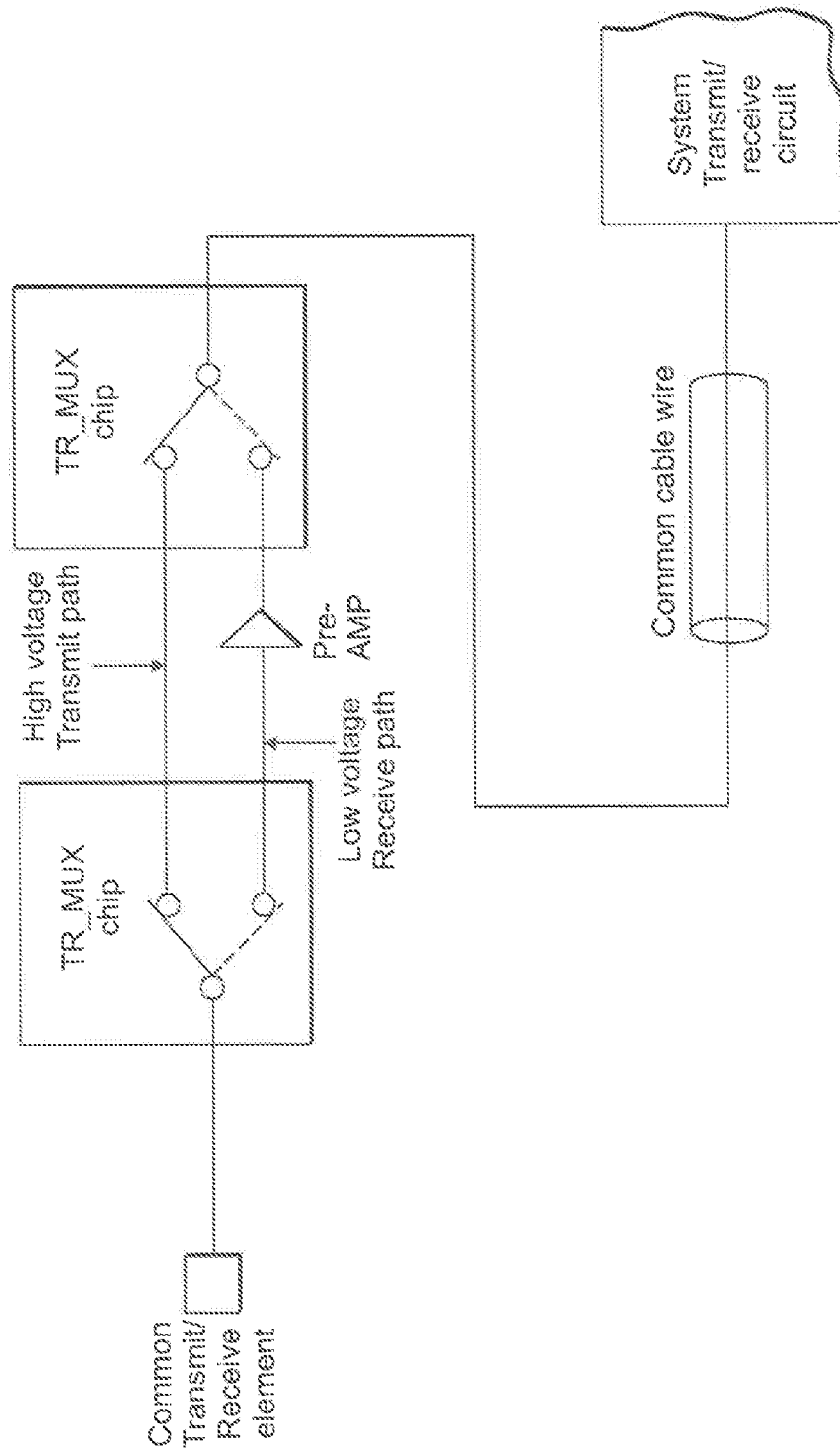
FIG. 3F(4)

FIG. 24A  Base Pulse=1
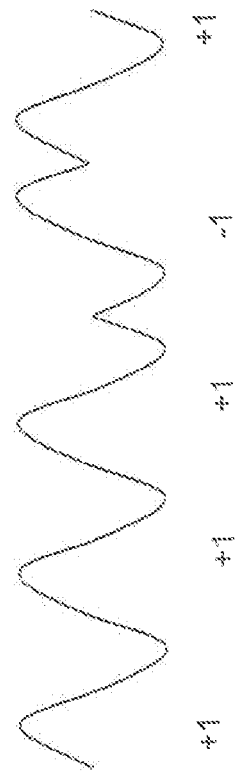
FIG. 24B  Base Pulse convolves with 5-chip Barker code
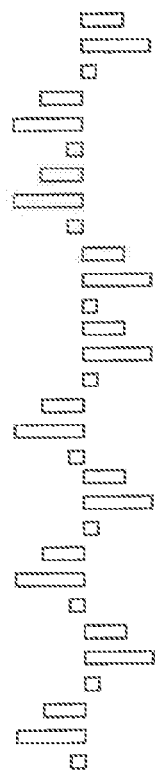
FIG. 24C  6 times Oversampled Transmitted waveform
Oversampled, Spread-Spectrum, Coded Transmit Waveform 3rd harmonic template of the first 10 bit Golay code when 12 over sampling for fundamental and 4 over sampling for 3rd harmonic -0.015392,-0.055771,0.038076,0.028839,0.046853,0.000259,-0.048214,0.009984,-0.013817,0.020245,-0.004117,-0.044618,
0.030906,0.022020,0.097704,-0.000757,-0.093799,-0.074193,-0.097050,0.142495,0.042181,0.099716,-0.067330,-0.053352,
0.022042,-0.002163,-0.010761,-0.100456,-0.129251,0.189798,0.088411,0.316329,0.213122,0.167861,-0.064531,-0.083720,
0.083276,-0.070915,-0.083733,0.127971,0.020194,-0.014892,0.009126,0.009148,0.000549,0.043114,0.022710,
0.027442,-0.041731,-0.006600,0.008397,-0.007585,0.000156,-0.061273,-0.004199,0.082287,-0.264062,-0.318569,0.481301,
0.108905,0.136914,-0.006247,-0.069733,-0.000691,-0.000256,0.002329,0.040045,0.054824,-0.078496,-0.054176,-0.229860,
0.152626,0.125593,-0.005188,0.001191,-0.000668,-0.054478,-0.065915,0.098890,0.033579,0.090236,-0.060225,-0.049422,
0.032035,0.000060,-0.032161,0.046696,0.054664,-0.083551,-0.014466,0.002113,-0.000411,-0.001898,0.011159,-0.000548,
-0.008619,-0.024835,-0.029946,0.045572,0.001212,-0.037556,0.023807,0.021806,-0.034198,0.000463,-0.031978,0.003634,
0.008351,-0.008773,0.001272,0.014401,-0.009098,-0.008516,0.021538,0.000056,-0.021791,0.011059,0.011931,-0.018845,

FIG. 29A

3rd harmonic template of the second 10 bit Golay code when 12 over sampling for fundamental and 4 over sampling for 3rd harmonic -0.008824,-0.027820,0.018987,0.014484,0.022302,0.000084,-0.022707,-0.009818,-0.013431,0.019342,0.008085,0.026831,
-0.017775,-0.014816,0.009059,0.000063,-0.009323,0.016580,0.019067,-0.029635,0.003022,0.047155,-0.030950,-0.025664,
0.016604,-0.000309,-0.015470,0.021140,0.030068,-0.042896,-0.024019,-0.083412,0.048176,0.058593,-0.344816,-0.001070,
0.349552,-0.102440,-0.094334,0.158912,-0.027233,-0.318685,0.205094,0.182789,-0.153202,0.001818,0.144812,-0.094923,
-0.105323,0.162640,0.053721,0.131823,-0.085303,-0.076091,0.284995,-0.002813,-0.104963,-0.139483,0.205625,
0.006984,-0.161162,0.106390,0.086570,0.091730,0.000959,-0.096384,-0.032134,-0.041338,0.061265,0.003944,-0.037130,
0.023690,0.021028,-0.028005,0.001484,0.020683,0.068112,0.084937,-0.127466,-0.017313,0.030932,-0.021416,-0.013993,
-0.116830,-0.000396,0.118731,-0.007615,-0.004045,0.008446,0.010447,0.048092,-0.031976,-0.026087,0.007071,-0.000045,
-0.006843,0.023280,0.028564,-0.042842,-0.011970,-0.023449,0.014763,0.014419,-0.073420,0.000537,0.070745,0.018747,
0.025976,-0.037990,0.003225,0.055044,-0.036558,-0.029401,-0.016851,-0.000558,0.019591,-0.003528,-0.003314,0.005625,

FIG. 29B

ULTRASOUND 3D IMAGING SYSTEM

CROSS REFERENCE TO RELATED APPLICATIONS

This application is a continuation of U.S. application Ser. No. 16/586,089 filed Sep. 27, 2019, which is a continuation of Ser. No. 13/899,320 filed on May 21, 2013, now U.S. Pat. No. 10,426,435, which is a continuation of application Ser. No. 13/498,043, filed Mar. 23, 2012, now abandoned, which is a National Stage entry under 35 U.S.C. § 371 of International Application No. PCT/US10/50959, filed Sep. 30, 2010, which is a continuation-in-part of U.S. application Ser. No. 12/570,856, filed Sep. 30, 2009, now U.S. Pat. No. 10,080,544, which is a continuation-in-part of International Application No. PCT/US09/56995, filed Sep. 15, 2009, which is a continuation-in-part of U.S. application Ser. No. 12/286,555 filed on Sep. 30, 2008, now U.S. Pat. No. 8,551,000, said PCT/US09/56995 also claiming priority to U.S. Application No. 61/192,063, filed on Sep. 15, 2008. The entire contents of the above applications are incorporated herein by reference.

BACKGROUND OF THE INVENTION

Medical ultrasound imaging has become an industry standard for many medical imaging applications. Techniques have been developed to provide three dimensional (3D) images of internal organs and processes using a two dimensional (2D) transducer array. These systems require thousands of beamforming channels. The power required to operate such systems has resulted in the use of an analog phase shift technique with a digital delay beamformer that results in a compromise of image quality.

There is a continuing need for further improvements in ultrasound imaging technologies enabling improved real-time three dimensional imaging capability. In addition, this improved capability should support continuous real-time display for a fourth dimensional 4D function.

SUMMARY OF THE INVENTION

The present invention relates to a system for ultrasound medical imaging that provides three dimensional (3D) imaging using a two dimensional (2D) array of transducer elements in a probe housing. Embodiments of the invention provide systems and methods for medical imaging having high resolution and numerous imaging modalities.

In a preferred embodiment, the probe housing contains a first beamforming circuit that transmits beamformed data to a second housing having a second beamforming circuit. The first beamforming circuit provides a far-field subarray beamforming operation. The resulting beamformed data is transmitted from the scan head to a second housing having the second beamforming circuit that provides near-field beam-steering and beamfocusing.

A preferred embodiment provides a scan head that can be connected to a conventional ultrasound system in which the scan head provides the inputs to the conventional beamforming processing function. The scan head beamformer can utilize a low power charge domain processor having at least 32 beamforming channels.

A preferred embodiment of the invention employs a sparse array where only a fraction of the transducer elements need to be activated. By selecting the four corner elements of the array to provide proper mean lobe bandwidth, minimizing average sidelobe energy and clutter, eliminating periodicity and maximizing peak to side lobe ratio, quality images are produced. To steer the beams across the volume or region of interest, different transducer elements must be actuated in proper sequence to maintain the peak to sidelobe ratio. The system processor can be programmed to provide the desired sequence for transducer actuation to direct the beam at different angles. Alternatively, a discrete controller can be used to control sparse array actuation. A preferred embodiment provides a scan head with integrated switching circuits for sequentially selecting sparse array actuation elements for sequential multiple beamforming. The scan head can be connected to a conventional ultrasound system in which the scan head provides the inputs to the conventional beamforming processing functions. In another embodiment, the transmit array elements and receive array elements can be operated independently with the transmit elements comprising a sparse array and the receive elements being a near fully populated array. In a preferred embodiment, the multiplexer and beamformer circuits can be integrated into an interface system, or alternatively, into a host processing system, leaving a 2D transducer array mounted in the probe housing.

The present invention utilizes nondestructive sensing at each stage of the delay elements in the beamformer. So with a 65 stage delay line, for example, there are 64 usable outputs with one at each stage. The time resolution can be in the range of $\frac{1}{8} \lambda$ to $\frac{1}{16} \lambda$.

Using high voltage multiplexers in the probe and the nondestructive sensing allows for time multiplexed sequential beamforming. It is now possible to sequentially change tap selection of each delay line to form multiple beams.

In addition to the three dimensional (3D) display capability, a fourth dimension or time resolved image display can be used to record and display a sequence of images recorded at 10 frames per second or higher, for example. This enables viewing of rapidly changing features such as blood or fluid flow; heart wall movement etc. at video frames rates of 30 frames per second.

Another preferred embodiment of the invention utilizes a three stage beamformer system in which a first stage performs a first beamforming operation on data received from a transducer array, which generates first beamformed data that is followed by a second stage that performs a second beamforming operation to provide second stage beamformed data that is then delivered to a third beamforming stage that performs a third beamforming operation.

The stages can be performed using charge domain processors. Data can also be converted from analog to digital form before the first stage, or the second stage, at the third stage or thereafter. One stage cart utilize parallel beamforming operations and a second stage provides serial beamforming.

A preferred embodiment of the invention performs real time imaging of large volumes such as the human heart without having to take gated images of different portions of the heart in sequence and then stitch the images together. This can be done using beamforming architectures in which multiple beams can be transmitted in a single pulse. This provides for the collection of adult heart images within a single cardiac cycle or heartbeat. This can be one with a narrowband phase shifting beamforming system and/or with a time domain beamforming system. By using parallel and serial beamforming components distributed in the transducer probe housing and the system main processor housing lightweight portable and cart mounted systems can be used for real time full volume cardiac imaging.

In medical ultrasound imaging, there is a need for harmonic imaging where the transmitted waveform is of one fundamental frequency $F_o$, and the received signal of interest is a higher harmonic, generally the $2^{nd}$ harmonic ($2 F_o$), or the third harmonic ($3 F_o$). The harmonic signal of interest is generated by the image targets in the body, and harmonics in the transmitted waveform are not of interest. Therefore it is important to suppress harmonic components from the transmitted waveform to obtain a clearer response.

The transmit circuit can generate either square waves or sinusoidal excitations. Square wave pulse generators are generally less costly than sinusoidal pulse generators, and the square wave pulsers are widely used in ultrasound imaging equipment. However a typical square wave itself contains high levels of the third harmonic. The present invention uses a modified square waveform which produces significantly reduced amount of the third harmonic, thus providing substantially improved harmonic imaging using the less expensive wave pulsers.

BRIEF DESCRIPTION OF THE DRAWINGS

FIGS. 3F(1)-3F(4) illustrate preferred embodiments of multiplexers used for switching in ultrasound transducer systems.

FIG. 4I illustrates an ultrasound system with a controller integrated into the transducer probe housing.

FIGS. 24A-24C illustrate a process for forming a transmission signal.

FIGS. 29A and 29B illustrate examples of the third harmonic template of first and second 10 bit Golay codes.

DETAILED DESCRIPTION OF THE INVENTION

The objective of the beamforming system is to focus signals received from an image point onto a transducer array. By inserting proper delays in a beamformer to wavefronts that are propagating in a particular direction, signals arriving from the direction of interest are added coherently, while those from other directions do not add coherently or cancel. For real-time three-dimensional applications, separate electronic circuitry is necessary for each transducer element. Using conventional implementations, the resulting electronics rapidly become both bulky and costly as the number of elements increases. Traditionally, the cost, size, complexity and power requirements of a high-resolution beamformer have been avoided by "work-around" system approaches. For real-time three-dimensional high-resolution ultrasound imaging applications, an electronically steerable two-dimensional beamforming processor based on a delay-and-sum computing algorithm is chosen.

Figure 1:
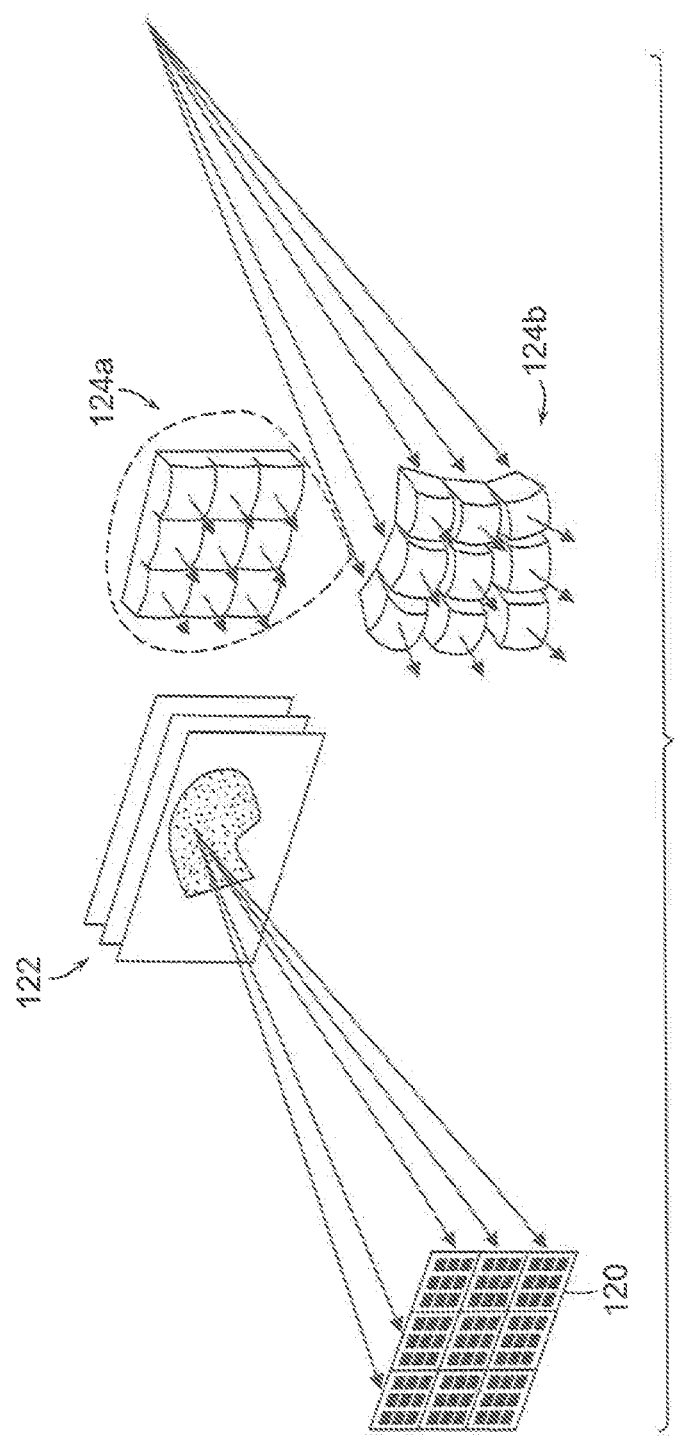
FIG. 1 illustrates the use of a two dimensional tiled array for ultrasound imaging in accordance with the invention.

The concept of an electronically-adjustable acoustic conformal lens is to divide the surface of a 2D transducer array into plane "tiles" of relatively small subarrays. As described in U.S. Pat. No. 6,292,433 the entire contents of which incorporated herein by reference, and illustrated in FIG. 1 the tiles/subarrays 120 are made small enough so that when an object is placed within the field-of-view of the imaging system, the incident radiation 122 from the object toward each "tile" can be treated using a far-field approximation. Additional delay elements are incorporated as second-stage processing to allow all subarrays to be coherently summed (i.e., global near-field beamforming can be achieved by simply delaying and then summing the outputs from all subarrays.) The delay-and-sum beamformer allows each subarray to "look" for signals radiating from a particular direction. By adjusting the delays associated with each element of the array, the array's look direction can be electronically steered toward the source of radiation. Thus instead of looking in one direction as seen at 124a, the direction of tiles 120 can be steered in different direction 124b. The delay line requirement for each element in the sub-array can be less than a hundred stages. Only long delays for global summing are needed for the final near field focusing.

Figure 2:
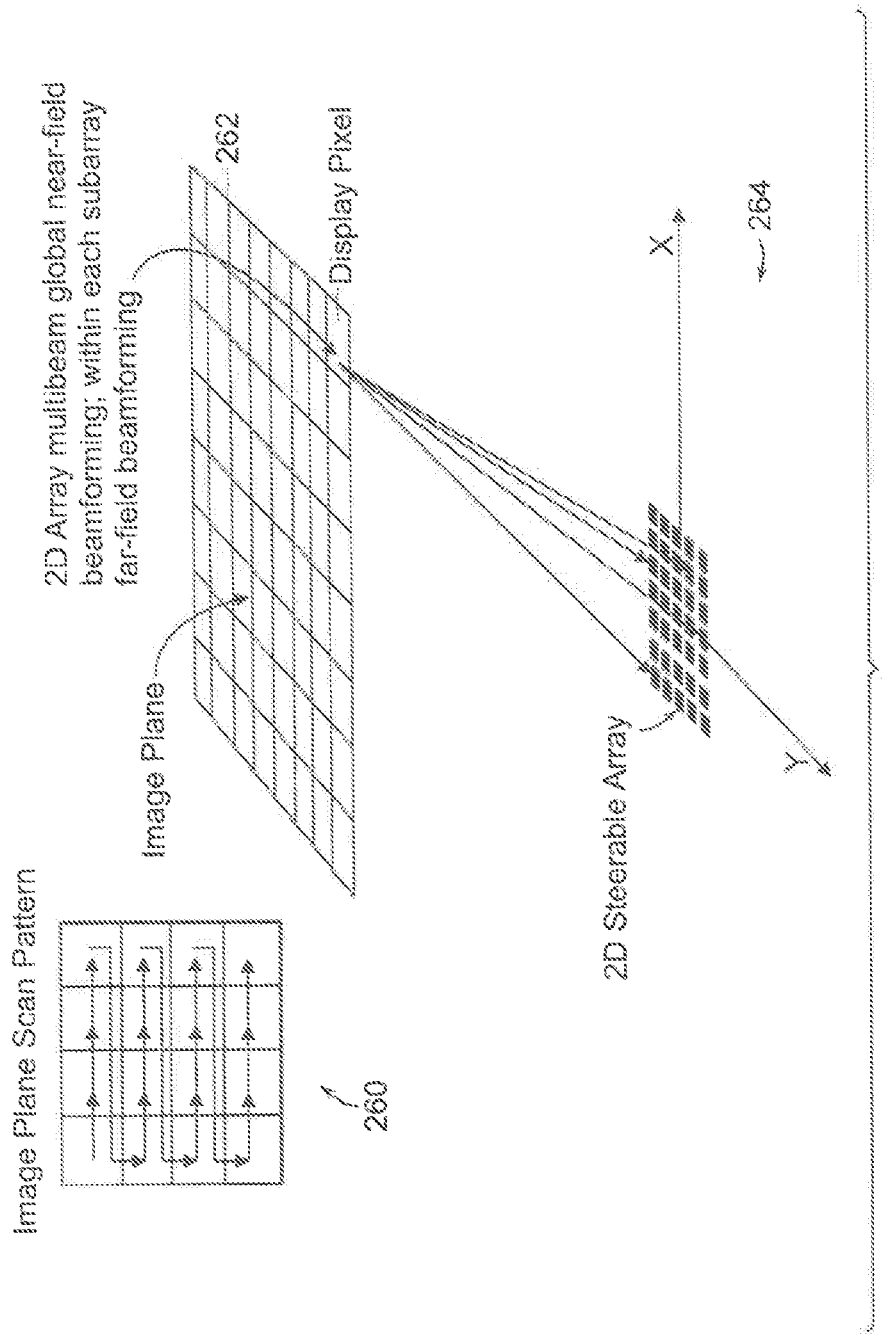
FIG. 2 illustrates a steerable two dimensional array in accordance with the invention.

To scan an image plane using a steerable beamformer system a process such as that shown in FIG. 2 can be used. A raster scan 260 can be used to scan an image plane 262 using a 2D steerable transducer array 264.

Figure 3A:
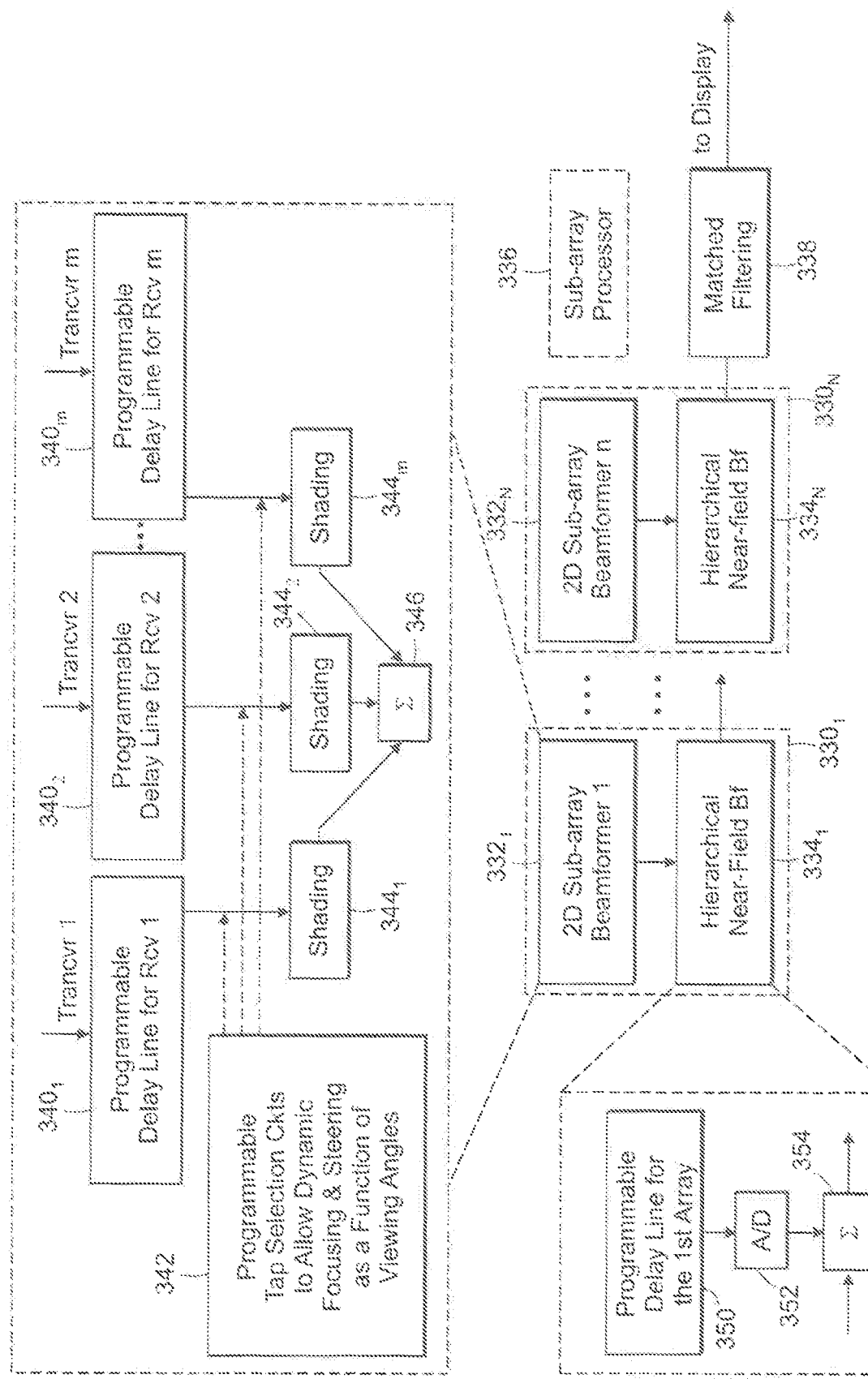
FIG. 3A illustrates the use of a first beamformer device for far field beamsteering and focusing and a second time delay beamformer for near field beamforming.

A detailed diagram of an electronically-controlled beamforming system in accordance with the invention is shown in FIG. 3A. This system consists of a bank of parallel time-delay beamforming processors 330, -330N. Each processor 330 consists of two components: a 2D sub-array beamformer 332 for far-field beamsteering/focusing and an additional time delay processor 334 to allow hierarchical near-field beamforming of outputs from each corresponding subarray. The sub-arrays 332 include m-programmable delay lines 340 with tap selectors 342, multiplexers 344 and summed 346 output. As can be seen in FIG. 3A, for a system with n-sub-arrays, n-parallel programmable $2^{nd}$-stage near field time delays are needed for individual delay adjustment which are converted with A/D converter 352 to allow all n-parallel outputs be summed 354 coherently, in turn, this summed output is filtered 338 and provides the 3D images of the targeted object. A processor 336 controls sub-array operation.

Figure 3B:
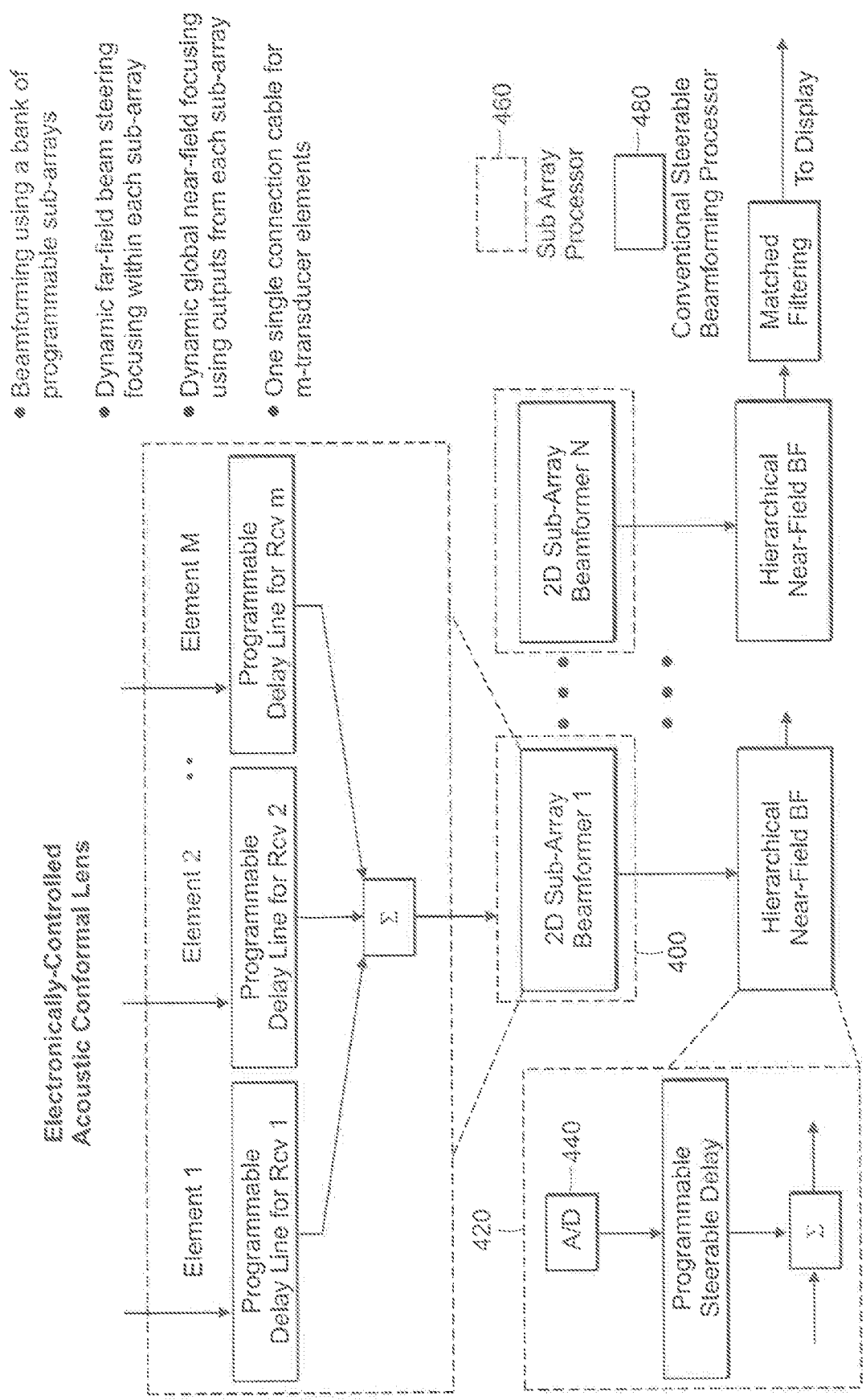
FIG. 3B illustrates a first analog subarray beamformer forwarding data to a digital beamformer.

Use of the scan head with a second stage digital beamformer is shown in FIG. 3B. In this embodiment, a plurality of N sub-array beamformers 400, which can be near-field beamformers in a preferred embodiment, each receive signals from m transducer elements that have separate delay lines whose outputs are summed and provided to beamformers 420 so that this beamformer can be a conventional system with conventional processor 480. A separate sub-array processor 460 controls beamformers 400.

Without using this hierarchical subarray far-field and then near-field beamforming approach, for an 80×80 element 2D array, a cable consisting of six thousand and four hundred wires is needed to connect the transducer array to a conventional beamforming system. As shown in FIG. 3A, the number of inputs to each subarray processor equals the total number of delay elements in the subarray, each sub-array only has a single output. The number of inputs to the subarray bank equals the number of 2D array elements, and the number of outputs from the subarray bank equals to the total transducer array element number divided by the sub-array element number, i.e., the number of outputs from the subarray bank reference to the number of inputs is reduced by a factor equal to the size of the subarray. For example, if one selects to use a 5×5 subarray to implement this hierarchical beamforming concept, after the first stage subarray beamforming, the total number of wires needed to connect to the $2^{nd}$ stage near-field beamforming is reduced by a factor of 25. More specifically, as mentioned above, without using this 2D, subarray beamforming, 6400 wires are needed to connect an 80×80 element 2D transducer array to a conventional backend beamforming system. Using a 5×5 subarray processing bank first, the number of wires required to connect to the backend beamforming system is reduced to 256. Based on the current invention, a bank of 256 5×5 element subarrays Beamformer can be integrated with a 80×80 element 2D array in the scan head, so a cable consisting of 256 wires is adequate to connect the integrated scan head with the back-end near-field beamforming system. It is important to note that 5×5 subarray far-field beamforming processors can be easily integrated in a small size silicon (Si) integrated circuit, eight of such 5×5 subarray beamformers can be integrated on one chip. In this embodiment, only 32 chips or less are integrated into the scan head, thereby reducing the cable size from 6,400 wires down to 256 wires.

The beamformer processing system is a time domain processor that can simultaneously process the returns of a large 2D array providing a low-power, highly integrated beamformer system capable of real time processing of the entire array in a portable system. While a system with 192 parallel received channels supports a matrix 2D array probe for a real-time 3D/4D imaging application, the hierarchical multi-stage beamforming can be used with a low-power compact ultrasound system.

FIG. 3B demonstrates the hierarchical beamforming architecture in which the beamforming of a group of neighboring receive elements is implemented in two stages, i.e., instead of a single long delay for each of the receive elements, a common long delay is shared by all elements within the group, but each has its own shorter, programmable delay in front of the long delay. Within each group, the outputs from each of the short delays are summed together then applied to the common long delay. A small group of neighboring receiving elements having this common long delay characteristic is defined as a "subarray" of the transducer array. For example, for application using a 2D matrix array for real-time 3D imaging, the subarray can be a small array with 4×4, or 5×5 adjacent elements. The first stage programmable delays of each element within this subarray are integrated inside the transducer probe; the summed output from each subarray is then connected to the backend processor. So, for a 64×48 element 2D array (3072 or more transducer elements), if a 4×4 subarray is used for the first stage beamforming, only 192 I/O cable elements are needed to connect the front-probe to the backend processors.

In a preferred embodiment, the hierarchical beamforming can also be applied to a one dimensional (1D) array for the real-time 2D imaging application. For example, for a 128-element 1D array, a group of 8 adjacent elements can be grouped together as a subarray. Within each subarray, each of the 8 elements has its own short programmable delay and then the outputs of the eight delays are summed together and then applied to a common long delay. It is important to note that two different methods that can be used for this two-stage implementation. In the first implementation, all the beamforming circuits including both the short and long delays are placed in the back-end processor, so for a 128 element 1D array, 128 connection cables are used as I/O cables between the transducer probe and the backend processor. An alternative implementation is to integrate all the subarray processors within the transducer probe, i.e., for a 128-element array, all 16 subarray processors each with 8 programmable delays are integrated within the transducer probe, so only 16 cable elements are needed to connect the front-end integrated probe with the back-end processors. Within the back-end, only 16 long delay beamforming circuits are needed to complete the beamforming function. Similarly, for a 64-element array with integrated eight 8-element subarray processors in the probe, the back-end processor can be simplified to only 8 beamforming circuits, only 8 cable elements are needed to connect the front-end integrated probe with the back-end processor. Furthermore, low-power transmit circuitry and A/D converters can be integrated into the front-end probe, so a wireless communication link can be used to connect the front-end probe and the back-end processor. A wireless USB connection or a wireless FireWire connection can be used.

Figure 3C:
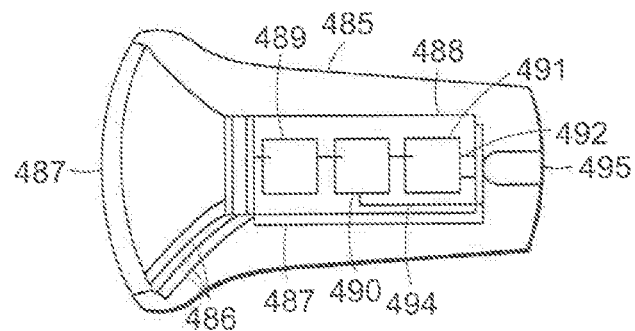
FIG. 3C illustrates a scanhead for a two dimensional transducer probe.

The construction of a 64×48 element 2D transducer probe 485 with integrated 4×4 sub-array processors is illustrated in FIG. 3C. The 64×48 element 2D array 487 can include stacking 48 rows of 1D arrays each with 64 elements. Connections to the elements of each 64 element 1D transducer array are through a flex cable, so the transducer head assembly can include the 2D transducer array and 48 flex cables 486. As shown in FIG. 3C, each sub-array can include 4×4 elements (or other rectangular or 2D geometry preferably having at least 16 elements and up to 256 elements per subarray), the 48 flex cables are grouped into 12 groups, with each adjacent four flex cables connected to a printed circuit board, i.e., flex cables corresponding to the row 1 and row 4 1D transducer array are connected to the first printed circuit board 488, the row 5 to row 8 flex cables are connected to the second printed circuit board 487 and so forth, until the row 45 to row 48 flex cables are connected to the twelfth printed circuit board. One end of each flex cable is connected to the transducer elements and the other end of the flex cable is connected to a 64-element flex connector mounted on the printed circuit board. Within each printed circuit board, there are a 16 4×4 element subarray processors 489 and a high voltage multiplexor chip 491. The subarray processor consists of 16 parallel programmable delay lines each with a low-noise pre-amplifier at its input and a separated programmable multiplier as apodizer and the outputs of the 16 multipliers are summed together to form a single outputs. Within each board, there is also a high-voltage multiplex chip, so to allow the 4×64 element transducer either operated in transmit or receive mode. A memory chip 490 is also mounted on each printed circuit board to store the programming delay for each of the delay lines. There are also power supply cables and digital inputs 492 connected through interface 495 to each printed circuit boards.

As can be seen in FIG. 3C, the beamforming processor on the printer circuit board has to provide the subarray beamforming function for a total of 64×4 receive elements which are divided into 16 subarrays with each subarray consisting of 4×4 elements. 16 subarray processors each can perform the beamforming function, i.e., time-delay-and-sum function, for 16 receives are incorporated on the printer circuit board. A photomicrograph of a 16 channel subarray beamformer chip is shown in FIG. 3E, for each transmit pulse, the chip is capable of forming 4 sequential beams for 16 receivers. The chip is based on a 0.35 μm double-poly, four-metal process. The size of the illustrated chip is 1.2 mm×0.6 mm. Thus, 8 such 4×4 subarray processors can be integrated on one chip with a chip size about 1.2 mm by 5 mm, so the circuit board only requires two such subarray beamforming chips, each including 8 of the 4×4 subarray processors.

In this chip, there are 16 tapped delay lines, each receiving returns from its corresponding receive element. During the receive mode after a transmission pulse, 4 sequential beams which are summed outputs from the 16 tapped delay lines are formed at every sampling clock. The tap output of each delay line is controlled by a 4-beam time-multiplex buffer memory. With each new digital update, a corresponding non-destructively sensed delayed sample is clocked out of the tapped delay line. With the four digital updates sequentially applied to the buffer memory, four delayed samples for each of the four beams are then sequentially clocked out.

The initial tap positions of each delay line are pre-loaded in memory before the scanning starts. During receive mode, at every sampling clock, returned echoes are sampled and clocked into its corresponding delay line. A multiplier is incorporated at the output of each tapped delay line to provide the beamshaping, apodization function. For example, if the center frequency of the transducer is 2 Mhz, the tapped delay line samples the returned echo at a 8 Mhz rate. The tap outputs are sequentially non-destructively sensed at a 32 Mhz rate to generate the 4 beams. That is, after a returned echo loaded into a delay line, 32 ns later the tap output of the delay sample of this delay line for the $1^{st}$ beam is clocked out and applied to the multiplier, another 32 ns later, the relayed tap output for the $2^{nd}$ beam is clocked out to the multiplier, the procedure follows, until 128 ns later the tap out for the $4^{th}$ beam is clocked out. The 16 multiplier outputs are summed together to form a single beam at 32 Mhz rate. It is important to note that for dynamic focusing, each beam needs two digital update bits; one for tap update and one for interpolation. In this chip, each channel has an analog input and a digital input; the two update bits are sequentially loaded into the chip. To support the 4-beam sequential outputs, the two-digital update bits of each beam are dynamically loaded into the chip at a 64 Mhz rate, thereby allowing continuous subarray beamforming function at a 8 Mhz analog input sampling rate. If the range depth is 1.5 cm, for a 2 Mhz probe oversampled by 4, the total received beamforming includes 2000 points. In this embodiment, the memory size on the circuit board shown in FIG. 3C is 64×4×4×2×2000=4 Mbits or more. Furthermore, a compression method can be used to reduce the memory size.

Typical ultrasound transducers use the same element for transmit and receive. The high voltage transmit pulse is sent to a particular element, and the echo from the same element travels back to the system via the same cable wire.

In some applications, it is desirable, or necessary to use separate elements for transmit and receive. One such application is the use of different transducer materials for transmit and receive, so that the transmitter and receiver elements can be made with different frequency responses that is a first frequency response and a second frequency responses different, from the first frequency response. This is particularly useful for harmonic imaging where the receiver center frequency is double or triple that of the transmitter center frequency. The transmit multiplexer (TR_MUX) integrated circuit chip allows one single cable wire to connect to the transmit element and the receive element by providing a fast high voltage switch that connects the cable wire to the transmit element during the transmit period, then to the receive element in the receive period as shown in FIG. 3F(1). Off-the-shelf high voltage multiplexer chips are not suitable for this application, as their intended use is to multiplex among elements for aperture selection, a slow process that happens at ultrasound scan line boundaries. In order to support switching between transmit period and receive period, the switching time needs to be on the order of less than a wave period to a few of wave periods, otherwise there will be a large dead time near the surface of the transducer that cannot be imaged. For example, a switch turn on/off time of 1 micro-second can switch from transmit to receive in one wave period at a 1 MHz transmit frequency, or two wave periods when the transmit frequency goes up to 2 MHz. It can be advantageous to amplify the received signals as shown in FIG. 3F(2).

Another application that requires a fast in-the-probe transmit/receive switch is a 2D array probe where the receive elements are first formed into sub-arrays to reduce the number of cable wires for receiving as shown in FIG. 3F (3). The sub-array beamforming circuit is usually a low voltage device, so it is necessary to isolate the sub-array from the cable wire during the high voltage transmit period.

Yet another application uses two levels of the TR_MUX chips to allow low voltage amplification circuits be used on a shared transmit/receive element as shown in FIG. 3F(4). The same element is used for transmit and receive. The receive signal is amplified prior to being sent to the system circuit via the shared cable wire. In this case, the low voltage receive amplification circuitry is detached from the cable and the element during each transmit period, when high voltage pulses are used. During each receive period, the element is attached to the low voltage amplification circuit and then to the cable wire.

Figure 3D:
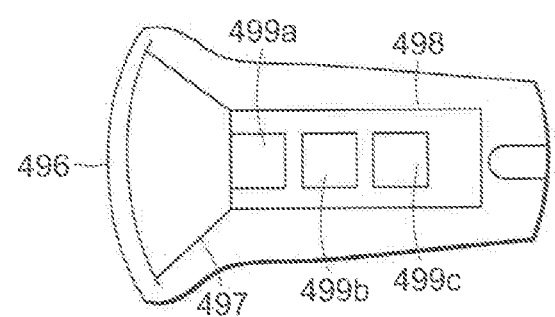
FIG. 3D illustrates a preferred embodiment utilizing a flexible circuit board and cable assembly.
Figure 3E:
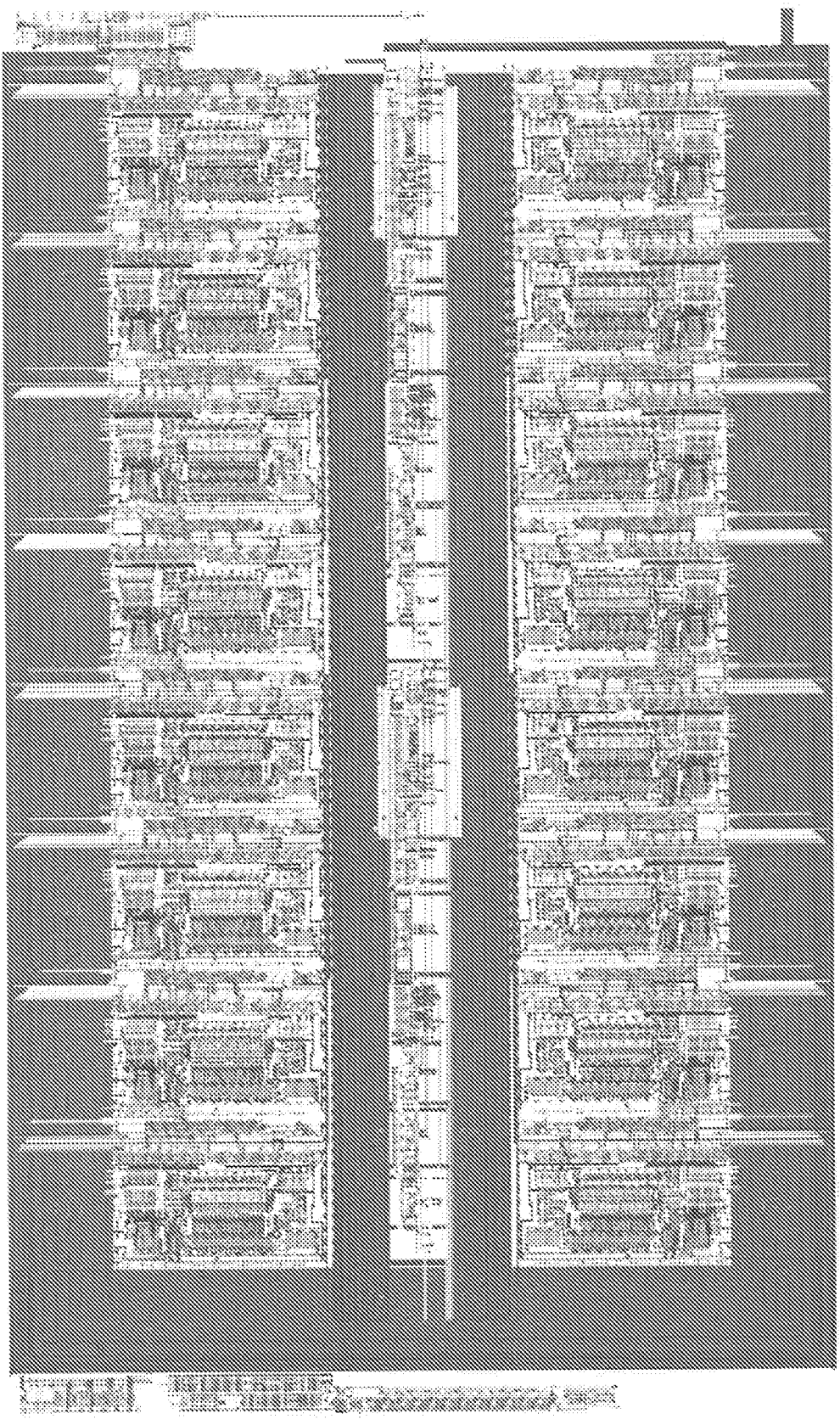
FIG. 3E is a photomicrograph of a preferred embodiment with an integrated circuit beamformer device having 16 channel subarray beamformers that can form 4 sequential beams.
Figure 3G:
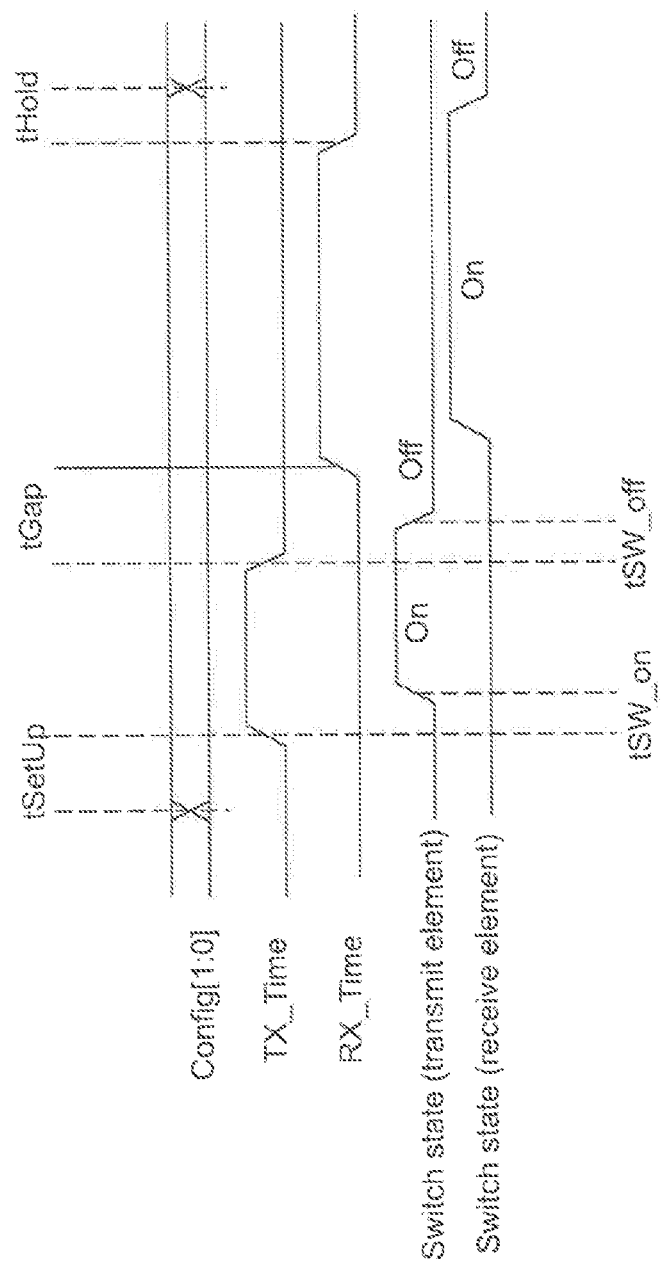
FIG. 3G illustrates a switch timing diagram in accordance with a preferred embodiment of the invention.

The chip shown in FIG. 3G is a multiplexer fabricated using high voltage CMOS process (>80V) The intended use is for embedding in the acoustic module handle of a medical diagnostic ultrasound probe where either two sets of transducer elements, transmit and receiver, or the subarray beamformed outputs and the transmit element share the same common transducer cable (COM). Multiplexing is achieved with two sets of high voltage switches, capable of handling high voltage bi-polar signals and frequencies up to 20 MHz. The turning on and off of these switches is controlled by two configuration signals (CONFIG. [1:0]) and two timing signals, TX_TIME and RX_TIME, which indicates when the system is performing transmit or receive. The CONFIG[1:0] can be used to configure the functionality of the port pins, for example, swapping the transmit and receive elements.

Figure 3H:
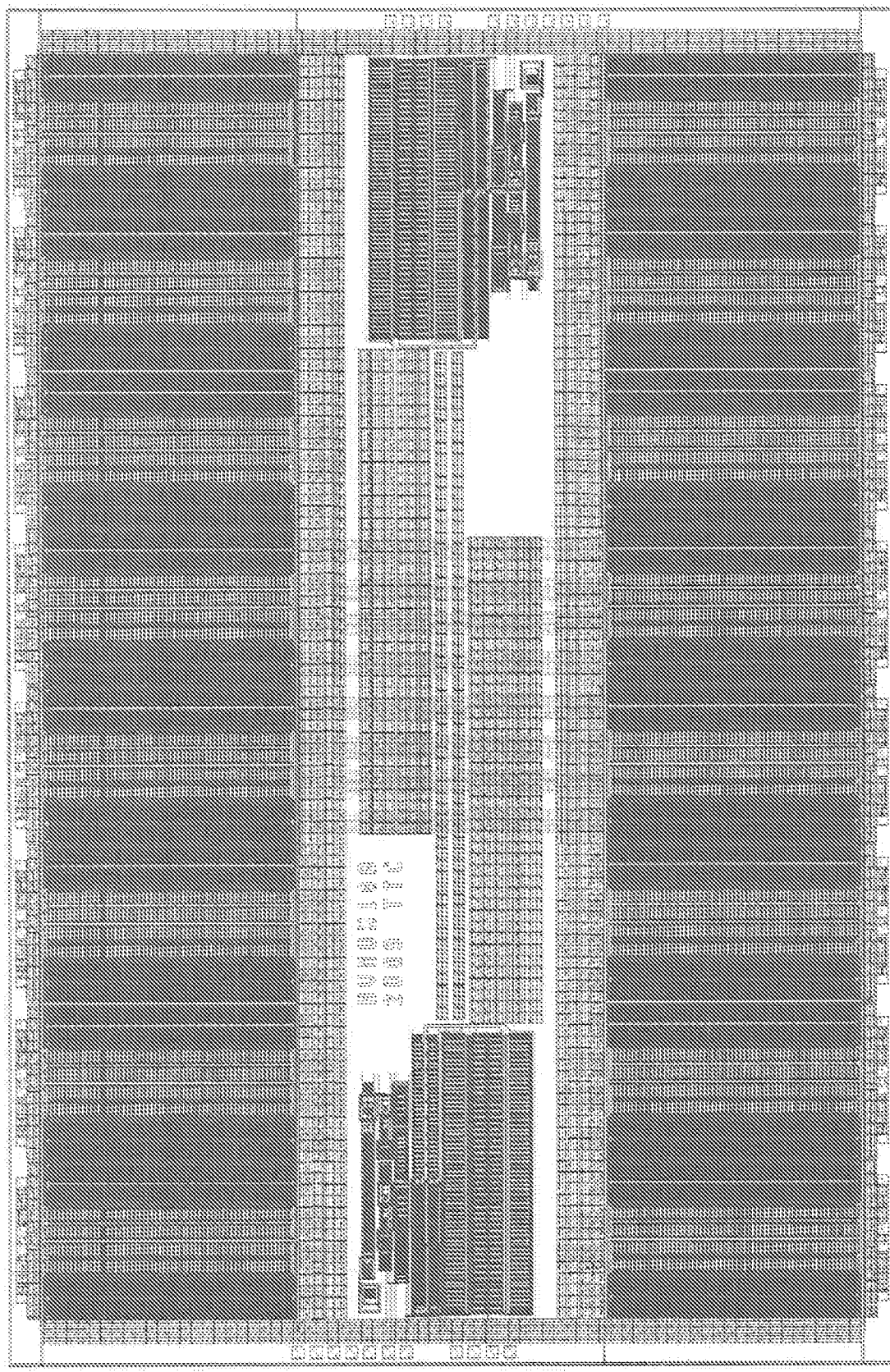
FIG. 3H is a photomicrograph of a 16 channel high voltage multiplexer integrated circuit chip in accordance with a preferred embodiment of the invention.
Figure 3I:
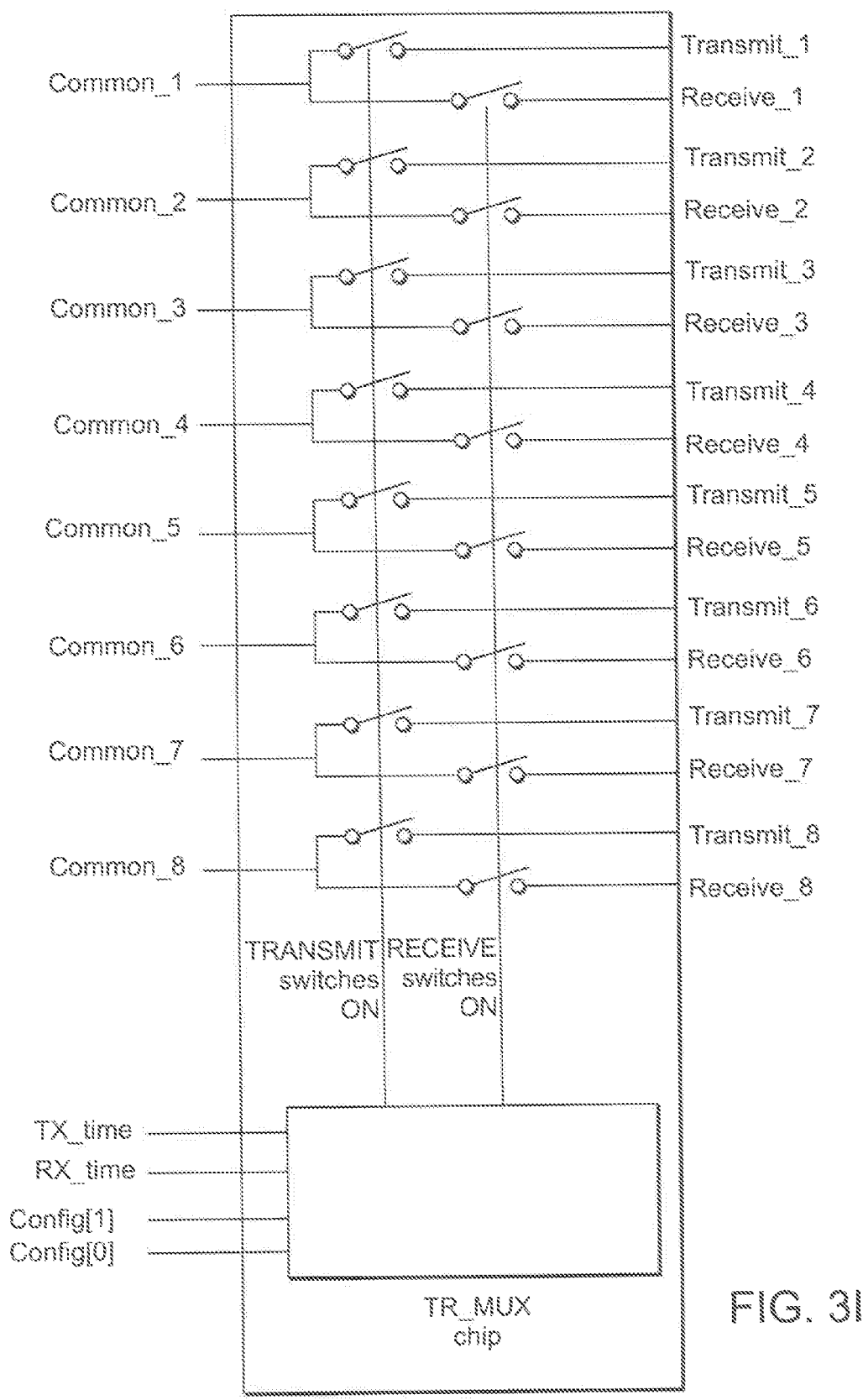
FIG. 3I is a schematic diagram of an 8 channel multiplexer chip in accordance with a preferred embodiment of the invention.

In operation as shown in FIG. 3G, the switches between the transmit elements and the common cable are turned on during the transmit period (TX_TIME=1), and off during the receive period (RX_TIME=1). The switches between the receive elements and the common cable are turned off during transmit and turned on during receive. The turn on/off time of the switches is less than microsecond with time skew less than 100 picoseconds. A photonmicrograph of a 16 channel high voltage multiplexer integrated circuit chip is shown in FIG. 3H that was manufactured using a 1 micron, two-poly, two-metal process and has a size of 14 mm×8 mm.

An implementation of 64 element 1D array with integrated first stage subarray processor can also be implemented using the design of FIG. 3C except that a single 64-element transducer array 491 is connected to a flex cable 497 with one end of the flex cable is connected to each of the transducer element, the other end of the cable is connected to a 64-pin flex connector. The connector is mounted on a printed circuit board. Within the printed circuit, there are eight 8-element subarray processors. Each subarray processor consists of eight programmable delay lines, each delay line has its separated low-noise pre-amplifier and at the output of the delay line, there is an apodizer, i.e., a multiplier for the beamshaping function. The outputs of the eight multipliers are summed together to form a single analog outputs. A high-voltage multiplexer circuit chip is also included on the printed circuit board, to allow the 64 element transducer either operated in transmit or receive mode. A memory chip is also mounted on the printed circuit board to store the programming delay for each of the delay lines. There are also power supply cables and digital inputs connected to each of the printed circuit boards.

A preferred embodiment of a 64 element (or more, e.g. 128 or 256 elements) 1D array 496 with integrated subarray processor is shown in FIG. 3D. In this implementation, instead of using a printed circuit board, the subarray processing chip 499a, the high voltage multiplexer circuit chip 449b and the memory chip 449c are mounted on the flexible printed circuit or cable directly (497, 498).

Alternatively, the beamforming processor can be mounted on a printed circuit board has to provide the subarray beamforming function for a total of 64 receive elements which are divided into 8 subarrays with each subarray consisting of 8 adjacent elements. 8 subarray processors each can perform the beamforming function, i.e., time-delay-and-sum function, for 8 adjacent receive elements are incorporated on the circuit board. A photomicrograph of a 16 channel subarray beamformer chip shown in FIG. 3E, for each transmit pulse, the chip is capable of forming 4 sequential beams for 16 receivers. The chip also uses the 0.35 μm double-poly, four-metal process. The size of this chip is 1.2 mm×0.6 mm. As in the prior embodiment, 4 such 16 subarray processor can easily be integrated on one chip with a chip size about 1.2 mm by 2.4 mm, so the board only requires one such subarray beamforming chip.

As pointed before for dynamic focusing, each beam needs two digital update bits; one for tap update and one for interpolation. To support the 4-beam sequential outputs, the two-digital update bits of each beam are dynamically loaded into the chip at an eight times input-sampling rate, so to allow continuous subarray beamforming function at the analog input sampling rate. If the range depth is 15 cm, for a 2 Mhz probe oversampled by 4, the total received beamforming are 2000 points. In the embodiment, the memory size on the board shown in FIG. 3E is 64×4×2×2000=1 Mbits where compression method can be used to reduce the memory size. The systems described herein can be used with a catheter or probe for insertion within body cavities for cardiac imaging (4D) or other internal organs. The probe or catheter assembly can include a circuit housing with the first plurality of beamformers as described herein.

Existing are medical ultrasound systems with matrix-array transducers can provide real-time 3D (RT-3D) echocardiography along with state-of-the-art 2D imaging. The major advantages of RT-3D acquisition compared with 2D image include shorter acquisition times, reduced operator dependence, and the ability to manipulates images offline to extract any number of desired views for data analysis. Furthermore, quantitative data regarding Left Ventricle volumes and ejection fraction are more precisely obtained using the 3D technique. Although the term "real-time" is applied to all of the currently available 3D echocardiographic technology, it is important to recognize that in the current scanners, "live 3D" refers to true real-time images that are acquired without electrocardiographic gating. However, this type of real-time 3D imaging has a narrow sector with only a partial volume and is not suitable for imaging the left ventricle.

To obtain full-volume 3D images in current scanners, electrocardiography is used to gate the image acquisition. Four to 7 subvolumes are acquired over 4 to 7 cardiac cycles and then merged to obtain a complete data set, shown in FIGS. 4A-4D. Note that the healthy adult human heart generally has a volume in a range of 200-500 ml/m². See, for example, Chikos et al. "visual assessment of Total Heart volume and Specific Chamber Size from Standard Chest Radiographs," Am. J. Roentgenol 128:375-380, March 1977, the entire contents of which is incorporated herein by reference. Thus it is desirable to image a volume larger than 200 ml/m² in order to capture a 3D image of the adult human heart based on a singe transmission pulse sequence. Thus, the transducer array has an aperture sufficient to transmit and receive signals within this volume range substantially simultaneously, i.e. in less than one cardiac cycle.

Figure 4A:
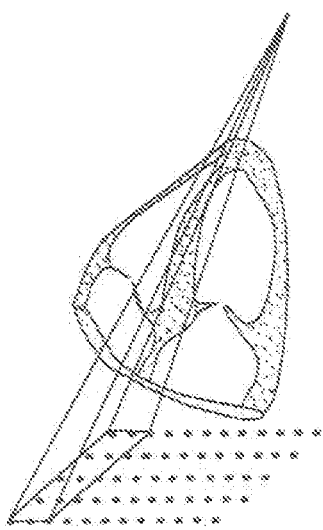
FIGS. 4A-4D illustrate a gated acquisition sequence for cardiac imaging.
Figure 4C:
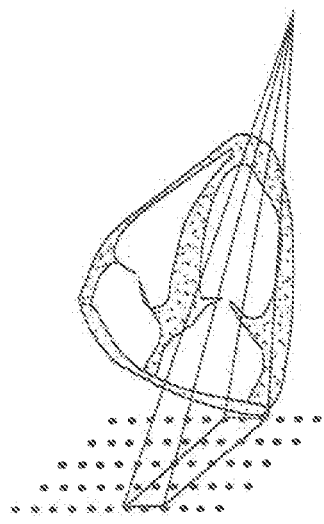
Figure 4D:
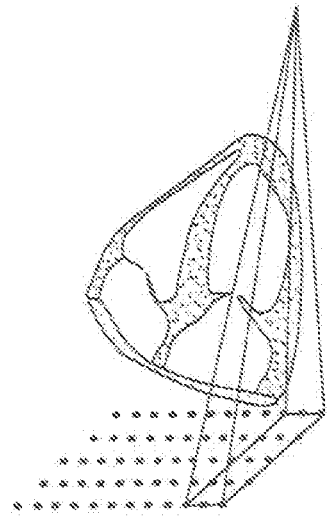
Figure 4B:
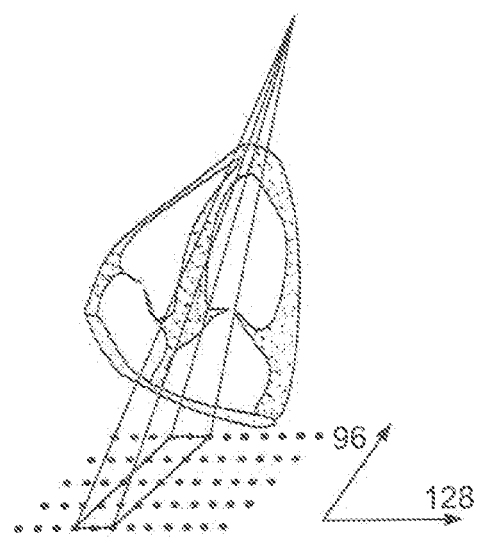

As indicated, about 128 by 96 beams are required to provide the complete coverage of the left ventricle. In a conventional implementation, during the first cardiac cycle with electrocardiographic gating, 32 by 96 beams are used to acquire part of the 3D image (FIG. 4A). During the second cardiac cycle, the second set of 32 by 96 beams is used to cover the adjacent part of the cardiac image, FIG. 4B. The procedure follows (FIGS. 4C-4D), until the $4^{th}$ cardiac cycle with electrocardiographic gating; the last portion of the cardiac image is then acquired. The four images are then merged together to provide the complete 3D image. This technique offers a wide sector angle and generates a full-volume image after recording a sequence of multiple cardiac cycles. However, stitching artifacts can occur with movement and in patients with arrhythmias and respiratory difficulties, resulting in nondiagnostic images. Therefore, the current RT-3D technique used for echocardiography is near real time, but not truly real time.

Figure 4E:
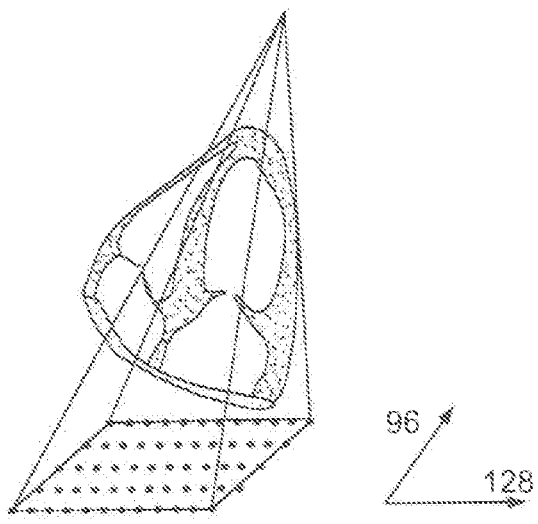
FIG. 4E illustrates a full cardiac imaging ultrasound scan using a plurality of beams with a single transcript pulse with at least six 3D volumetric images per second.

A preferred embodiment of the present invention generates 16 scanning teams for each transmit pulse, as a result, it generates a true "live 3D" image with 128×96 scanning beams operating at least at a six 3D volumetric images per second rate. The speed of sound in tissue is about 1500 cm/sec, the round-trip propagation time for a sound wave penetrating a 15-cm depth is about 200 microseconds. For 3D imaging, such as of the heart including both left and right ventricles, as shown in FIG. 4E, 128×96 scanning beams are needed to provide a wide sector view angle. The total round-trip time required for the 128×96 beams is 128×96× 200 microseconds=2.45 seconds. The present invention forms 16 received beams for each transmit pulse, it follows then that only 2.45/16=0.15 s is needed to generate a single 3D volumetric image with 128 by 96 beams or six 3D volumetric images per second. At a six 3D volumetric images per second rate, the scanner provides real-time 3D diagnostic quality images for coronary artery disease detection. Thus, preferred embodiments generate at least four full volume cardiac images per second.

Systems used to generate at least 16 beams for each transmit pulse are shown in the embodiments of FIGS. 4F-4K. systems employing a phase shifting approach can also be used to achieve full volume imaging.

Figure 4F:
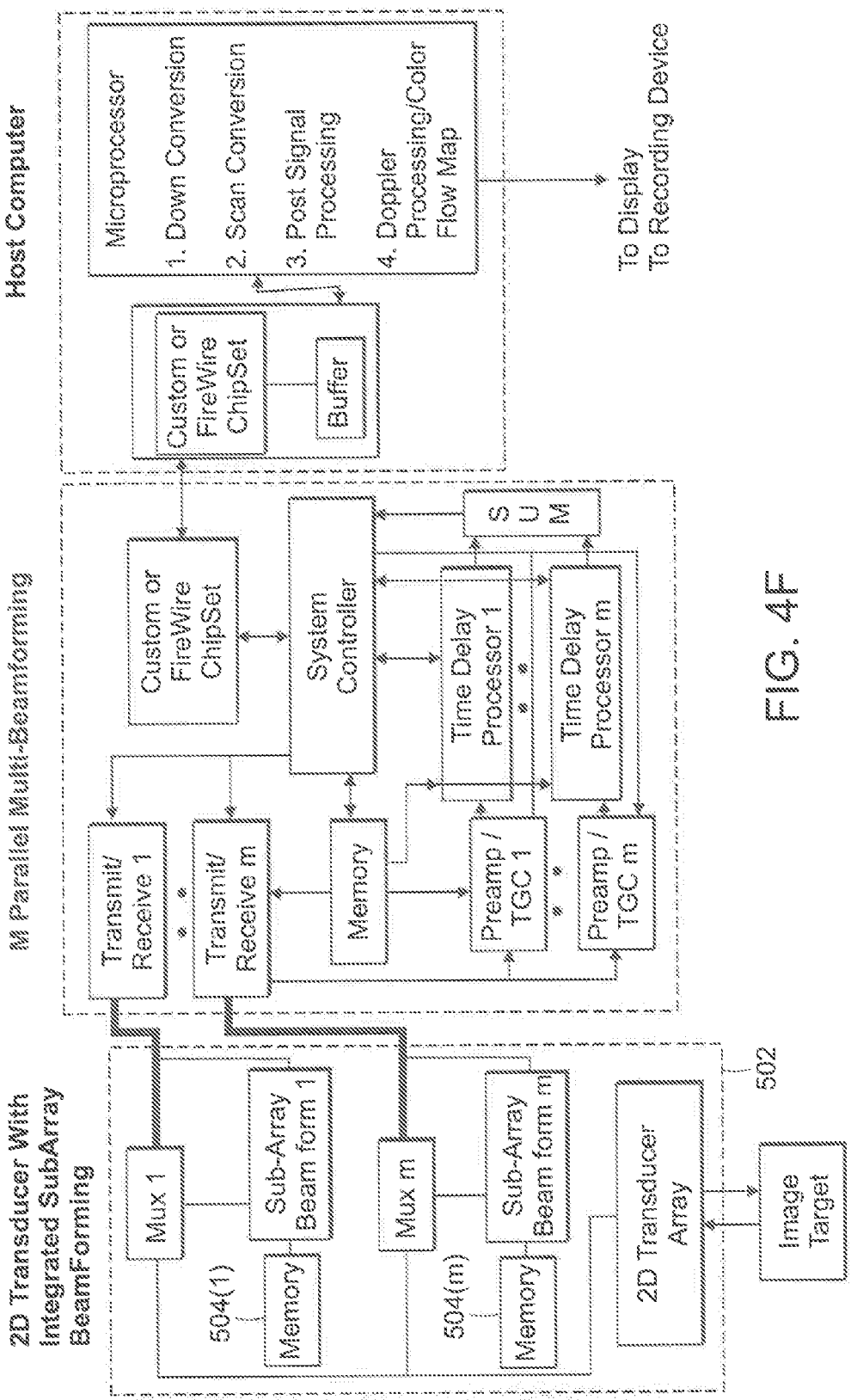
FIG. 4F illustrates an ultrasound system using a probe such as that shown in FIG. 3C.

An ultrasound system using a probe such as that shown in FIG. 3C is illustrated in the diagram of FIG. 4F in which a 2D transducer with integrated MUX, memory and subarray beamformer. The subarray beamformer has a low-noise input amplifier and memory 504(1), 504(m) in the scanhead 502.

Figure 4G:
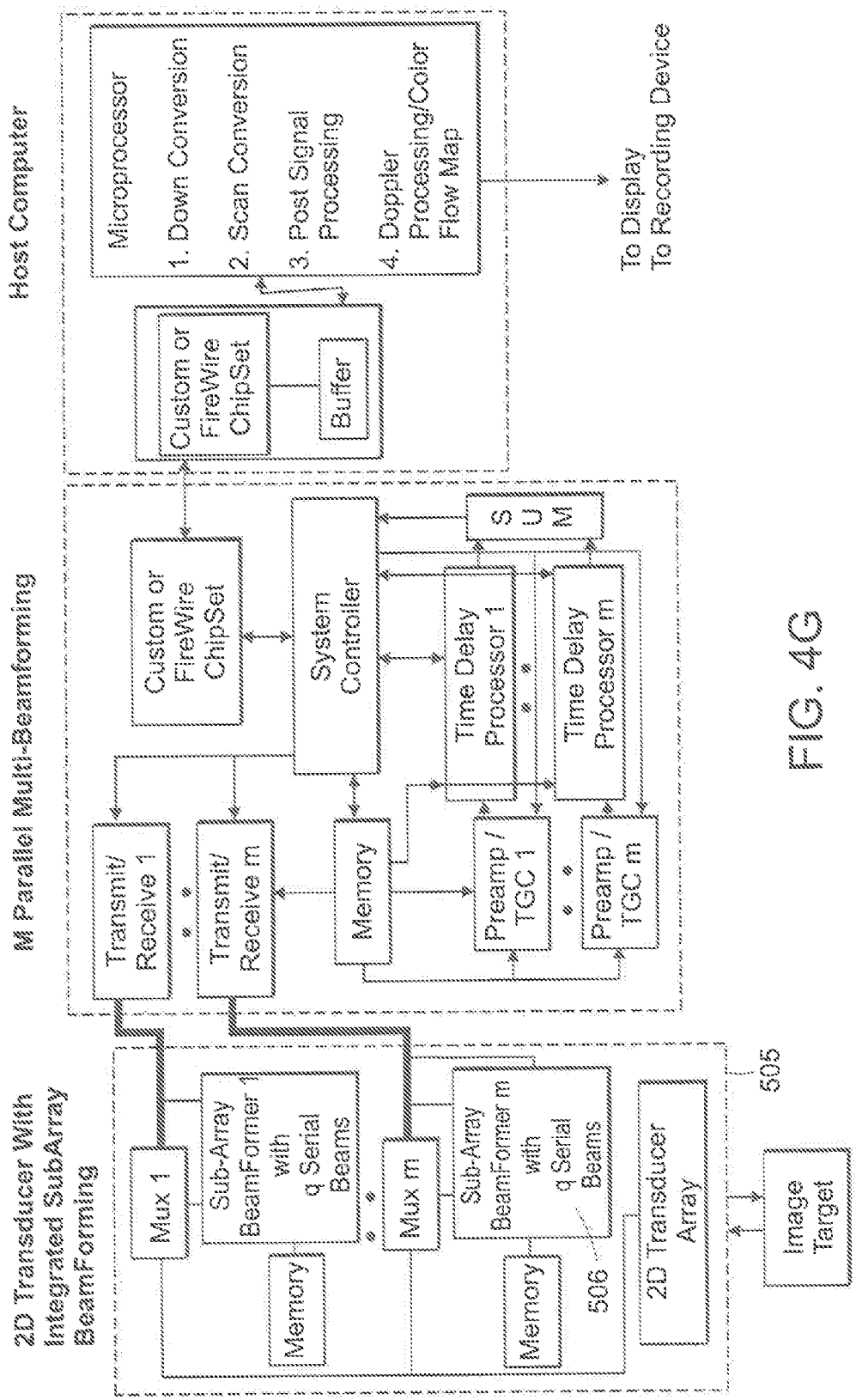
FIG. 4G illustrates an ultrasound system has a subarray beamformer with serial beam output.
Figure 4H:
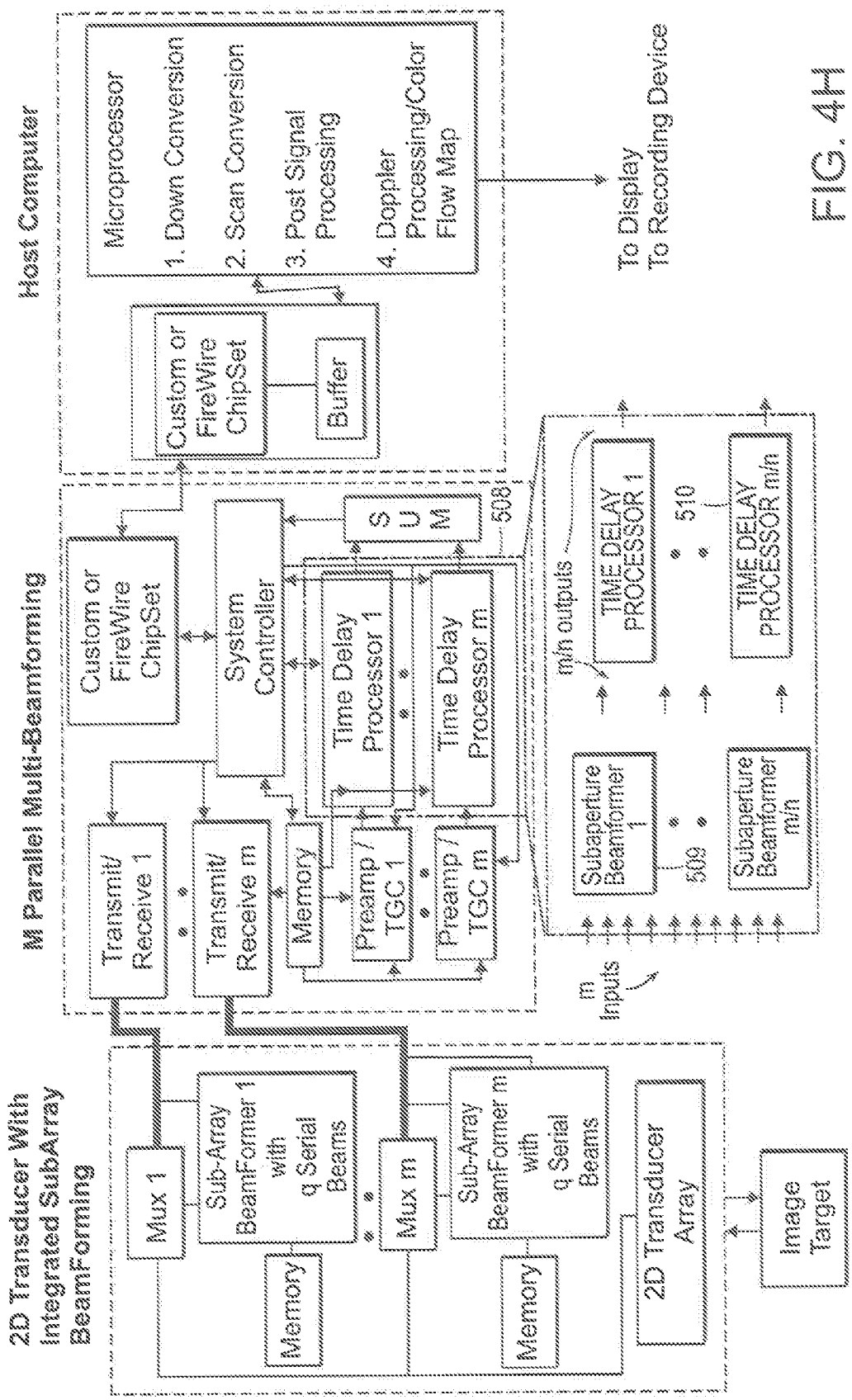
FIG. 4H illustrates an ultrasound system with a second stage subaperture beamformer (509) that generates an output for a third stage beamformer (510).
Figure 41:
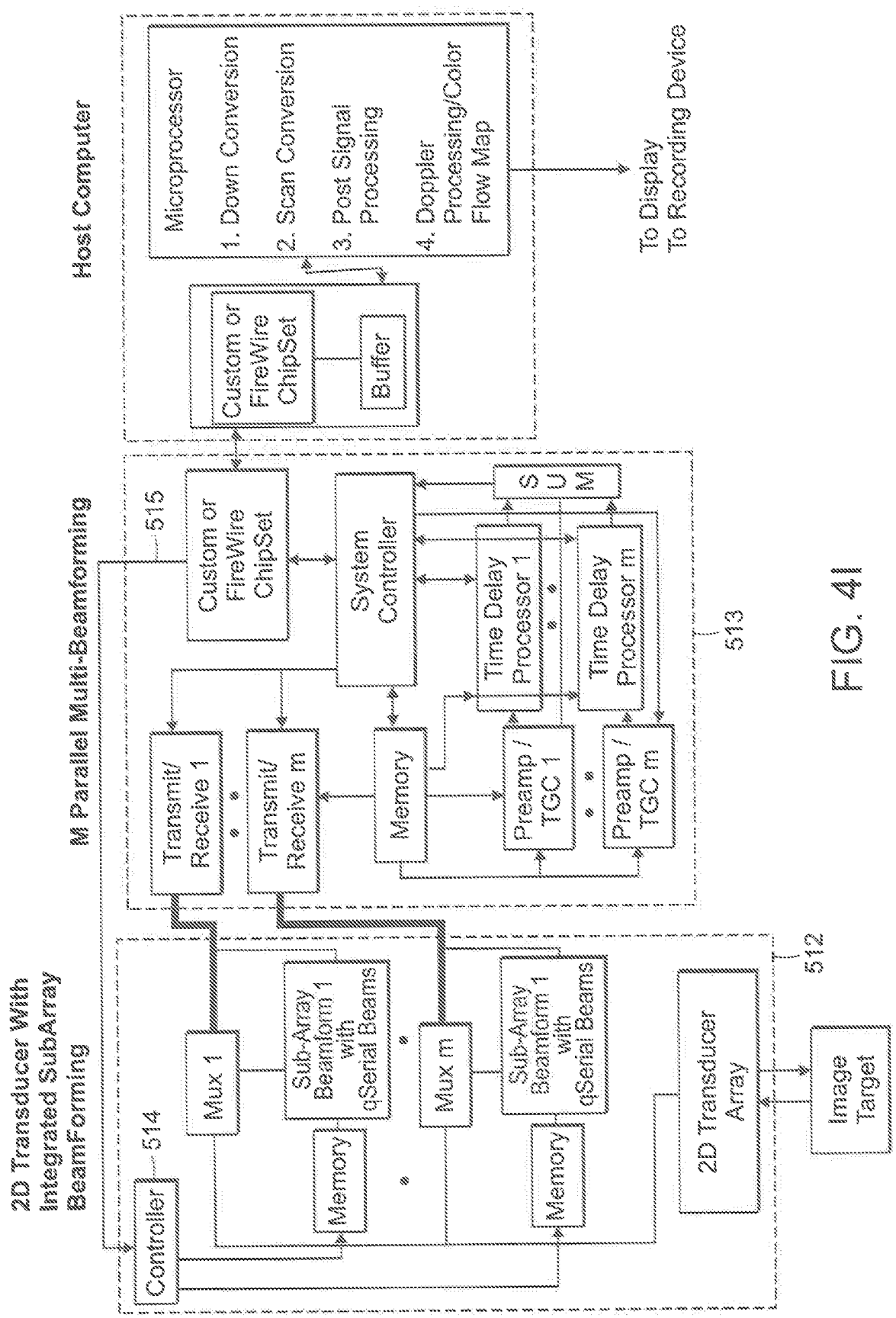

FIG. 4G illustrates a system with 2D transducer with integrated MUX, memory and subarray beamformer in a probe 505 with serial beam output 506. In this mode, the back-end time delay processor has to run at a rate that is q×transducer input sampling rate, i.e., if the center frequency of the transducer is 2 Mhz, the probe is oversampled at 8 Mhz rate. If four serial outputs are generated by the subarray processor, ie., q=4, the back end processor has to run at 32 MHz rate. The subarray beamformer has a low-noise input amplifier FIG. 4H illustrates a system with 2D transducer with integrated MUX, memory and subarray beamformer with serial beam output. In this mode, the back-end time delay processor has to run at a rate that is q×transducer input sampling rate, i.e., if the center frequency of the transducer is 2 Mhz, the probe is oversampled at 8 Mhz rate. If four serial outputs are generated by the subarray processor, ie., q=4, the back end processor has to run at 32 MHz rate. In this approach, the back-end processor uses subaperture beamforming system 508, i.e., the n adjacent receive channels are grouped together, formed first stage beamforming device 509 and then share a common long delay line 510. So, the inputs to the back end are m channels. However, the back-end output to the summing circuits are reduced to m/n outputs. For example, if the transducer array are 64×48 elements, a 4×4 subarray is used for subarray beamforming, the total outputs from the integrated probe is then 64×48/ 16=192 cables, i.e., m=192. However, in the current implementation, a subaperture size of 8 is used, i.e., n=8, it follows then the total number of long time delay processors are 192/8=24. The subarray beamformer has a low-noise input amplifier.

FIG. 4I includes the elements of the system shown in FIG. 4G, however, a controller 514 is incorporated in the front-end probe 512. The controller can be formed on a third circuit board along circuitry for a wireless or cable connection 515 to the external housing 513 which can be an interface to the main system processor or can be integrated into a cart system or a portable system as described herein.

Figure 4J:
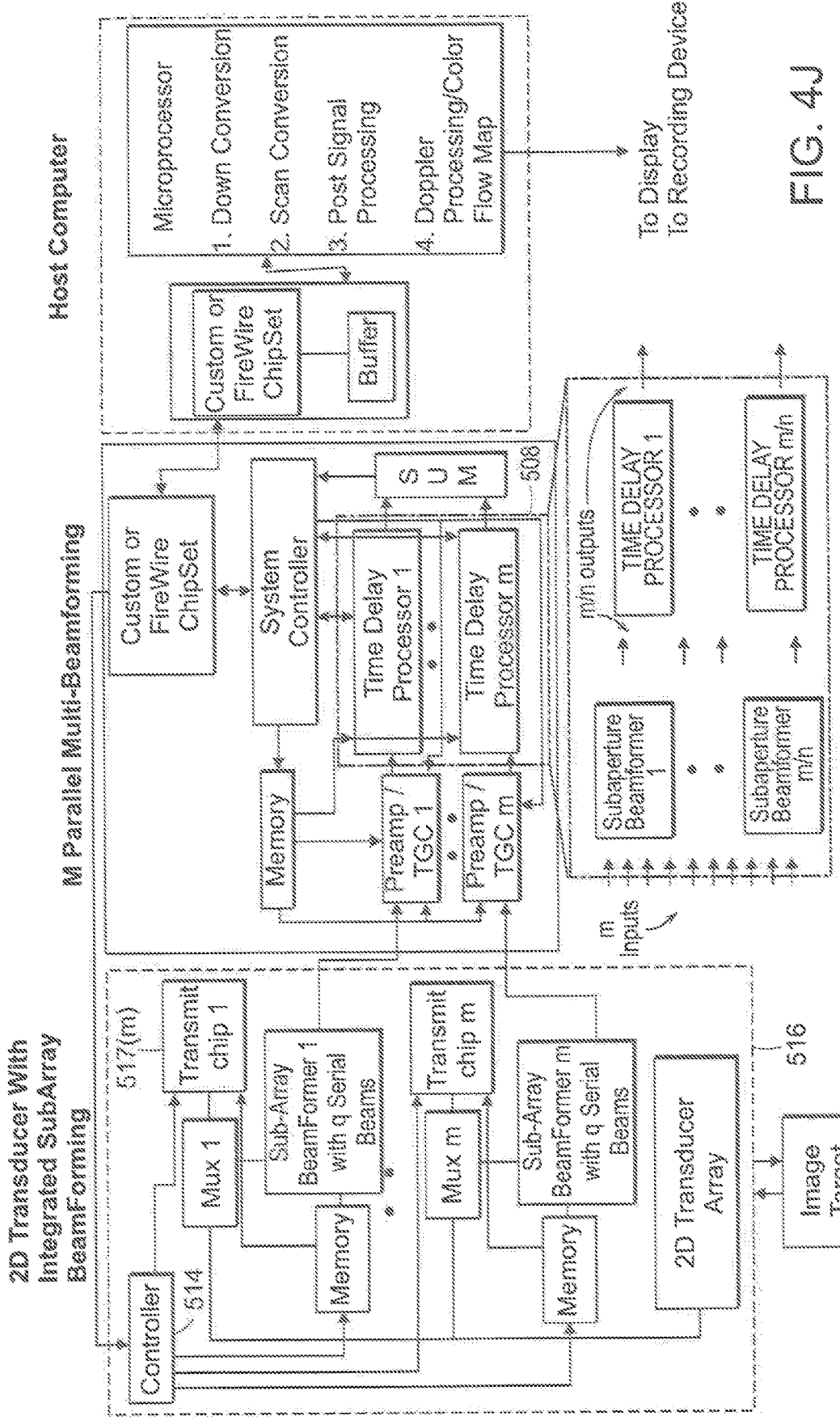
FIG. 4J illustrates an ultrasound system with a controller and transmission circuit integrated in the transducer probe housing.

FIG. 4J is a similar architecture to what described in FIG. 4H, however, a controller 514 is integrated into the front-end. i.e., the interconnection cable are m=192 channels, however subaperture beamformers are incorporated into the backend process, n adjacent receive channels are beamformed first and then applied to the back-end time delay process, if n=8, the outputs to the summer are only 24 channels. In addition, an optional approach of integrating transmit chips 517(m) into the front-end integrated probe is used. However, the transmit channel can be located in the back-end processor as indicated in FIG. 4I.

Figure 4K:
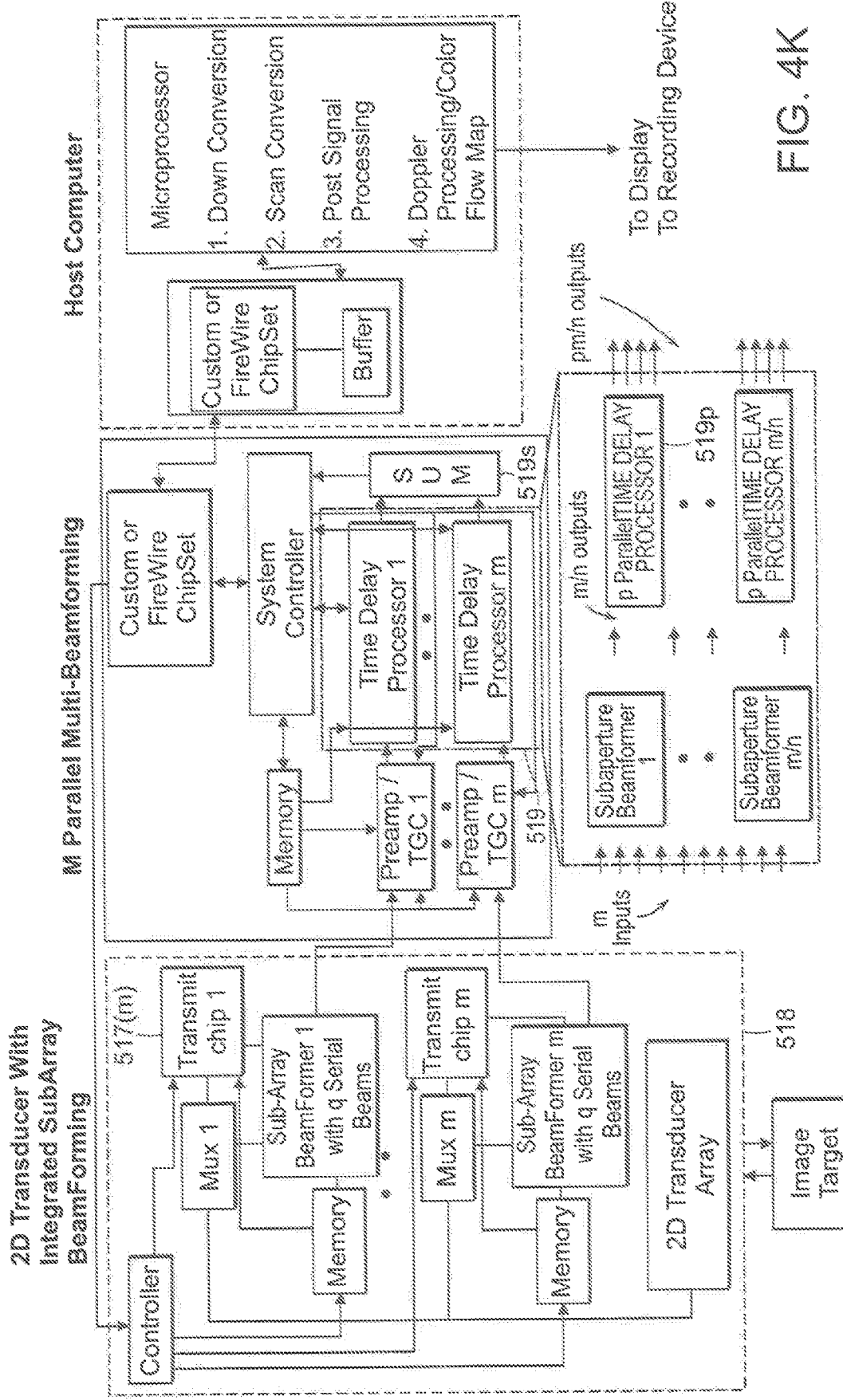
FIG. 4K illustrates an ultrasound system with parallel time delay processors (519P) producing parallel output data.

FIG. 4K is similar to what used in FIG. 4J, however, in the back end processors, p-parallel beams are formed with each of the subaperture beamformers 519 and parallel delay processor 519P. So, if p=4, that is for each output ream from the front-end integrated probe 518, four parallel beams are formed, each of the 4 outputs are summed together at the summer 519S. This is how 16 beams are formed for each transmission, i.e., in the probe, q=4, four serial beams are formed, in the back-end p=4, four parallel beams are formed. With p times q=16. Please note in FIG. 4K, a transmit circuit has also been included in the front-end integrated probe. However, note that the transmit chip can be located at the back-end processor, in addition, in FIGS. 4F-4K a 2D transducer array is used, the architecture can also ne used with a 1D transducer array with subaperture beamforming. These systems provide full volume cardiac imaging that can produce video imaging of the heart including left and right ventricles at video rates of at least 4 full volume images per second and preferably 6 full volume images per second or more.

Figure 5A:
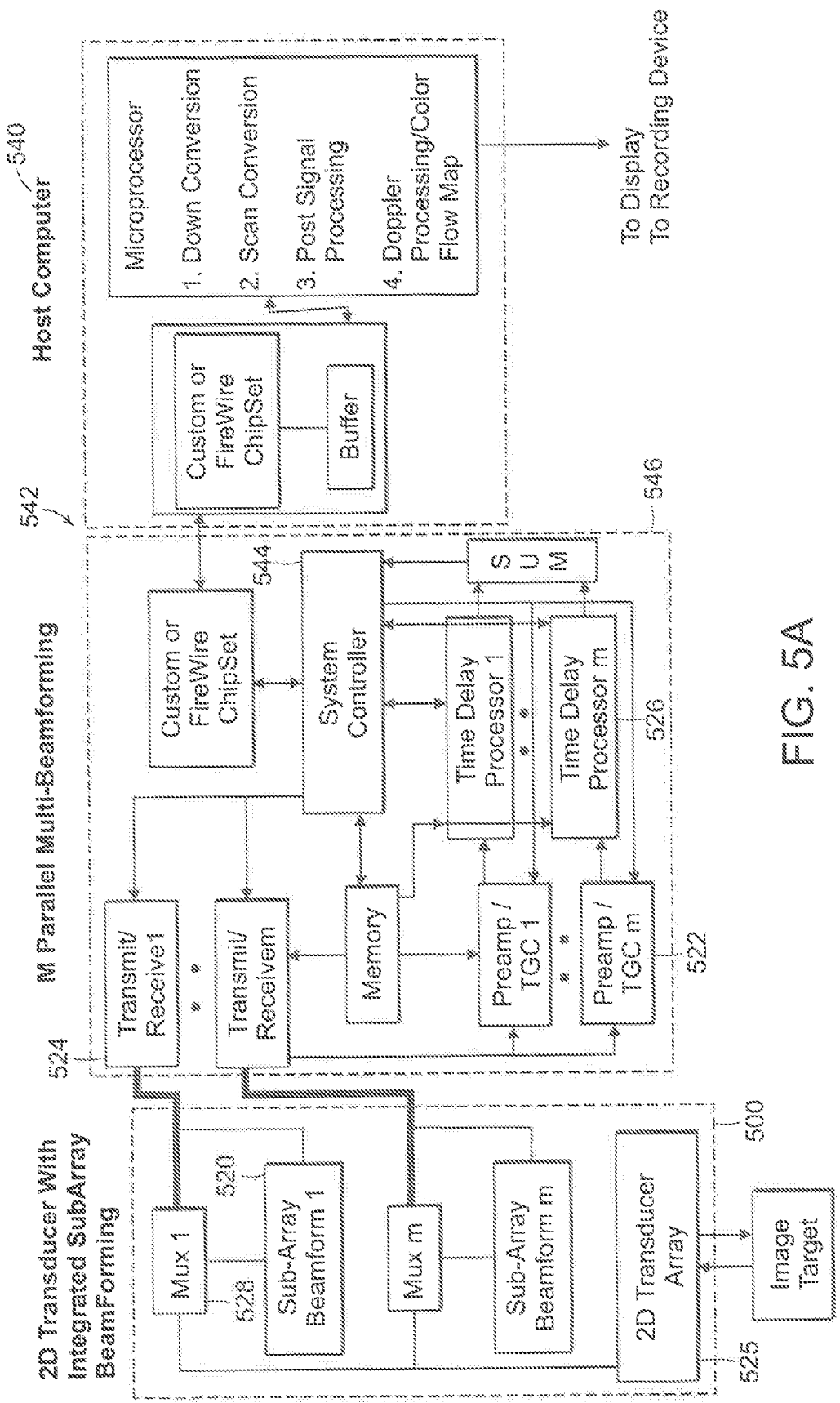
FIG. 5A illustrates a preferred embodiment of a three dimensional imaging system in accordance with the integrated Subarray scan head invention.
Figure 5B:
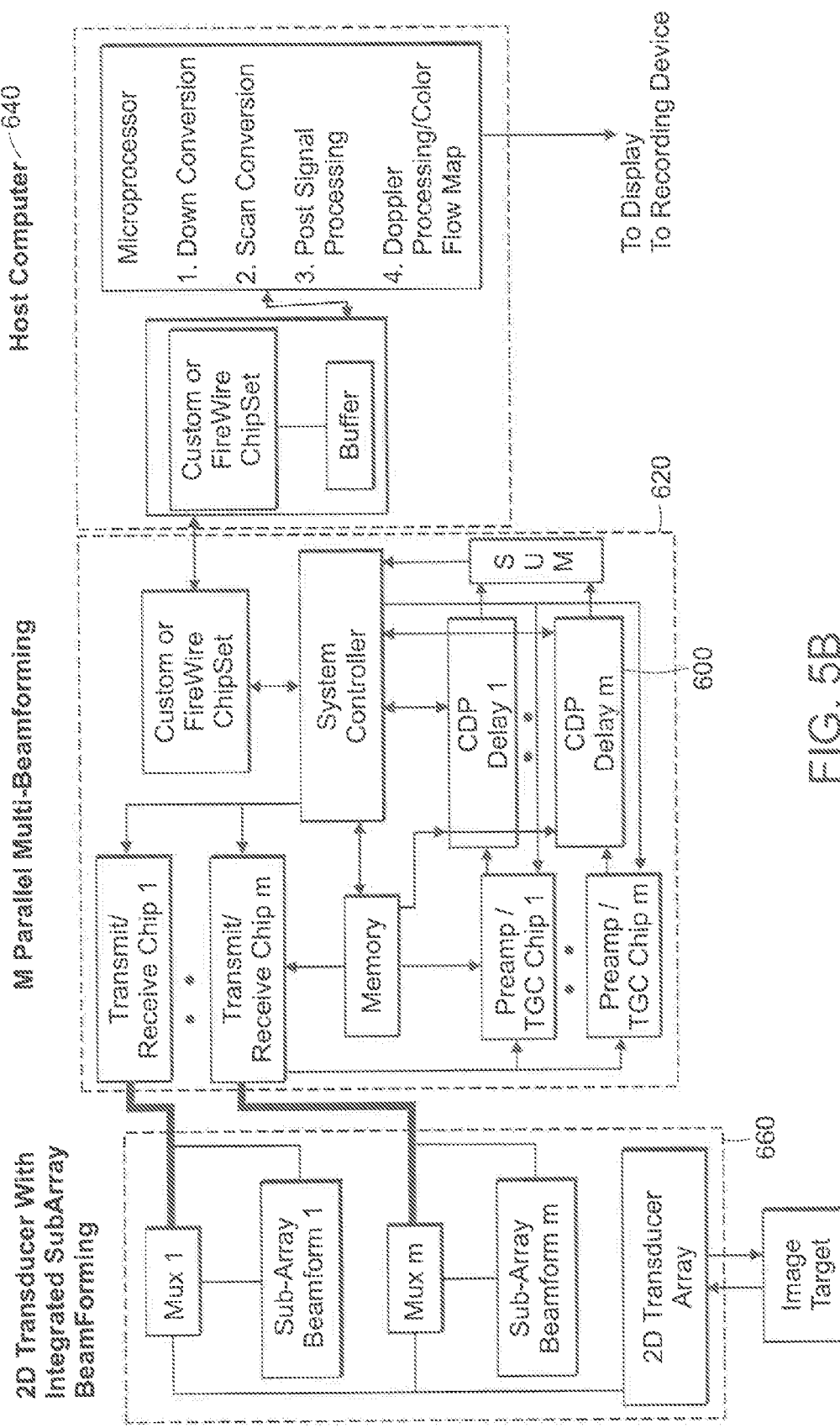
FIG. 5B illustrates a preferred embodiment of the integrated Subarray scan head invention using a charge domain processor for the $2^{nd}$ time delay beamforming.
Figure 6A:
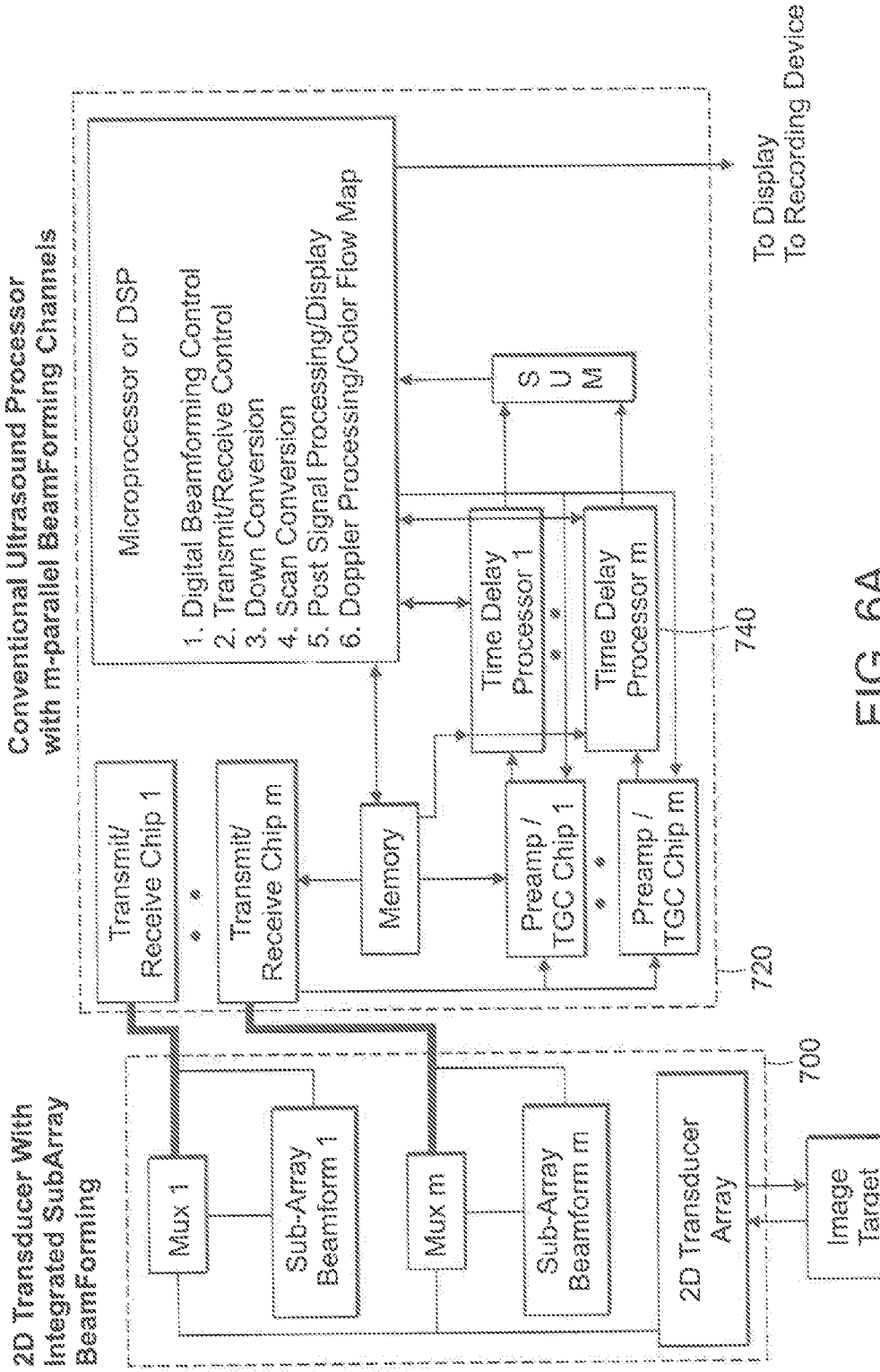
FIG. 6A illustrates the use of the integrated subarray scan head probe of the present invention with a second stage beamforming ultrasound processor.
Figure 6B:
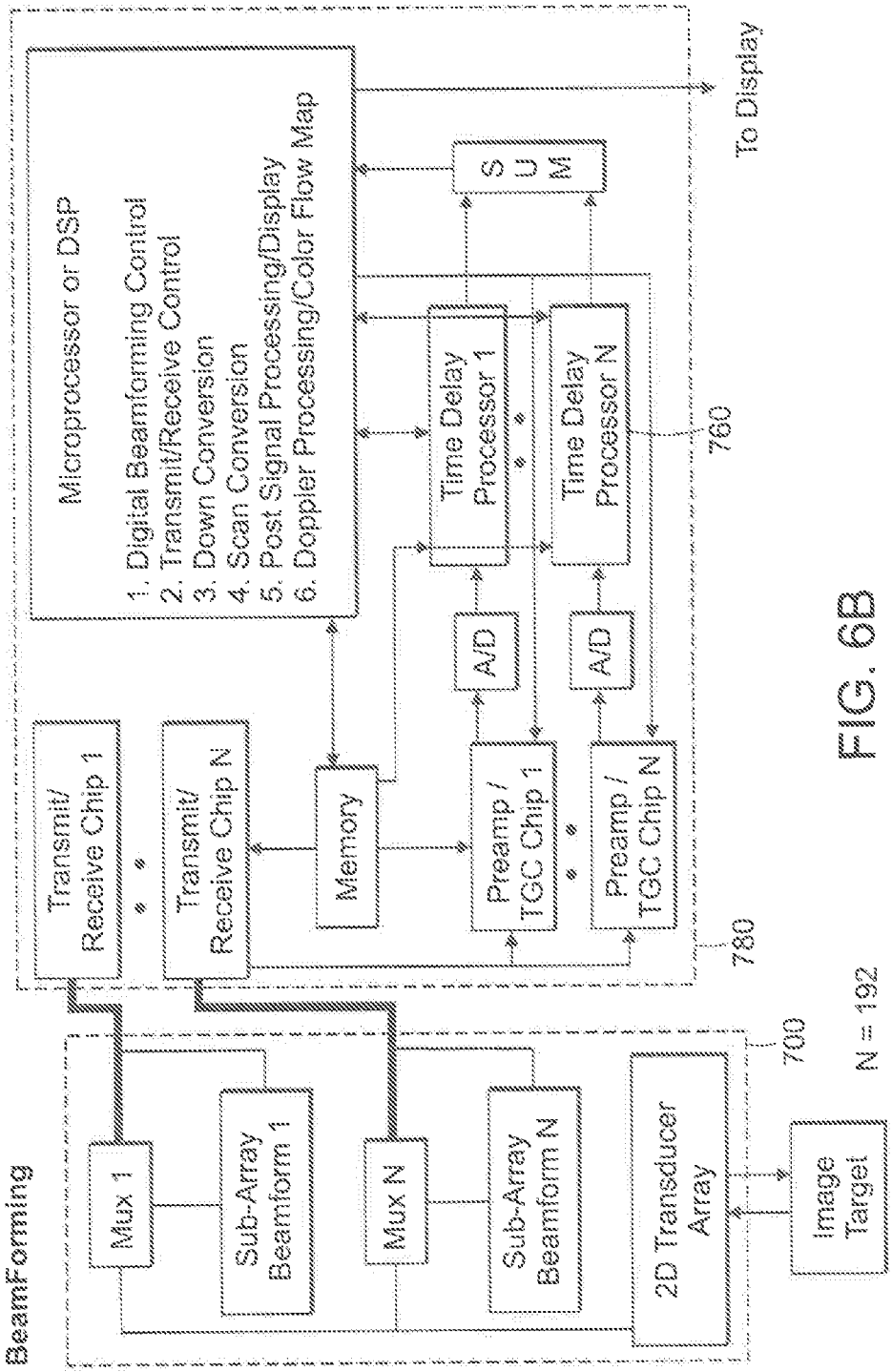
FIG. 6B illustrates use of the integrated Subarray scan head with a digital beamforming processor.

A preferred embodiment of the invention for 2D array beamforming, each minimizing noise and cable loss with improved S/N performance, are described in FIGS. 5A, 5B, 6A and 6B. In there implementations, the bank of m parallel subarray beamforming processors 520 and multiplexers 521 are integrated with the 2D transducer array 525 to create a compact, low-noise, scan head 500. FIG. 5A depicts a system that the compact scan head is connected to a dedicated processing module, in which the m-parallel preamp/TGCs 522 transmit/received chips 524 and the $2^{nd}$ stage time delay processing units 526 are housed. This dedicated processing module communicates with a host computer 540 via FireWire IEEE 1394 or USB or PCI bus 542. Control and synchronization is performed by the system controller 544 located in the processing module or housing 546. FIG. 5B depicts the same architecture as stated in FIG. 5A, except that inside the dedicated processing module, the $2^{nd}$ stage time delay processing units are specifically implemented by using charge-domain programmable (CDP) time-delay lines 600 in housing 620 that is connected to handheld probe 660 and computer housing 648. FIG. 6B depicts a system that the compact sparse array scan head 700 is connected to a conventional, commercially available time-domain digital ultrasound imaging system 700 with n-parallel beamforming channels 760. It is easy to see that in FIG. 6A, the time-delay processor 720 can also be implemented by using CDP time-delay lines 740. In these embodiments the near-field beamforming is housed 720, 780 in the same housing with other image processing functions. These systems are described in International Application No. PCT/US2007/014526 filed Jun. 22, 2007, designating the United States and U.S. application Ser. No. 11/474,098 filed Jun. 23, 2006, both applications being incorporated herein by reference in their entirety.

Figure 7:
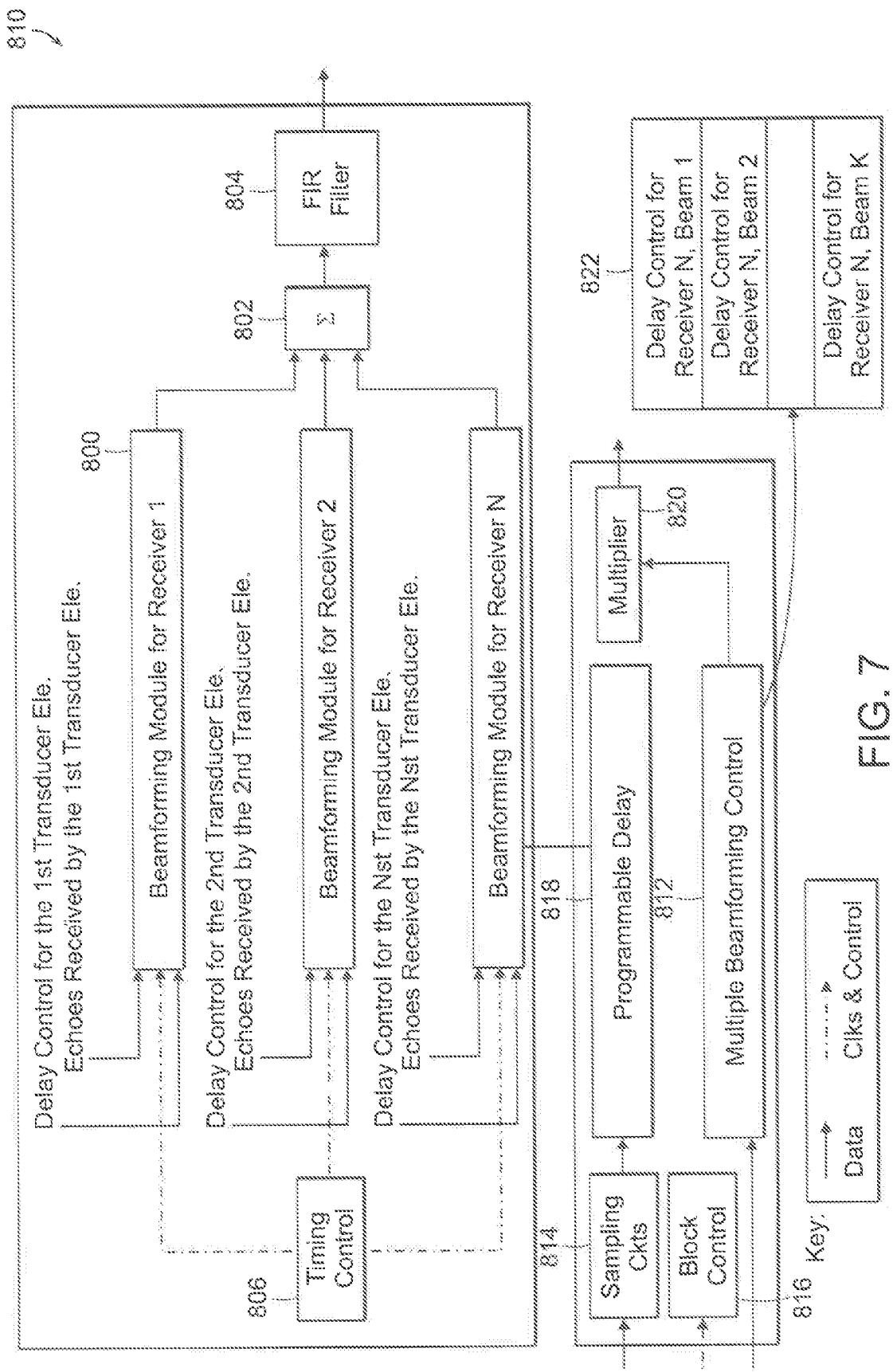
FIG. 7 illustrates an ultrasound system in accordance with the invention.

By systematically varying beamformer delays and shading along a viewing angle of a 2 transducer array, returned echoes along the line of sight representing the 3D radiation sources can be used to create the scanned image at the scanned angle. The system can provide continuous real-time large area scanned images throughout a large field of view at 20 frames/s or more. At this frame rate, the system can be used to display continuous 3D images vs. time, thus providing 4D information of the scanned object. As shown in FIG. 7 a CDP beamforming chip 810, a time multiplexed computing structure can ne used to generate multiple beams, i.e., for each transmit pulse, the bank of 2D subarray beamformers 818 and its corresponding $2^{nd}$ stage near-field time-delay line are capable of providing multiple beams sequentially. The computing circuits sequentially generate the delays required for forming K beams. The device operates as follows. Once a set of sampled returned-echoes are loaded in the delay lines with sampling circuits 814, at time $t_1$, the delays required for forming beam 1 are computed 112 within each module 822 and applied in parallel to all delay lines. The sampled return-echoes with proper delays are coherently summed 802 and filtered 804 to form the first beam. At time $t_2$, the delays required for forming beam 2 are computed within each module and applied in parallel to all delay lines. The sampled return-echoes with proper delays are coherently summed to form the second beam. The procedure repeats until the Kth beam is coherently formed.

For example, if a computing circuit, with 16-serial addressable outputs is built in with the CDP subarray and the $2^{nd}$ stage time delay lines, for each transmit pulse, 16 beams or scan lines each along a different scan angle can be created. For 256-pulses with a down-range depth of 15 cm, the system can generate a 4096-beams with a 64×64 pixel resolution at a frame rate of 20 frames/s. The system is fully programmable; the beamforming electronics can be adjusted to zoom-in to a smaller field-of-view for high-resolution or higher frame rate images. For example, using 192-transmit pulses with the same down-range depth of 15 cm, the system can generate a 3072-beams with a 64×48 pixel resolution at a 30 frame/s frame rate.

The array described addresses ultrasound imaging applications using a two-dimensional 2 cm×2 cm array at a frequency of 3 MHZ. The need for resolution on the order of less than half the wavelength dictates as large an aperture as possible that can be housed within a compact package. To interrogate a 90 degree scanning volume and also minimize the impact of grating lobes, an element pitch or separation of less than 0.25 mm is desirable, leading to a 80×80 element array. Using the subarray processing technique described above, a scan head with integrated subarray beamforming circuits followed by a $2^{nd}$ stage near-field beamsteering/beamfocusing system provides a practical implementation. However, the implementation still requires at least 32 subarray chips to be integrated on a scan head. An alternative pseudo random array design approach can be used to achieve this resolution with a much less amount of processing components in the scanned head.

To make a sparse array practical, the combination of low insertion loss and wide bandwidth performance is important for realizing acceptable imaging performance with low illumination levels. Quarter-wave matching layers with low acoustic impedance, but physically solid backing results in a robust array that loses only 3-4 dB in the conversion of received signal energy to electrical energy. Array bandwidths of 75% or more are typical of this design and construction process. Also, the transducer array employs element positioning and an interconnect system suitable for the beamformer circuitry. The electronics are mounted on printed-circuit boards that are attached to the transducer elements via flexible cables. In practice, a majority of the array elements are connected to outputs using the flexible cables. However, only a small fraction of the total number of elements are wired to the circuit boards. Nevertheless, the large number of array element connections are sufficient to insure a unique pattern of active-element locations in the final array.

As an example of a sparse array, assuming a 2×2 cm array with 256 active elements, the resulting filling factor is 4%. The output signal to noise ratio of the array is proportional to the number of active elements, so this filling factor corresponds to a loss in sensitivity of −13 dB when compared to a filled array of the same dimensions. To compensate for this loss, a transmitted signal of wider bandwidth is chosen to increase array sensitivity. In the approach presented here, the sensitivity is increased on the order of 10 dB. Further details regarding sparse array devices can be found in U.S. Pat. No. 6,721,235, the contents of which is incorporated herein by reference.

Figure 8A:
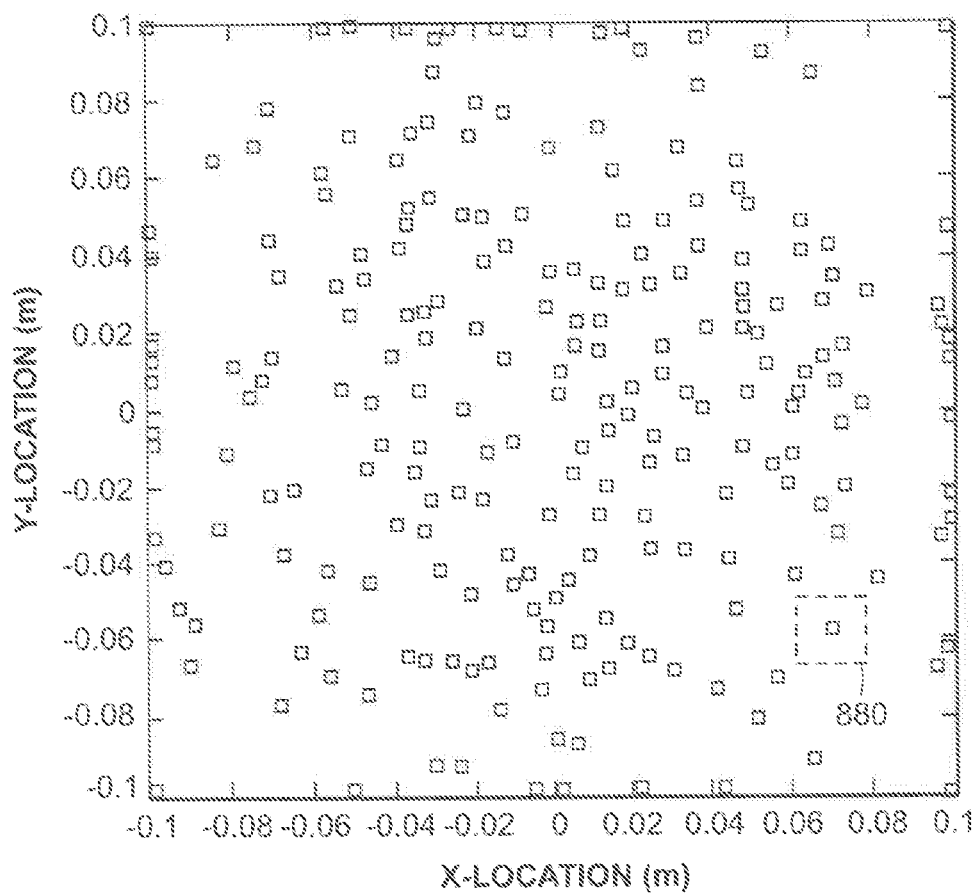
FIG. 8A illustrates a sparse array used in accordance with the invention.

Positioning the elements of the array follows the approach in which care must be taken to eliminate any periodicity that would produce grating lobes that compete with the main lobe. Pseudorandom or random arrays can be used (FIG. 8A). The geometry of activated element placement has been developed to maximize the efficiency of the beamformers while minimizing grating and side lobe clutter. Switching between a plurality of different array patterns is used to provide the most efficient beam pattern at different beam angles relative to the region or volume of interest being scanned. Thus, a first pattern can utilize that illustrated in FIG. 8A, which is than switched to a second pattern for a different scan angle. This can involve selecting a transducer element within a neighborhood 880 surrounding a given element to scan at a second angle.

The primary goal of the optimization method is to minimize the average side lobe energy. Specifically, this is done by interactively evaluating the optimization criterion:

$$J = \frac{1}{2u_{max}^2} \int \int_S W(u_x, u_y) B(u_x, u_y) du_x du_y, \quad (1)$$

where the weighting function, $W(u_x, u_y)$, applies more weight to regions in the array response that require side lobe reduction. The optimization method begins with no weighting (i.e., $W(u_x, u_y)=1$) and proceeds by choosing successively better weighting functions that satisfy the optimization criterion. Since the side lobes that require the greatest reduction are related to the previously computed beampattern, $B(u_x, u_y)$, the weighting is chosen such that $W(u_x, u_y)=B(u_x, u_y)$. This is done in an interactive manner until convergence.

Basically, a random array is capable of producing an imaging point spread function that has a main lobe to average side lobe ratio of N, where N is the total number of active elements in the array. For the 256-element sparse array example, the resulting ratio is −13 dB. Using a wide bandwidth approach improves this ratio by 10 dB. Based on the preceding optimization criterion, a pseudorandom placement of the array elements was generated (FIG. 8A).

Figure 8B:
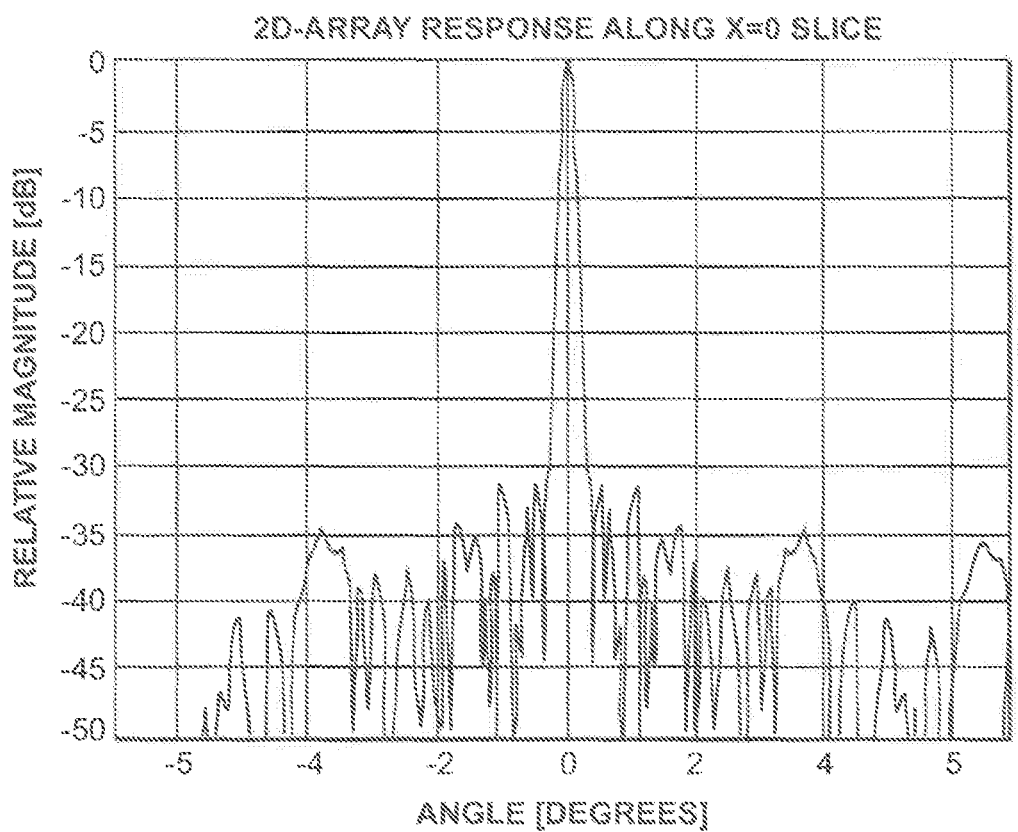
FIG. 8B graphically illustrates the sparse array performance.

FIG. 8B is a plot of the array performance, sensitivity versus cross range, for a 256-element sparsely-sampled array at 3 MHZ. The peak to maximum side lobe level is approximately 30 dB. To improve this performance, the system is configured to achieve the maximum main lobe to clutter level ratio possible, which has been independently verified.

Figure 9A:
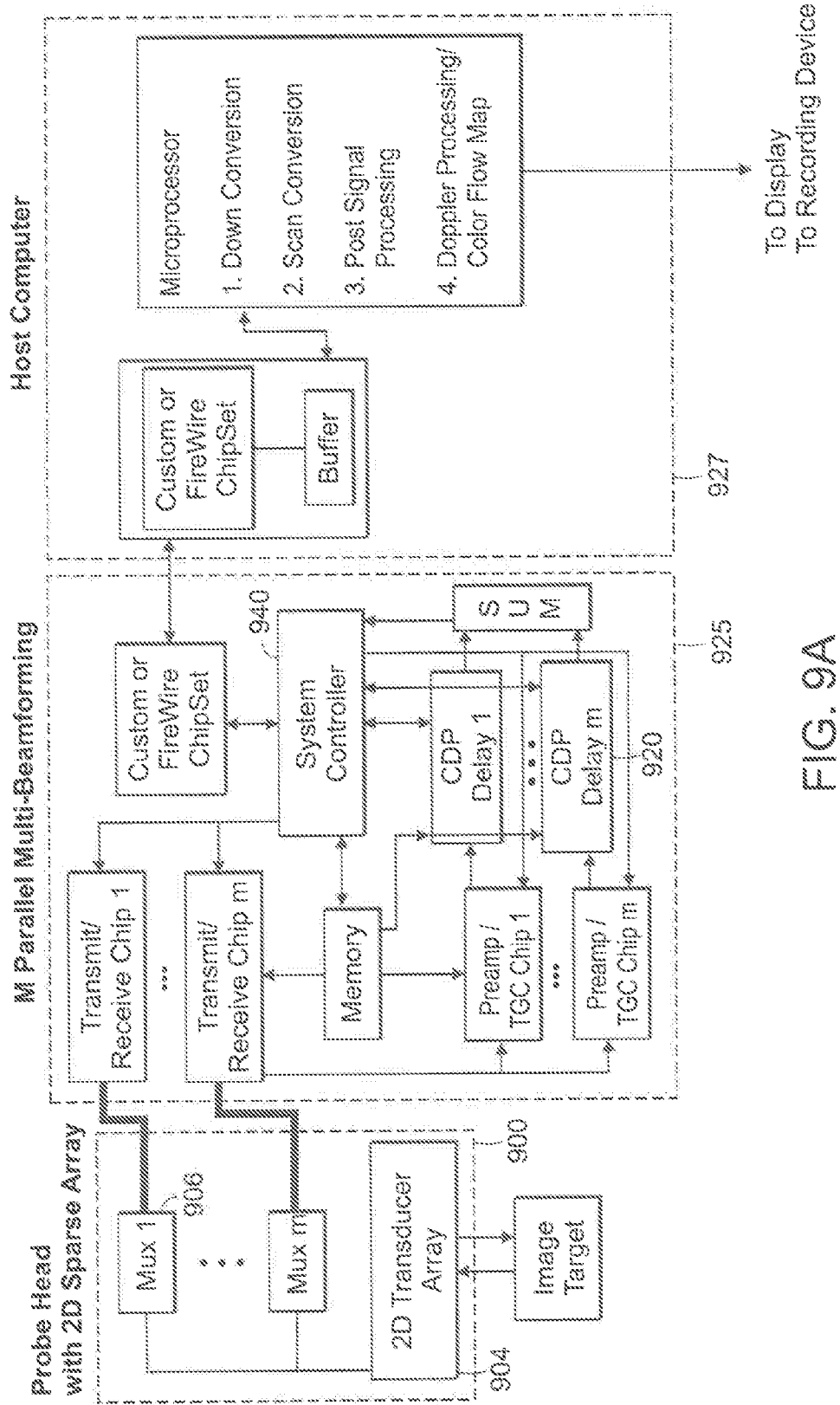
FIG. 9A illustrates the use of the integrated sparse array scan head probe of the present invention connected to a host system with charge-domain beamforming processing.
Figure 9B:
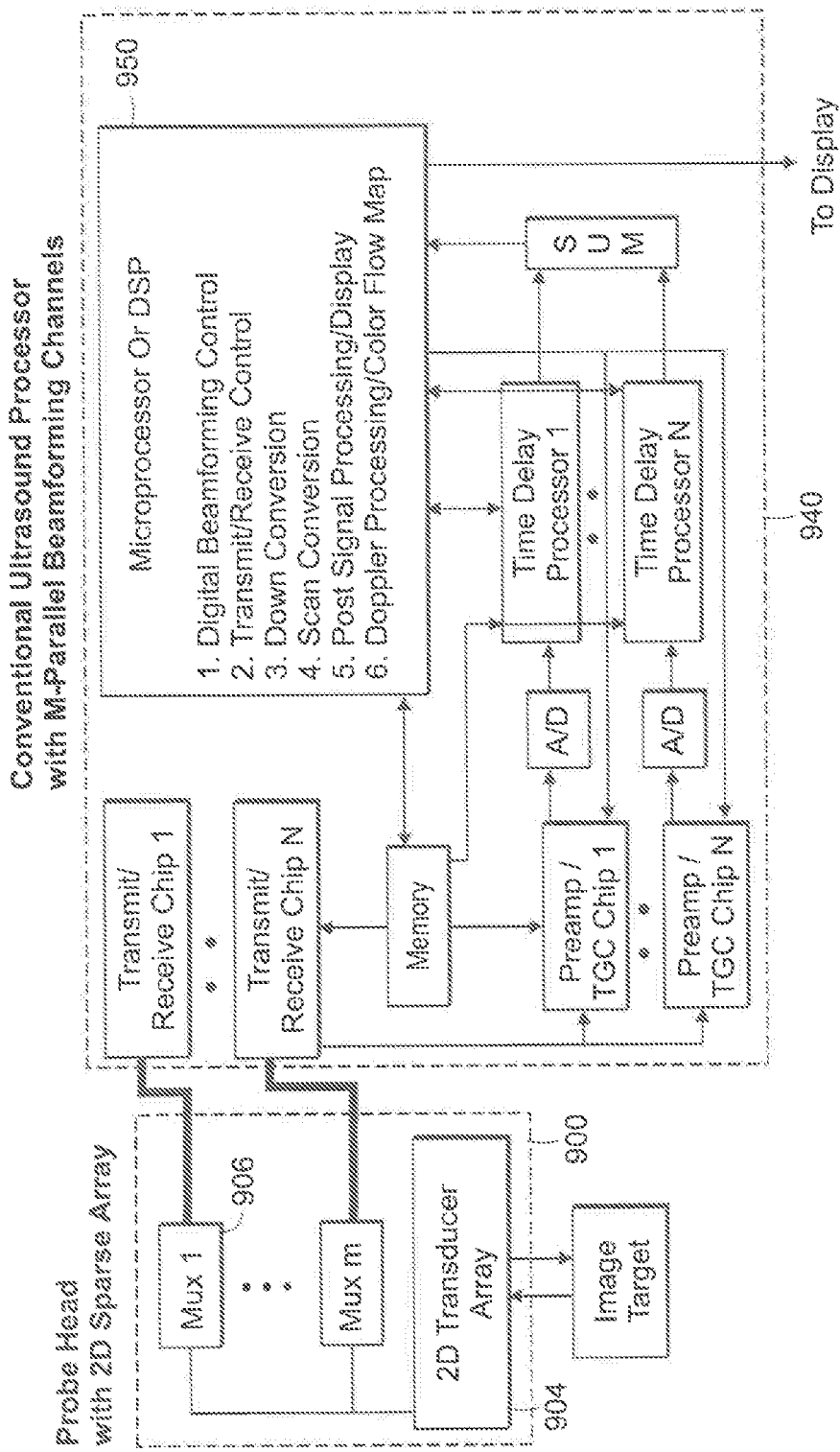
FIG. 9B illustrates the use of the integrated sparse array scan head probe of the present invention connected to a conventional digital ultrasound system with m-parallel beamforming components.

FIG. 9B depicts a system that the sparse array scan head 900 is connected to a conventional, commercially available time-domain digital ultrasound imaging system 940 with m-parallel beamforming channels. It is easy to see that in FIG. 9A, the time-delay processor can also be implemented by using CDP time-delay lines 920 in housing 925 that is connected to a separate computer 927. An array of m multiplexers 906 is used to switch between a sequence of scan patterns executed using a software program and system controller 940 or processor 950. The sequence of sparse array patterns is thus selected to scan at different scan angles of an object being imaged to provide 3D ultrasound imaging thereof.

A commercially available window-based 3D visualization software can be used to visualizing, manipulating, and analyzing the 3D multiple-beams volume image data generated by the electronically-adjustable acoustic conformal lens system. Traditionally, a clinician with 2D ultrasound images for diagnosis would look at the 2D scanned images slice by slice and mentally reconstruct the information into a 3D representation to judge the anatomy of the patient. This procedure requires the clinician to have well-founded experience as well as a highly sophisticated understanding of human anatomy. To create a "complete" image to the 3D structures, the clinician has to take all available slices into account. Looking at hundreds of slices is too time-consuming, even for a single patient. 3D visualization based on 3D volume data can help overcome this problem by providing the clinician with a 3D representation of the patient's anatomy reconstructed from the set of multiple-scanned beamforming data.

A commercially available software tool such as KB-Vol3D of KB-VIS technologies, Chennai, India, provides display or viewing 3D features such as:

Fast Volume-Rendering

Shaded Surface Display

Shaded-Surface module allows easy visualization of surfaces in the volume. Surfaces may be created by intensity-based thresholding. Alternatively, the Seeding option allows selection of specific connected structures of interest.

MIP (Maximum Intensity Projection) with Radials

MPR (Multiple-Plane-Reformatting) with Oblique & Double-Oblique and 3D correlation MPR Slabs & Multi-Cuts Curved MPR Color & Opacity Presets with Editor Region-Growing and Volume Measurements Cutaway Viewing with Slab-Volume and Interactive Real-time VOI Volume-interiors are easily visualized using the "Cutaway-Viewing" tool. A Cut-Plane is used to slice through the volume, revealing the interior regions. The cut-plane is easily positioned and oriented using the mouse.

The VOI (Volume-of-Interest) tool allows interactive, real-time Volume-of-Interest display. The user can isolate and view sub-volumes of interest very easily and in real-time, using easy click-and-drag mouse operation.

Image Save in Multiple Formats

Images displayed by KBI-Vol3D can be captured to various image formats (including DICOM, JPEG, and BMP etc.)

Movie Capture in AVI Format

Visualization operations can also be captured to an AVI movie .le and played on Windows Media Player, Quick-Time, and Beal Player etc.

Figure 10:
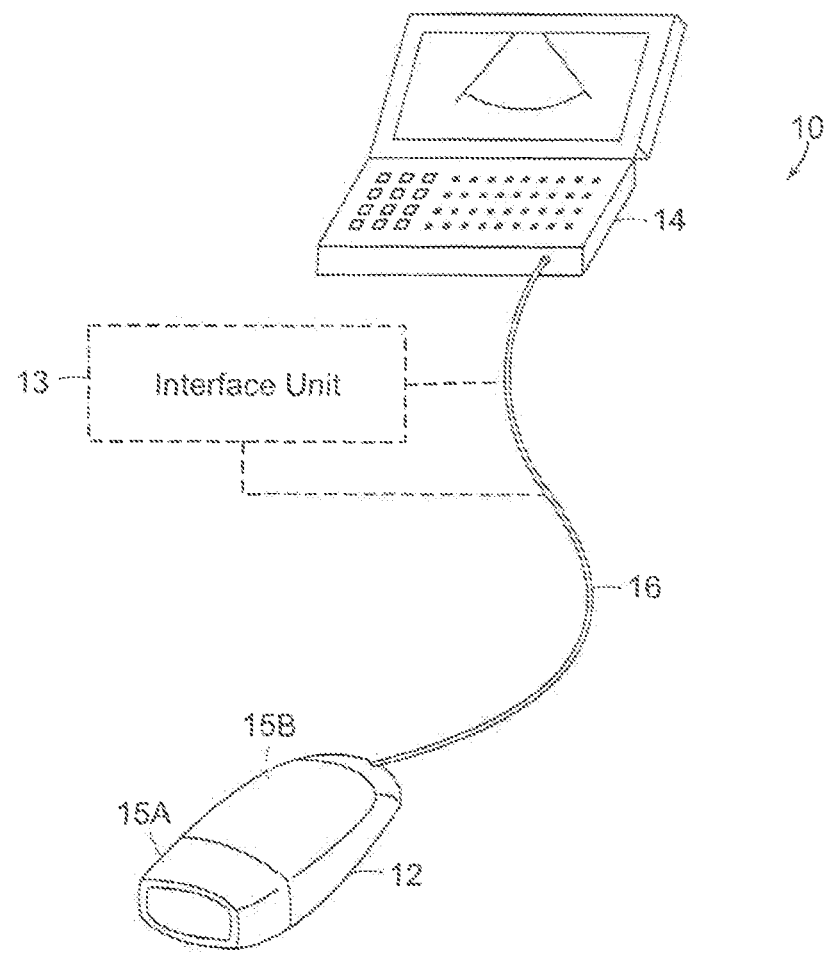
FIG. 10 illustrates a scan head connected to a portable computer in accordance with a preferred embodiment of the invention.

The invention can be implemented using a scan head 12 connected to a portable computer 14 as shown in FIG. 10. the ultrasound system 10 can also include a cable 16 to connect the probe 12 to the processor housing 14. Certain embodiments can employ an interface unit 13 which can include a beamformer device. Scan head 12 can include a transducer array 15A (2D)) and a circuit housing 15B which can house multiplexer and/or beamforming components as described in detail in U.S. Pat. Nos. 6,106,472 and 6,869,401, the entire contents of these patents being incorporated herein by reference.

A 2D array configuration using sparse-array for transmission and non-overlapped fully-populated array is used for receiving. For an N×M element array, only m-elements with optimized sparse array placement are used for transmition and then the remaining NM-m elements are used as the receiving array. For example, for a 40×60-element 2D array, 256-elements are used as transmit element, the placement of the transmit elements are optimized based on selection criteria, the remaining 2144 element are used as received elements. This embodiment simplifies the multiplexer requirement needed for a 2D array, in which case the multiplexer can be mounted in the interface housing.

Figure 11:
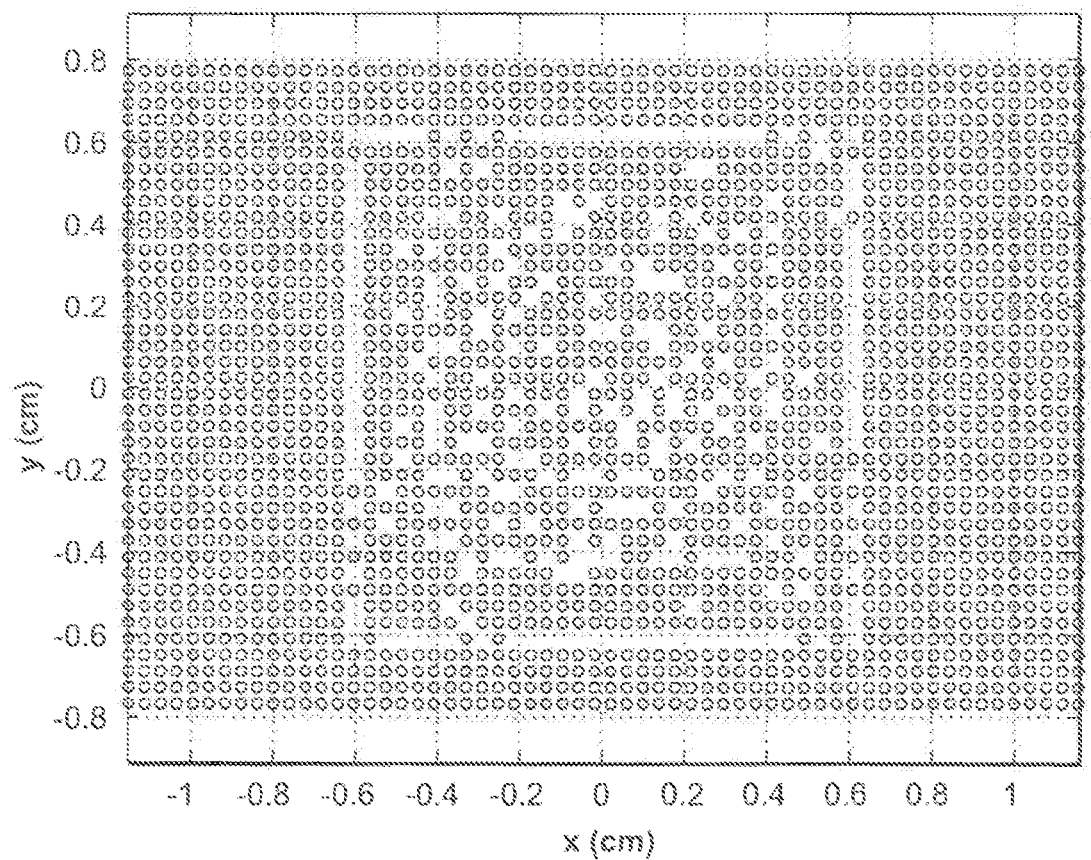
FIG. 11 illustrates a near fully populated receive array in which the receiving elements are independent of, and do not overlap, the transmit array.

An example of the element locations for the near fully-populated 40 by 60 receive array 50 is shown in FIG. 11. The 2400-element array is depopulated by the 256 sparse array transmit elements to yield 2144 receive element locations. These elements are independent and do not overlap the sparse-array transmit elements. In a preferred embodiment the transmit elements constitute less then 25% of the total number of array elements, and preferably less then 15%.

Figure 12:
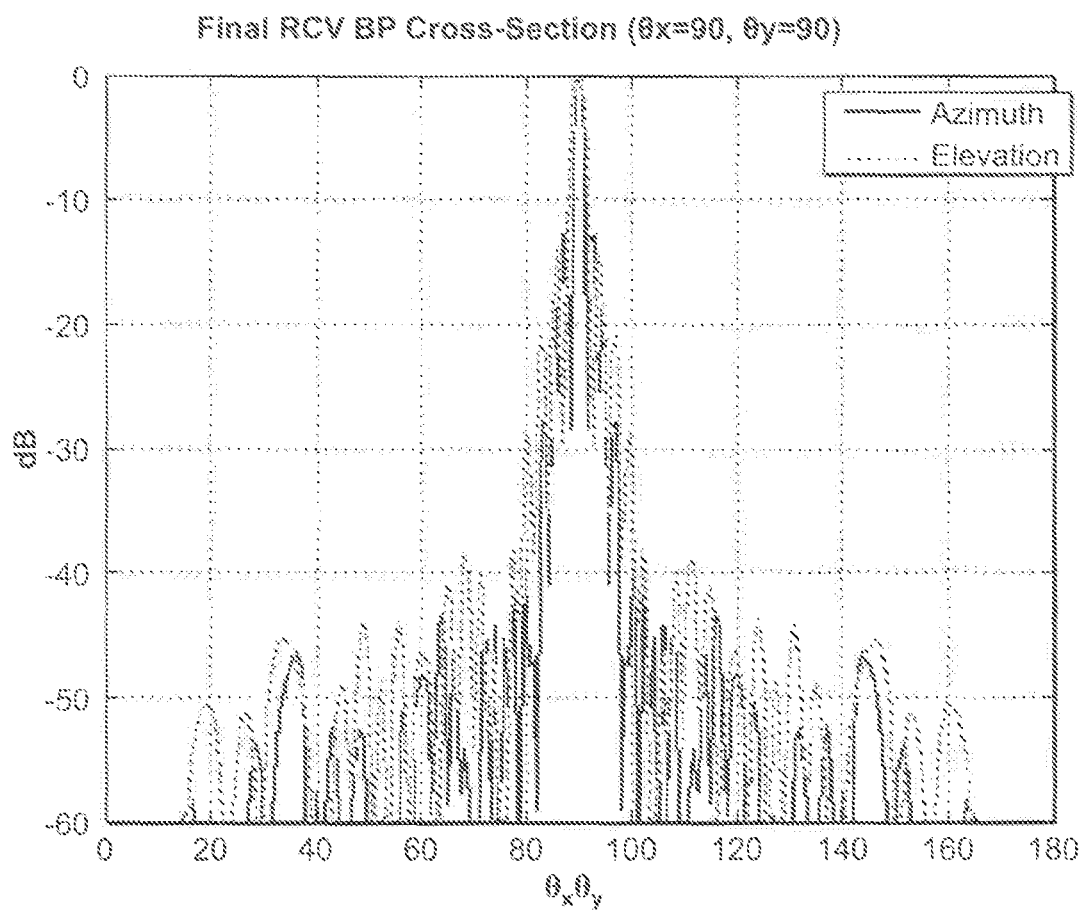
FIG. 12 graphically illustrates the azimuth and elevation cross-sections of the receive array beampattern.

The azimuth and elevation cross-sections of the beampattern of the above mentioned receive array are shown in FIG. 12. The first sidelobe is approximately −13 dB relative to the central peak. The grating lobes are less than −30 dB relative to the peak. Given that the 2D array is wider than tall, the azimuthal beamwidth (plotted in blue (solid)) is slightly narrower than the elevation beamwidth (plotted in green (dotted)).

Figure 13:
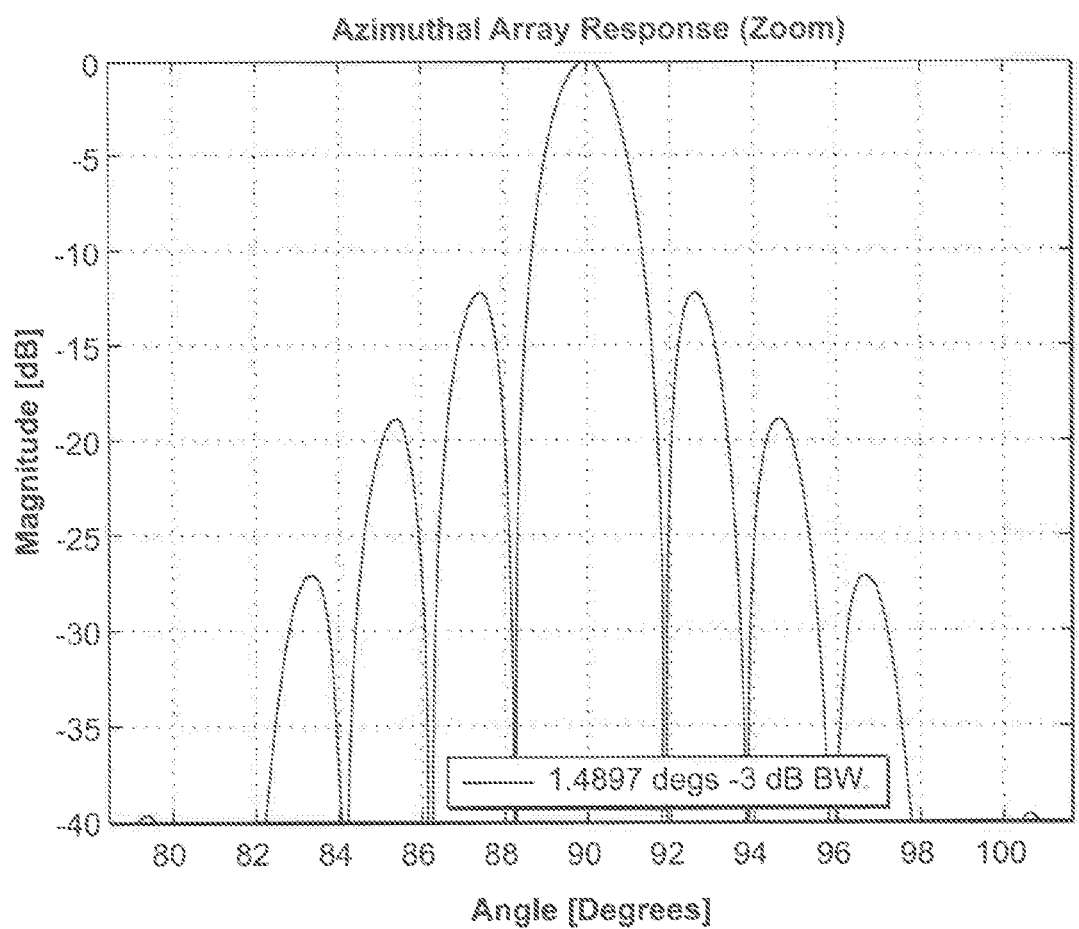
FIG. 13 is a magnified portion of the azimuthal beampattern of FIG. 12 showing the mainlobe and sidelobe structure.
Figure 14:
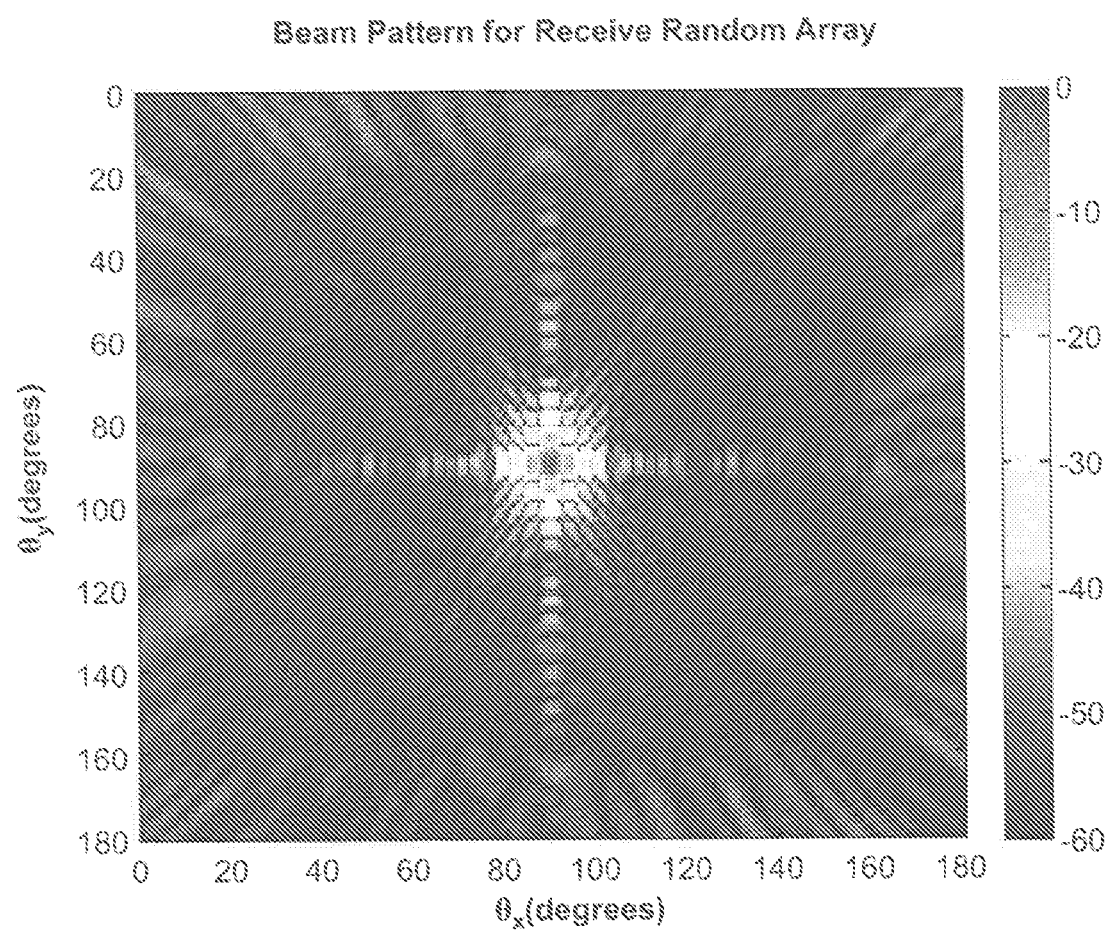
FIG. 14 illustrates a near fully populated receive array beampattern.

In FIG. 13, a magnifying view of the above mentioned azimuthal beam pattern demonstrates the detailed mainlobe and sidelobe structure. For this case, the beamwidth is approximately 1.5 degrees. The beam pattern is nearly identical to the fully populated 60×40 element beam pattern. The receive array beam pattern is shown in FIG. 14. As stated above, the received sparse array is comprised of a 2144 elements. There are no sidelobes due to depopulating the center of the array by 256 (transmit) elements.

Figure 15:
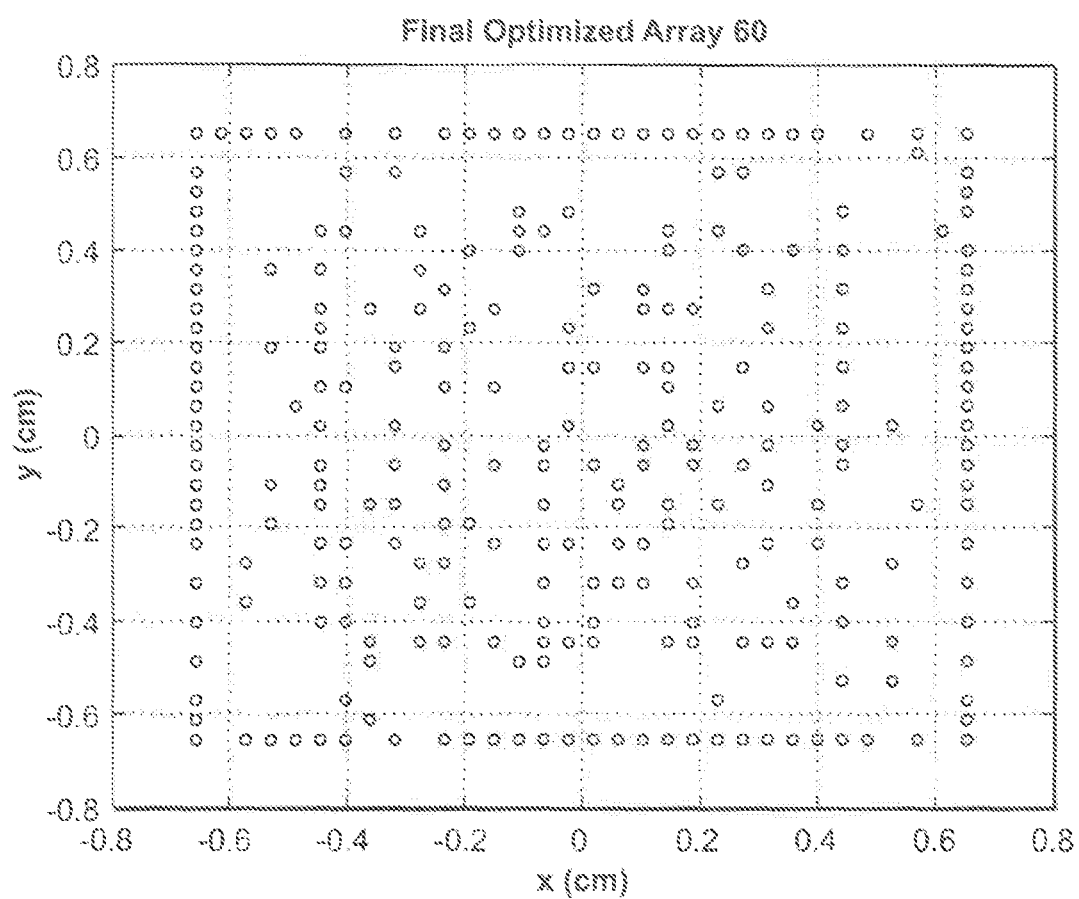
FIG. 15 shows selected transmit locations for a sparse array in accordance with the invention.
Figure 16:
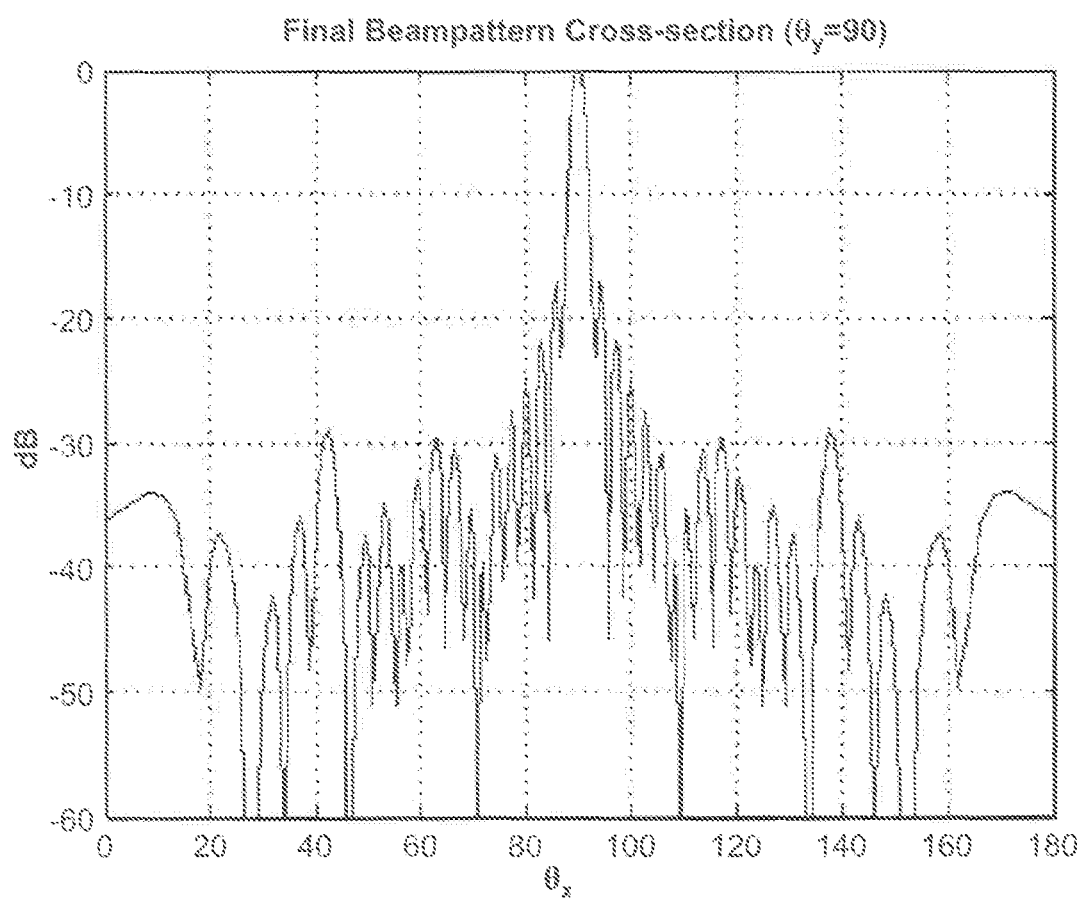
FIG. 16 illustrates a cross-sectional view of the transmit sparse array beampattern of the embodiment in FIG. 15.

An example of the final element locations for the 256 transmit sparse array 60 are shown in FIG. 15. The 256 element locations are confined to the central 32×32 elements of the fully populated array. These elements are independent and do not overlap the receive array elements. A cross sectional view of the transmit sparse array beampattern is shown in FIG. 16. The first sidelobe is approximately −17 dB relative to the central peak. The grating lobes are less than −27 dB relative to the peak. The sparse array optimization algorithm minimizes the sidelobe energy +/−45 degrees in elevation and +/−45 degrees in elevation.

Figure 17:
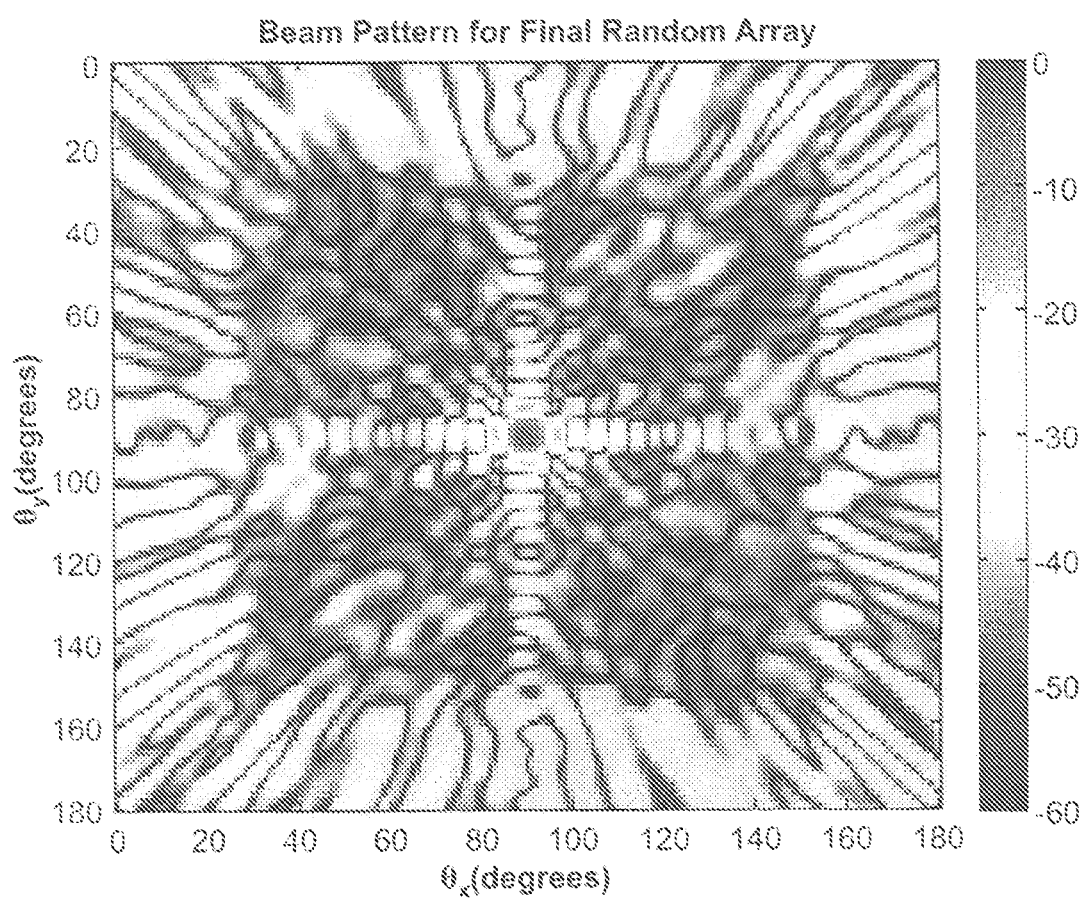
FIG. 17 illustrates a sparse transmit array beampattern.
Figure 18:
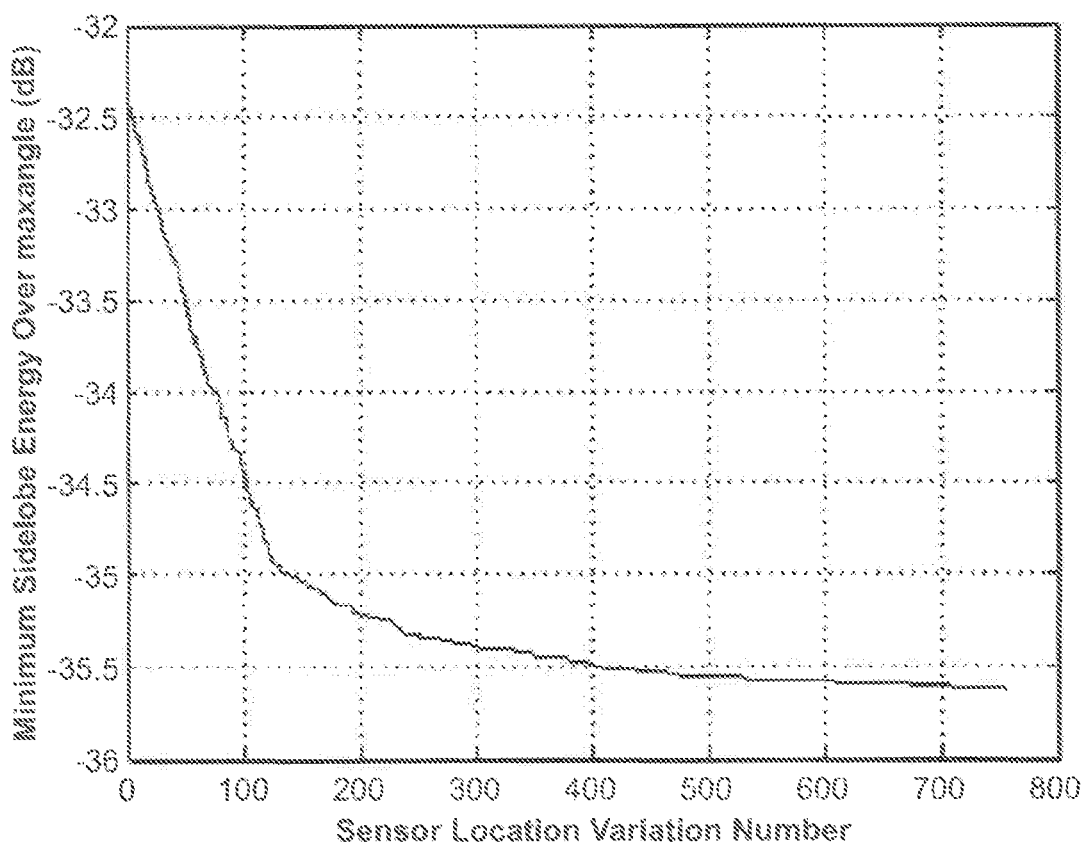
FIG. 18 illustrates that it is possible to limit average sidelobe energy to less than −35 dB relative to the central peak of the beampattern.

FIG. 17 demonstrates the beam pattern of the sparse transmit array shown in FIG. 15. The transmit beampattern is designed to uniformly cover a 4×4 beam data pyramid. The transmit sparse array is comprised of a 256-element subset of the fully populated 2400-element array (approximately 10% fill). The placement of the transmit/receive array design algorithm required over 750 iterations to minimize the transmit and receive sidelobe energy within the +/−45 degree azimuth, +/−45 degree elevation region. As shown in FIG. 18, after 750 iterations, the final sparse transmit-array element locations limit the average sidelobe energy to less than −35 dB relative to the central peak of the beampattern.

A low-power ultrasound system capable of electronically scanning a two-dimensional, 2D, matrix array to generate real-time three-dimensional, 3D, volumetric images with 64 by 64, 4096, scanning beams at a greater than 20 3D images per second is described. For each transmit pulse, the system is capable of generating 16 received beams. In addition, the design is able to drive a one and one-half dimensional array and also support wide-bandwidth encoded transmit waveform for pulse compressing to improve the system sensitivity. Wide bandwidth enables the use of chirped or coded waveforms (PN sequence) that can extend the length of the low power transmit burst without a loss of axial resolution. The combination of these features results in an imaging array with electronic systems that will fit within a portable hand-carried device.

The beamformer processing system is a time domain processor that will simultaneously process the returns of a large 2D array, the low-power; highly integrated beamformer that provide a real time processing of the entire array and will thus provide a low cost unit that can be hand carried.

There is a strong need for a real-time 3D ultrasound imaging using a 2D matrix array. In this section, the minimal number of receive beamforming channels required in an ultrasound system to support a real-time 3D imaging is analyzed. It is shown that a minimum of 192 parallel received beamforming channels is required to support a reasonable sized such as 48×64-element array.

An example of a system having an electronically-adjustable acoustic conformal lens is to divide the surface of a 2D transducer array into plane "tiles" of relatively small sub-arrays can be formed in U.S. Pat. No. 6,292,433, the contents of which is incorporated herein by reference; beamforming of the entire array can be separated into two stages, first a small-aperture subarray beamforming followed by a second stage large-aperture coherent summing of the outputs from each of the subarrays. As depicted in the tiles/subarrays can be made small enough so that when an object is placed within the field-of-view of the imaging system, the incident radiation from the object toward each "tile" can be treated using a far-field approximation. However, near-field beamforming capability has been incorporated in the actual implementation of the subarray beamforming system to allow a broader application. Additional delay elements are incorporated as second-stage processing to allow all subarrays to be coherently summed. The delay-and-sum beamformer allows each subarray to "look" for signals radiating from a particular direction. By adjusting the delays associated with each element of the array, the array's look direction can be electronically steered toward the source of radiation. The delay line requirement for each element in the sub-array can be less than a hundred stages. Only long delays for global summing are needed for the final near field focusing. A detailed diagram of an electronically-controlled beamforming system in accordance with the invention is shown in FIG. 14A of U.S. Pat. No. 6,292,433. This system consists of a tank of parallel time-delay beamforming processors. Each processor consists of two components: a 2D sub-array beamformer for small-aperture beam-steering/focusing and an additional time delay processor to allow hierarchical near-field beamforming of outputs from each corresponding subarray. As can be seen in FIG. 14A referenced above for a system with m-subarrays, m-parallel programmable $2^{nd}$-stage near field time delays are needed for individual delay adjustment to allow all m-parallel outputs be summed coherently, in turn, this summed output provides the 3D images of the targeted object.

It is easy to understand that, without using this hierarchical subarray small aperture and then large aperture beamforming approach, for an 80×80 element 2D array, a cable consisting of six thousand and four hundred wires is needed to connect the transducer array to a conventional beamforming system. As shown in FIG. 14A of U.S. Pat. No. 6,292,433 referenced above, the number of inputs to each subarray processor equals the total number of delay elements in the subarray, each sub-array only has a single output. That is to say, the number of inputs to a subarray equals the number of transducer elements associated with that subarray. The number of subarray outputs equals the total transducer array element number divided by the number of subarrays. For example, if one selects to use a 5×5 subarray to implement this hierarchical beamforming system, after the first stage subarray beamforming, the total number of wires needed to connect to the $2^{nd}$ stage near-field beamforming is reduced by a factor of 25. More specifically, as mentioned above, without using this 2D subarray beamforming, 6400 wires are needed to connect an 80×80 2D transducer array to a conventional back-end beamforming. Using a 5×5 subarray processing bank first, the number of wires required to connect to the backend beamforming system is reduced to 256. Based on this example of the invention, a bank of 256 5×5 element subarrays beamformer can be integrated with a 80×80 element 2D array in the scan head, so a cable consisting of 256 wires is adequate to connect the integrated scan head with the back-end near-field beamforming system.

It is important to note that 5×5 subarray small-aperture beamforming processors can be easily integrated in a small size silicon integrated circuit, eight of such 5×5 subarray beamforming can be integrated on one integrated circuit. Note that subarrays have generally between 9 and 64 transducer elements corresponding to a 3×3 subarray up to an 8×8 subarray. The preferred range is at or between 4×4 and a 6×6 array for a square array geometry. Rectangular subarrays can also be used preferably either 3×4, 4×5, or 4×6. Note that a ¼ λ error minimum criteria is uses. Only 32 integrated circuit devices need be incorporated into the scanhead, it can reduce the cable size from 6,400 wires down to 256 wires. Similarly, for a 64×48 element 2D array, using a 4×4 subarray processing bank in the transducer housing first, the number of back-end beamforming channels is reduced to 192.

In the present invention, preferred embodiments for a 2D array beamforming, each minimizing noise and cable loss with improved signal to noise ratio performance, are described in FIGS. 4-6B. In these embodiments, the bank of in parallel subarray beamforming processors are integrated with the 2D transducer array to create a compact, low-noise, scan head. FIG. 4 depicts a system that the compact scan head is connected to a dedicated processing module, in which the m-parallel preamp/TGCs, transmit/received chips and the $2^{nd}$ stage time delay processing units are housed. This dedicated processing module communicates with a host computer 540 via FireWire, USE or PCI bus. Control and synchronization is preformed by the system controller located in the processing module. FIG. 5 depicts the same architecture as stated in FIG. 4, except, inside the dedicated processing module, the $2^{nd}$ stage time delay processing units are specifically implemented by using Charge-Domain programmable time-delay lines. FIGS. 6A and 6B depicts a system that the compact scan head is connected to a conventional, commercially available time-domain digital ultrasound imaging system with m-parallel beamforming channels. It is easy to see that in FIGS. 6A and 6B the time-delay processor can also be implemented by using CDP time-delay lines.

In a preferred embodiment of the system a large-aperture beamforming system is incorporated into the main processor housing of the ultrasound imaging system as shown in connection with FIGS. 19-24B.

The speed of sound in tissue is about 1500 cm/sec so that the round-trip propagation time for a sound wave penetrating a 15-cm depth is about 20 microseconds. For a real-time 3D imaging, at least 64×64 scanning beams at a frame rate greater than 20 3D volumetric images per second are needed to provide diagnostic quality images. For each transmit beam, the real-time 3D imaging system has to be able to form at least 16 beams for each transmit pulse to support the preferred 3D frame rate requirement. In this section, both a serial time-multiplexed beamforming and a parallel simultaneous time-domain beamforming implementation are addressed.

To achieve a 16 beam scanning requirement, a combination of serial and parallel architecture can be used, i.e., the system can use front-end time-multiplexed serial beamforming elements technique to form two beams, then followed by 8 parallel beamforms at the back-end processor, or the system can form 4 serial beams, for each serial output beam, the back-end processor then forms 4 parallel beams, and so forth.

By systematically varying beamformer delays and shading along a viewing angle of a 2D transducer array, returned echoes along the line of sight representing the 3D radiation sources can be used to create the scanned image at the scanned angle. The system can provide continuous real-time large area scanned images throughout a large field of view at 20 frames/s or more. As shown in FIG. 7, in a CDP beamforming chip, a time multiplexed computing structure can be used to generate multiple beams, i.e., for each transmit pulse, the bank of 2D subarrays and its corresponding $2^{nd}$ stage near-field time-delay line are capable of providing multiple beams sequentially. The computing circuits sequentially generate the delays required for forming K beams. The device operates using the following sequence: once a set of sampled returned-echoes are loaded in the delay lines, at time $t_1$, the delays required for forming beam 1 are computed within each module and applied in parallel to all delay lines. The sampled return-echoes with proper delays are coherently summed to form the first beam. At time $t_2$, the delays required for forming beam 2 are computed within each module and applied in parallel to all delay lines. The sampled return-echoes with proper delays are coherently summed to form the second beam. The procedure repeats until the Kth beam is coherently formed.

For example, if a computing circuit with 16-serial addressable outputs is incorporated with the processor subarray and the $2^{nd}$ stage time delay lines, for each transmit pulse, 16 beams or scan lines each along a different scan angle can be created. For 256-pulses with a down-range depth of 15 cm, the system can generate a 4096-beams with a 64×64 pixel resolution at a frame rate of 20 frames/s. The system is fully programmable; the beamforming electronics can be adjusted to zoom-in to a smaller field-of-view for high-resolution or higher frame rate images. For example, using 192-transmit pulses with the same down-range depth of 15 cm, the system can generate a 3072-beams with a 64×48 pixel resolution at a 30 frame/s frame rate.

The objective of a beamforming system is to focus signals received from an image point onto a transducer array. By inserting proper delays in a beamformer to align wavefronts that are propagating in a particular direction, signals arriving from the direction of interest are added coherently, while those from other directions do not add coherently or cancel. The time-of-flight from the radiation source to the focal point can be calculated and stored in memory for every channel from multiple directions of arrival in parallel. In a conventional implementation, separate electronic circuitry is necessary for each beam; for a multi-beam system, the resulting electronics rapidly become both bulky and costly as the number of beams increases. For example, beamforming for a linear 192 element array requires 192 parallel delay lines each with a programmable delay length of greater than 128λ. To form four parallel beams, for example, a total of 768 programmable long delay lines are required. To simplify the required electronics for multiple beams, a hierarchical two stage beamforming system is described.

Figure 19:
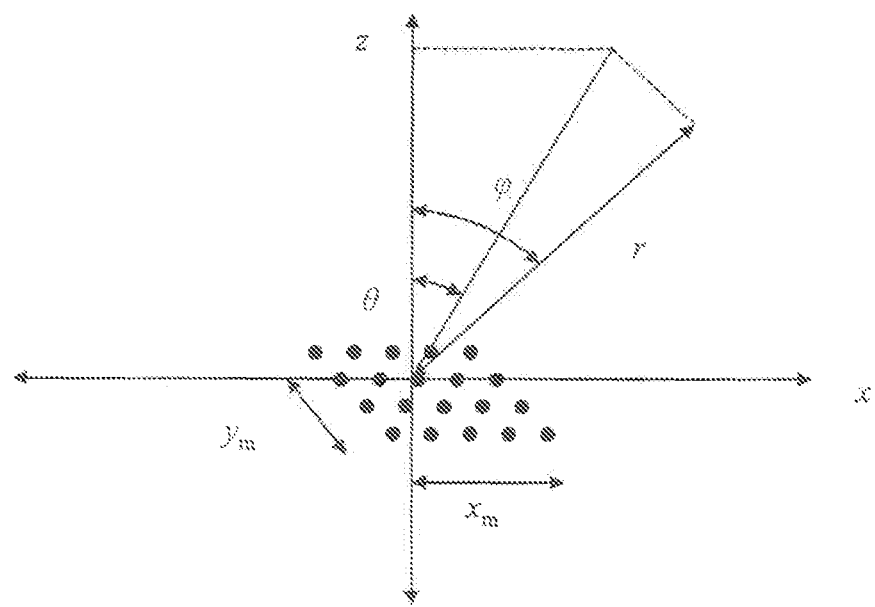
FIG. 19 illustrates the 2D differential delay equation.

The concept of hierarchical beamforming is to separate the time-of-flight calculation into two parts: the first part is a short delay for coarse-resolution, small aperture beamforming, followed by a long delay for fine resolution, large aperture beamforming. Shown in FIG. 19 is the 3D differential delay equation for a 2D array. This equation represents differential delay at array element ($x_m$, $y_m$) as a function of range and angles Theta and Phi (relative to the center of the 2D array). The equation can be reduced to a 1D array by setting all of the y=(y coordinates of the element locations) to 0. The differential delay can be constrained to a single plane (instead of a volume) by setting angle Phi=0.

Figure 20:
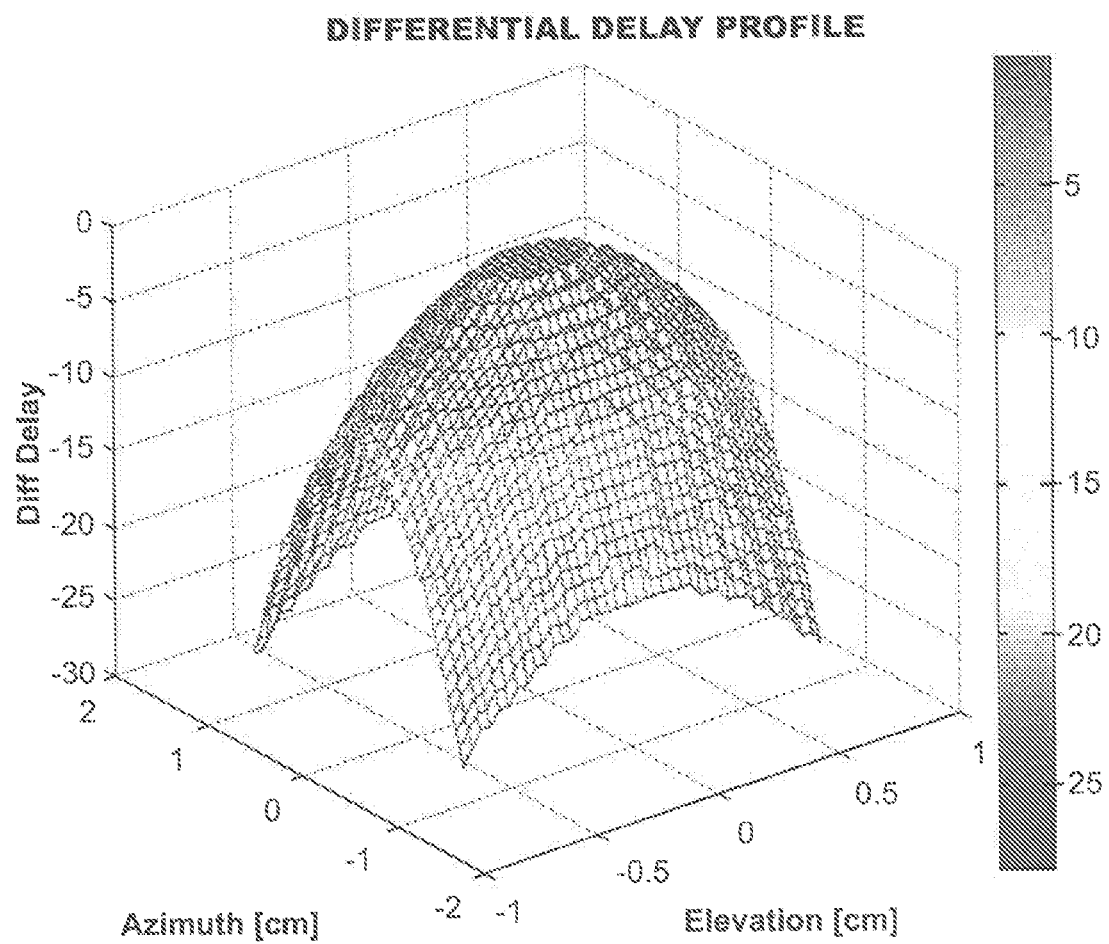
FIG. 20 illustrates a differential display profile.

To exemplify operation of a two-stage delays, a differential delay profile must be generated for all elements in the 1D or 2D array. To do this, the differential delay equation is calculated and all of the differential delays as a function of angles Theta and Phi, at a given range, are tabulated. For example, as shown in FIG. 20, the differential delay profile is plotted for an element near the center of a 2D array.

Figure 21:
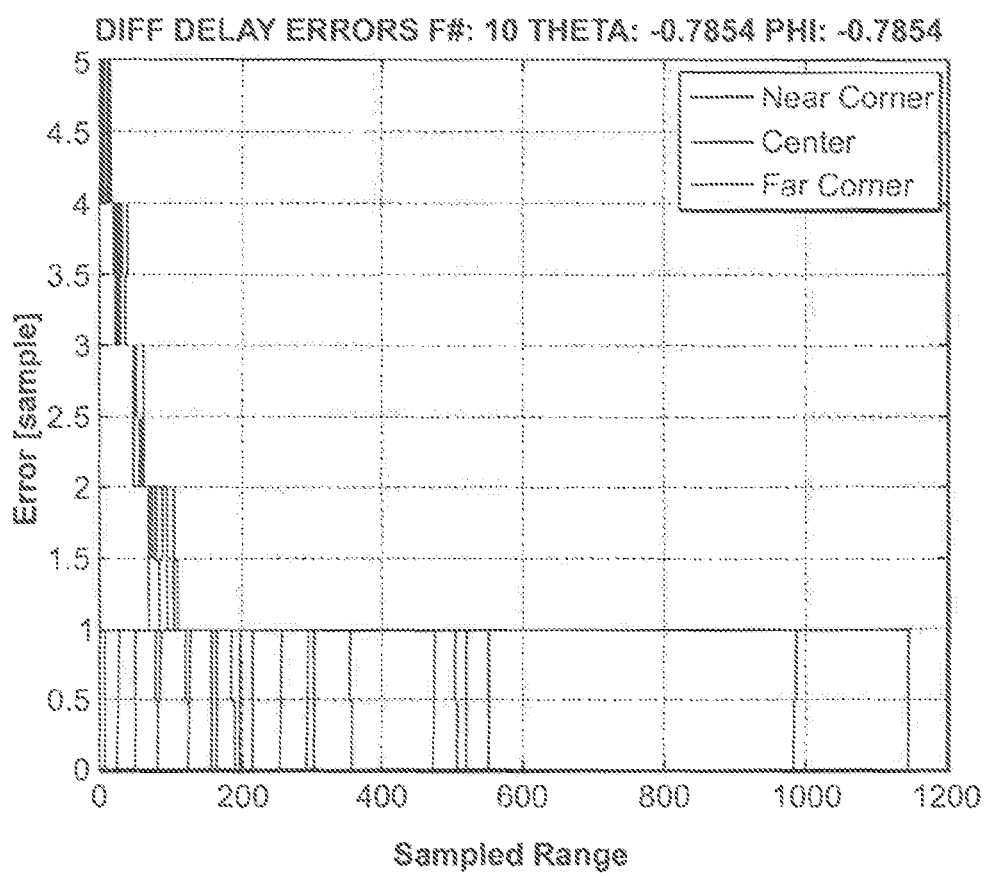
FIG. 21 illustrates differential delay errors.

In a 2 stage delay system, the tabulated data from the preceding step are broken into a coarse delay and a fine delay. To determine how to partition the coarse delay and the fine delay, the maximum differential delay errors constrained (typically set to have a maximum differential delay error less than or equal to 1 sample). The tabulated delays (from the preceding step) are also used to determine when a receive element is enabled. For example, FIG. 21 depicts the differential delay error as a function of range for a few elements. The worst case differential delay (the data plotted in blue) is for an element in the corner of a 2D array (Theta=+45 degs, Phi=+45 degs) attempting to receive image data from the direction Theta=−45 degs, Phi=−45 degs. For this case, the maximum differential delay is greater than the constraint (>1 sample error); therefore, the element would not be enabled to receive until a range greater than approximately 100 samples.

Figure 22A:
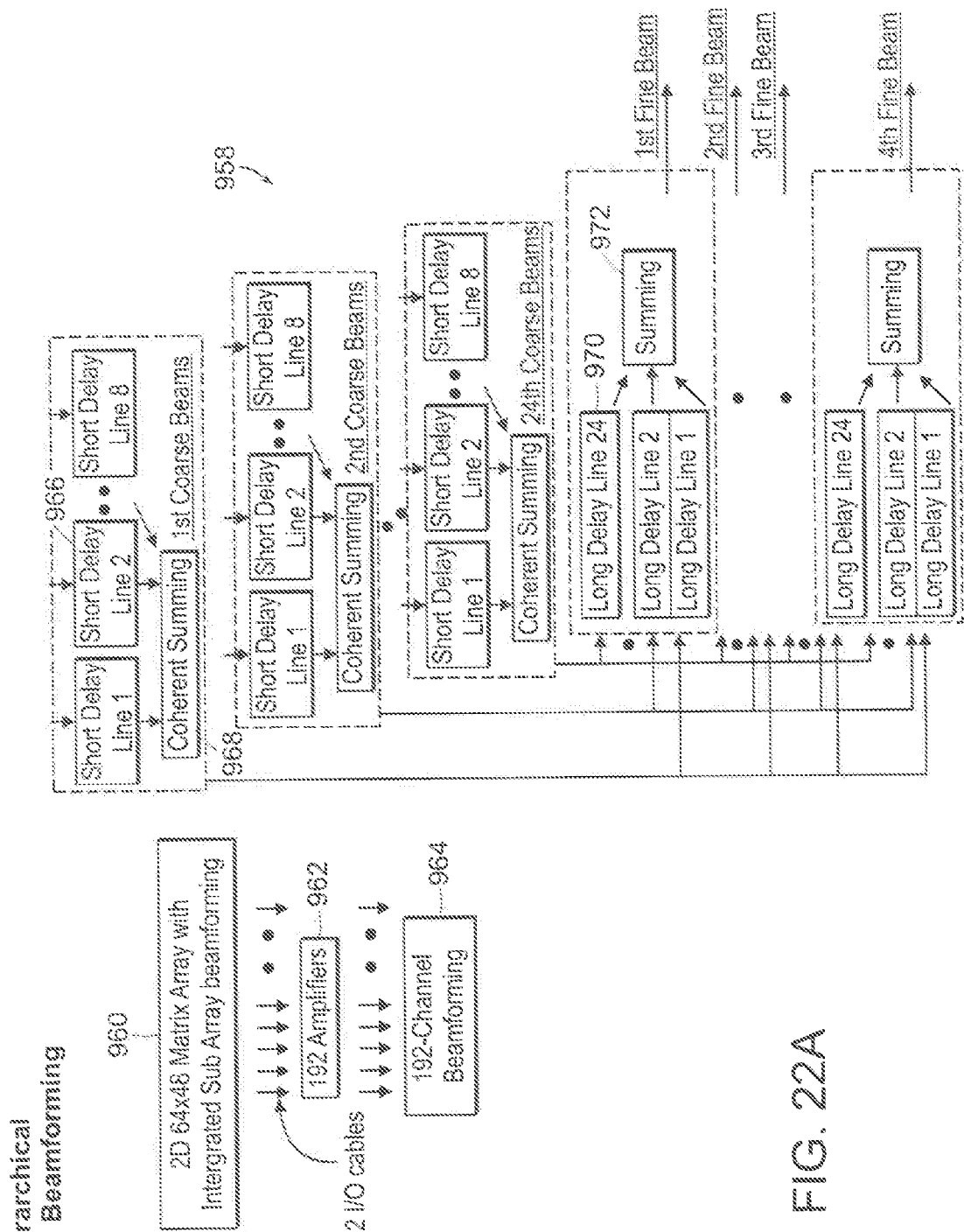
FIGS. 22A-22C illustrate embodiments of system processors in a four parallel beamforming system.
Figure 22B:
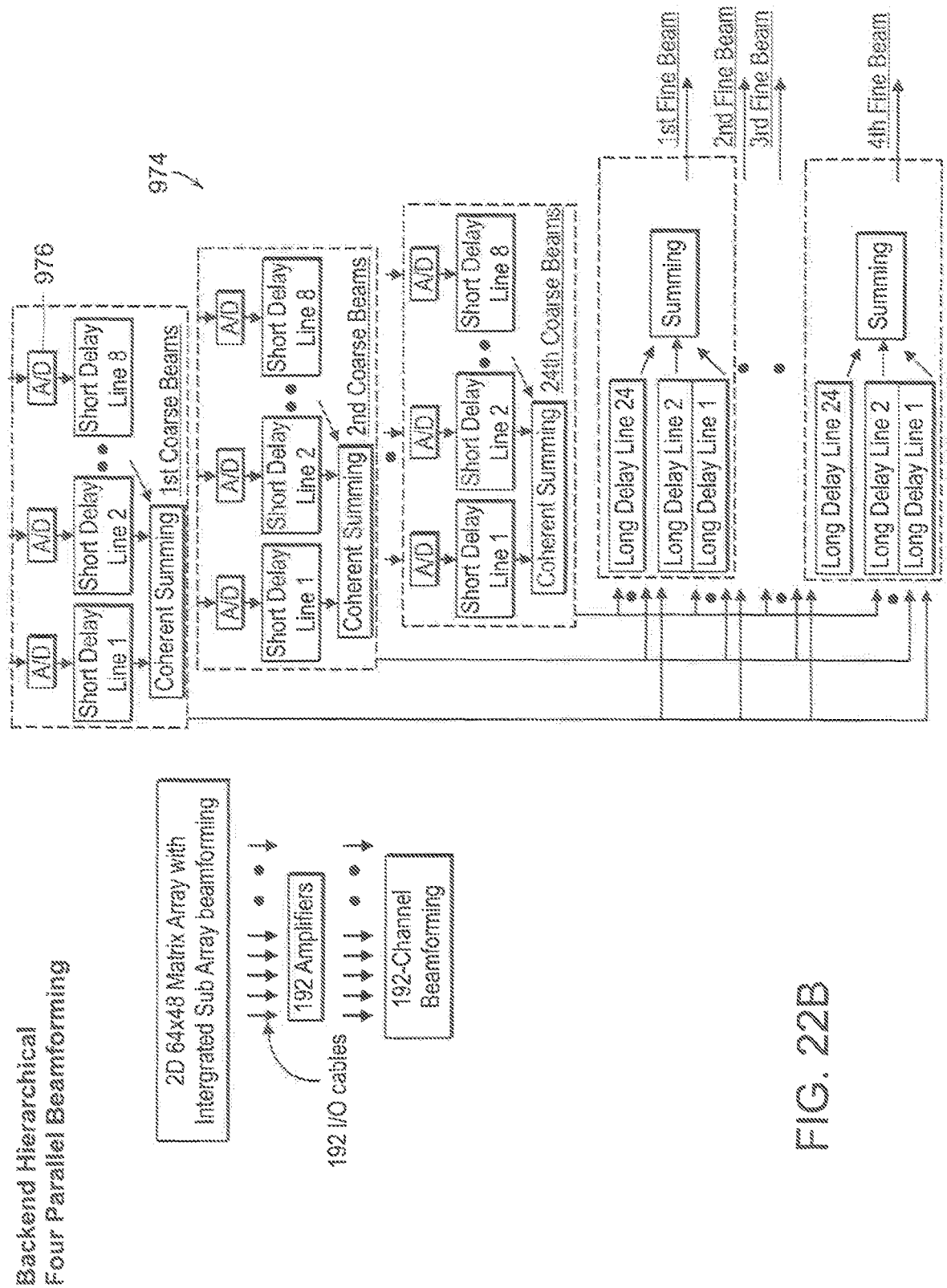
Figure 22C:
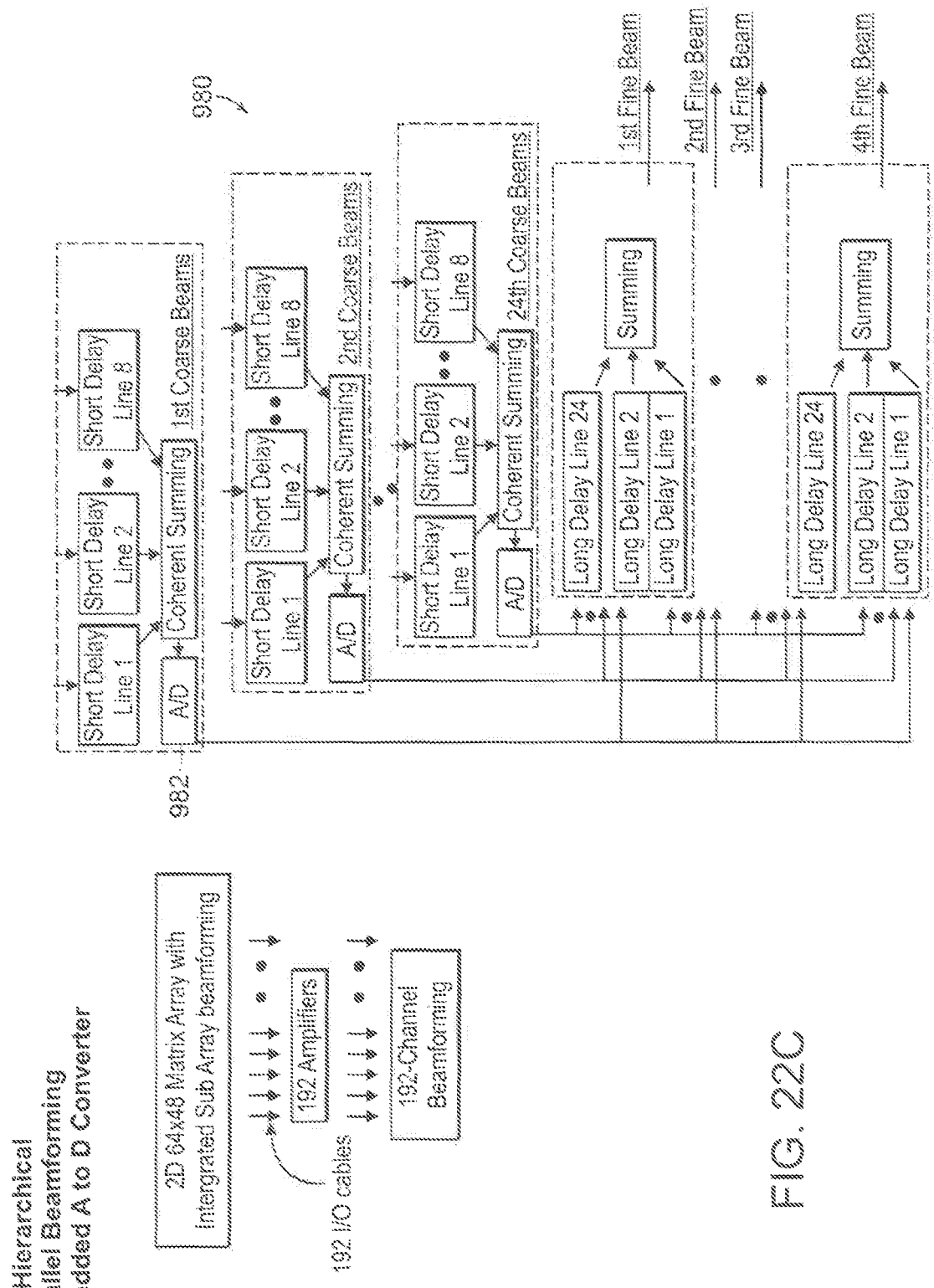

A block diagram of an hierarchical two-stage parallel beamforming system 958 is shown in FIG. 22A. A two dimensional transducer array 960 of a handheld probe, such as 12 in FIG. 10 weighing less than 15 lbs, can be coupled to amplifier 962 before being connected to the input of the beamforming system 964. The beamforming system can comprise a plurality of short delay lines, which are coherently summed at summing circuit 968 where the output is delivered the longer delay lines 970, which are also summed at summing circuit 972. First stage coarse beamforming includes coherently summing returned echoes from a small aperture, for example, with 8 neighboring receivers in this particular embodiment. Because of the small size of the aperture, the delay length of each short delay is only about 8λ. So, for a 192 element inputs, 24 such small aperture, coarse beams are formed. Each of those 24 beams is then applied to its corresponding long programmable long delay line for a large aperture, fine-resolution beamforming. To form four parallel beams, four such beamforming structures are required. As can be seen in FIG. 22A, this hierarchical implementation to form 24 coarse beams, only 192 short delays are required, and then followed by 24 long delays, each one with a programmable delay length shorter than 128λ. For four parallel beams, only 192 short delays plus 96 long delays are needed, it offers a tremendous saving in terms of electronic components and power.

Furthermore, within each small-aperture, short-delay line, a time-of-flight control circuit is used to select the tap position output from a charge-domain processing circuit that non-destructively senses the tapped-delay line output. Each receiver has a multiplier for beam shading/apodization. Within each processor, all the multipliers share a common output. The summed charge is then applied to a matched filter to decode and to compress the returned echoes to produce an imaging pulse with a reduced signal-to-noise ration. An analog to digital (A/D) or a converter on-chip charge-domain A/D converter can be used so that hierarchical summing can be carried out digitally.

In a preferred embodiment, it is important to employ high speed digital communication connection between the beamformer output and the backend processor. As described previously, the analog returned echoes received by each transducer element is converted to a digital signal by an analog to digital converter (A/D) during signal processing. As shown in the beamformer 974 of FIG. 22B, A/D converters 976 can be used at the input of each short delay line and the time delays performed digitally. Or alternatively, as shown in the embodiment 980 of FIG. 22C, the A/D converters 982 can be used at the output of each coarse beam and the long delay can be performed digitally. The A/D conversion can be performed using available discrete components, or in a preferred embodiment, a charge domain A/D converter can be formed on the same integrated circuit with the charge domain beamformer with hierarchical summing carried out digitally.

Figures 23A, 23B:
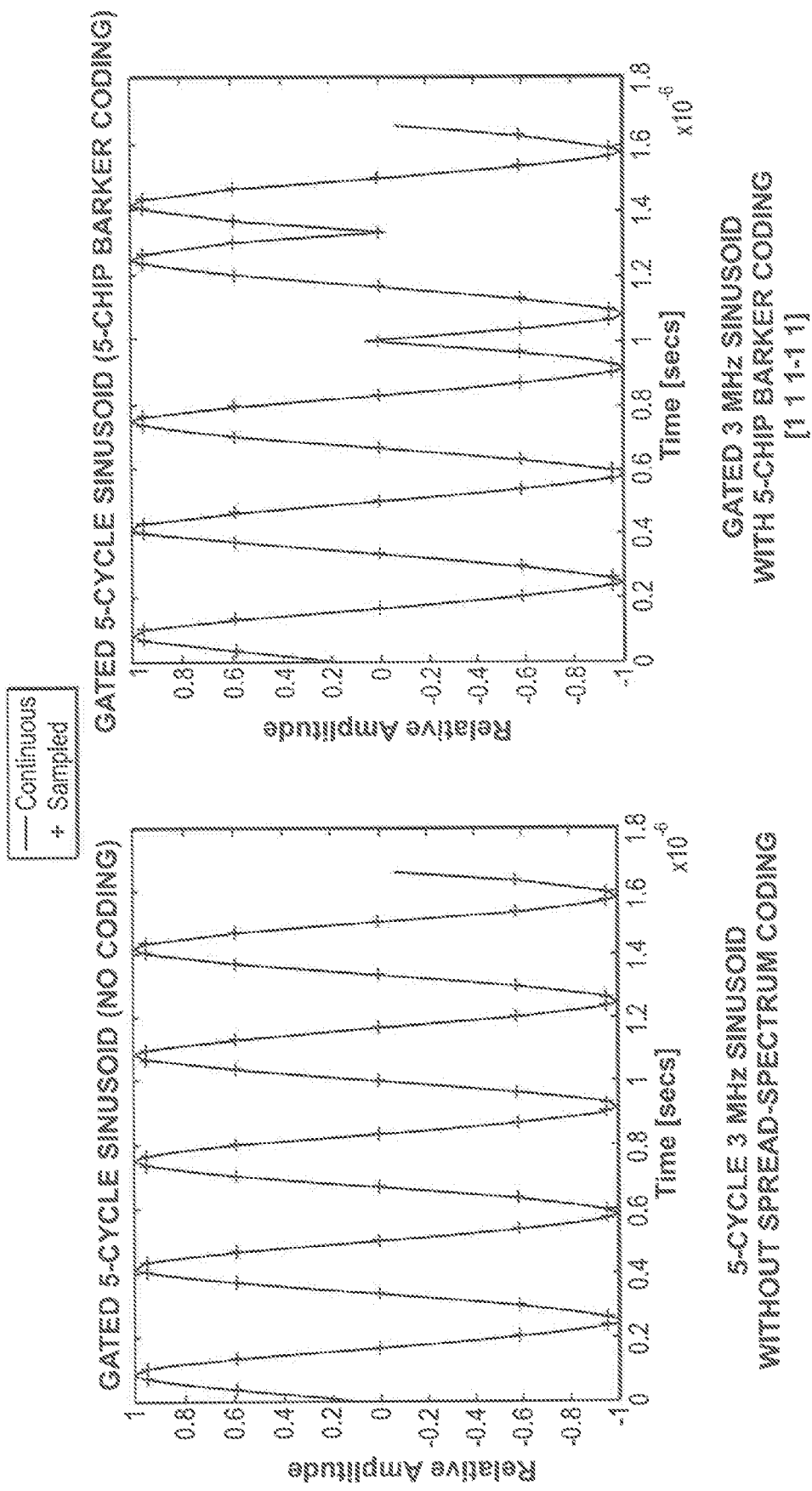
FIGS. 23A and 23B illustrated non-coded and coded transmit waveforms for spread spectrum ultrasound transmission.

The use of coded or spread spectrum signaling has gained tremendous favor in the communications community. It is now routinely used in satellite, cellular, and wire-line digital communications systems. Shown in FIG. 23A is an example of a 5 cycle 3 MHz sinusoid without spread spectrum coding. A coded or spread spectrum system transmits a broadband, temporally elongated excitation signal with a finite time-bandwidth product. The received signal is decoded to produce an imaging pulse with improved signal to noise ratio. The benefit of using coded signals in ultrasound imaging systems offers the use of high-resolution imaging while significantly lowering the peak acoustic power. These signals also provide signal processing gain that improves the overall system receiving sensitivity. Direct sequence modulation is the modulation of a carrier by a code sequence. In practice, this signal can be AM (pulse), FM, amplitude, phase or angle modulation. It can also be a pseudorandom or PN sequence that can comprise a sequence of binary values that repeat after a specified period of time.

In ultrasound, the concept of using spread spectrum/coded excitation transmit waveform comprises modulating a base sequence of transmit pulses of length P with a code sequence with a code length N. A code pulse sequence of N bursts is often referred to as an N-chip code. An example of a gated 3 MHz sinusoid with a 5-Chip Barker coding [111-11] is shown in FIG. 23B. Each "chip" corresponds to 1 cycle of the gated transmit waveform. Thus, FIG. 23B appears nearly identical to that of FIG. 23A except that the $4^{th}$ cycle is inverted. In both FIG. 23A and FIG. 23B, the continuous line represents the continuously sampled sinusoidal waveform, whereas the cross hatched points is a sampled signal, where 10 samples are taken per cycle. The coded pulse sequence, which has a length N×P, can effectively reduce the peak power in the transmitting media by spreading the power spectrum over a longer time duration. Upon reception of the spread spectrum/coded returned echoes, a pulse compression matched filter can be used to decode the received signals to produce an imaging pulse that has improved signal to noise ration (SNR). The SNR improvement of a N×P coded pulse sequence is 10 log (NP). So, for a Barker code of length 7 and a two-cycle burst transmit waveform, a SNR of 11.4 dB improvement can be achieved. However, in the present system, the transmit and received waveforms are oversampled with an over-sampled rate of S. Typically an oversampled rate of S=4 has been used. It follows then, at the receiver end, a matched filter with tap length of N×P×S can be used to decode and to compress the returned echoes to produce an imaging pulse with a SNR improvement of 10 log (NRS). In the above example, for N=7, P=2, S=4, a SNR of 17.5 dB can be achieved.

Figure 25A:
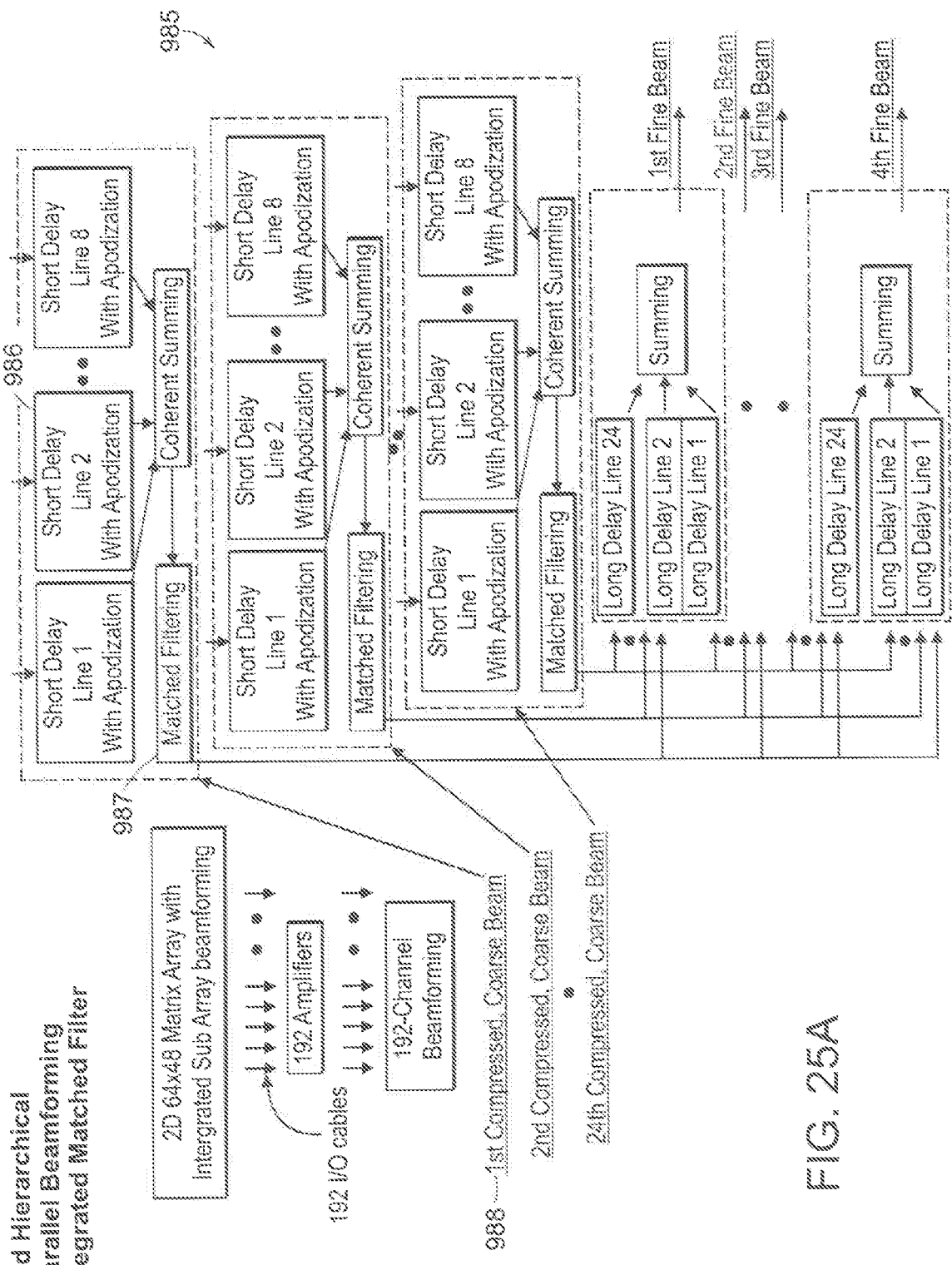
FIGS. 25A-25) illustrate preferred embodiments including a matched filter.
Figure 25B:
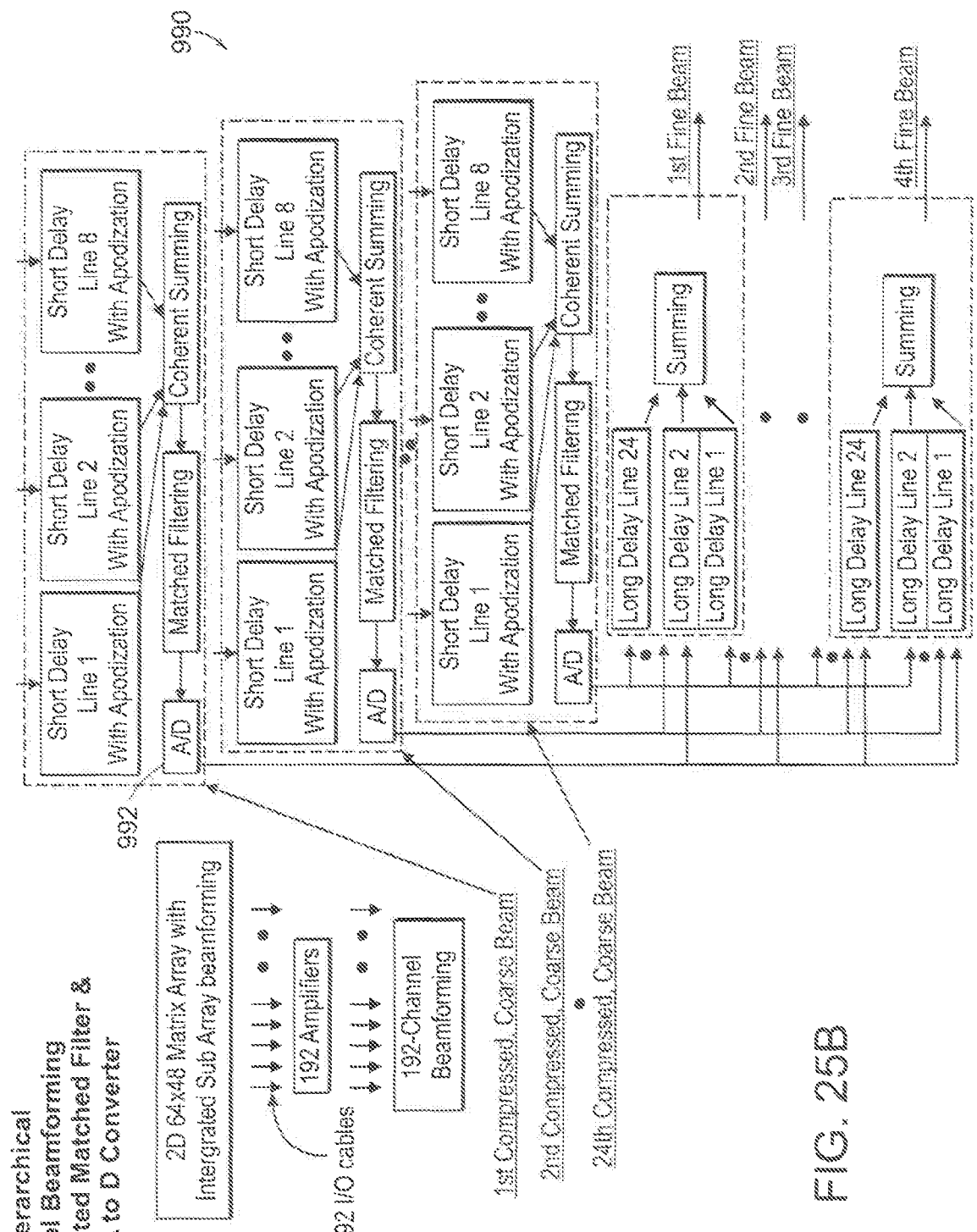
Figure 25C:
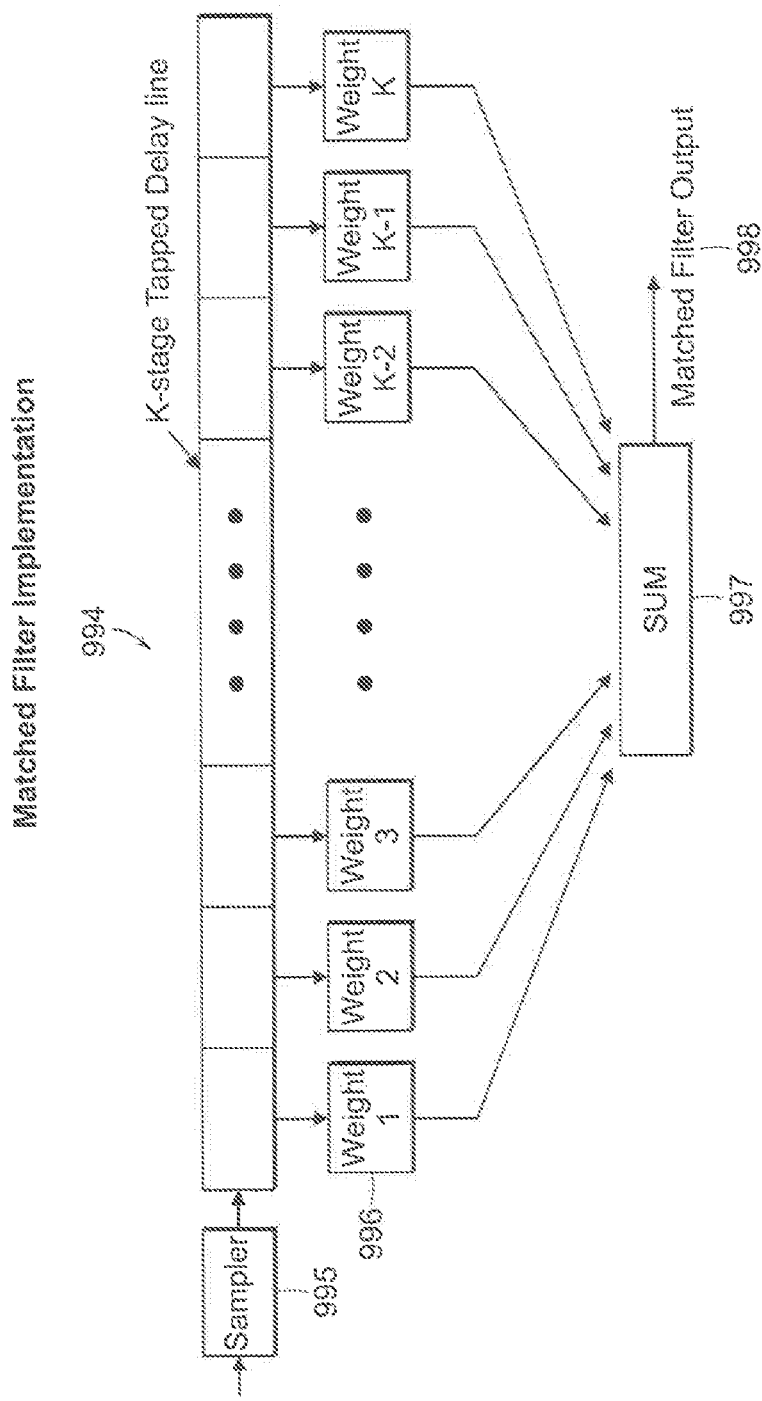

A preferred method of forming a transmission signal is shown in FIGS. 24A-24C. The base sequence is a single pulse, as can be seen in FIG. 24A. Using the 5-chip Barker code [111-11], FIG. 24B represents the convolution of the base sequence with the Barker code. Finally, the system transmits an oversampled version of the continuous waveform, as shown in FIG. 24C, a 6-times oversampled waveform is used as transmitted wave from A 192 channel receive beamforming system capable of forming four parallel, compressed beams for each transmitted, spreaded coded excited waveform is shown in the beamformer system 985 of FIG. 25A. In this implementation, a two-stage hierarchical beamforming architecture is used, first a small aperture short delay beamformer 986 output signals that are coherently summed return echoes from 8 adjacent transducers, a pulse compression matched filter 987 is then followed to decode the received signal, this compressed signal 988 is then applied to a long delay line to complete the beamforming requirement. In system 990 of FIG. 25B, an A/D converter 992 is incorporated at each of the matched filter outputs. It follows then the long delay will be carried out digitally, using a second stage digital delay line implementation.

A matched filter implementation is shown in FIG. 25O. The filter 994 consists of a K-stage tapped delay line receiving signals from sampling circuit 995 and K programmable multipliers. The spreaded, coarse beamformed signal, $f_n$, is continuously applied to the input of the delay line. At each stage of the delay, the signals can be non-destructively sensed and multiplied by a tap weight 996, $W_k$, where k=1, 2, 3, . . . , K-2, K-1, K. The weighted signals are summed together with summing circuit 997 to create a compressed output $g_m$ 998. It can be seen that, at time t=n, $$g_n = f_{n-1}W_1 + f_{n-2}W_2 + f_{n-3}W_3 + \ldots + f_{n-K-2}W_{x-2} + f_{n-K-1}W_{k-1} + f_{n-K}W_K$$

Figure 25D:
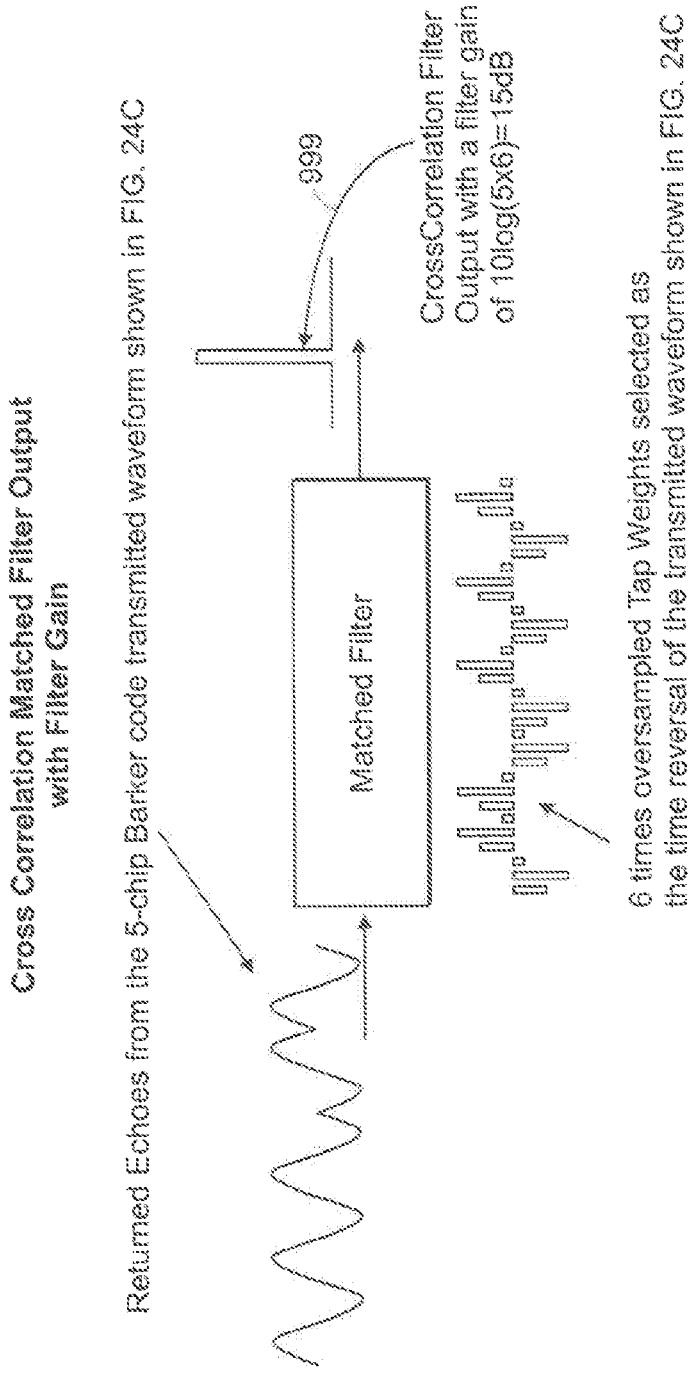

Using the example shown in FIGS. 24A-24C, if the system transmit a 6-time oversampled, 5-chip Barker code, and the weights of the matched filter are selected as a time reversal of the transmitted 5-chip Barker code excitation waveform, the matched filter produces a cross correlation output 999 that is the compressed, decoded pulsed signal (see FIG. 25D), with a filter gain of 10 log (5×6)=15 dB.

Figure 26A:
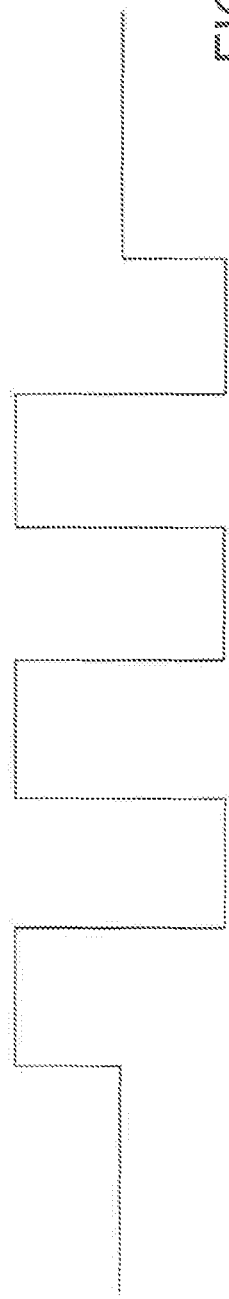
FIGS. 26A-26D illustrate a square wave signal and modified square wave transmit signals for third harmonic imaging.
Figure 26B:
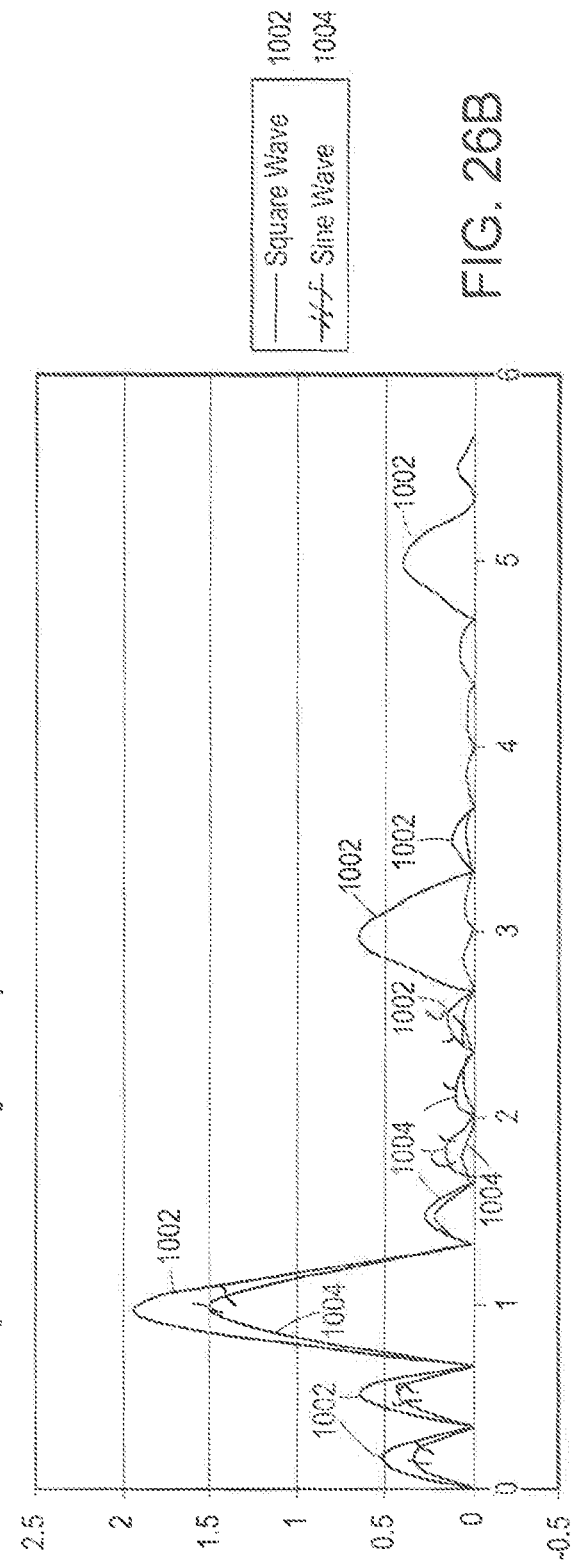

Consider an ultrasound pulser with 3 cycles of square wave, where an example is shown in FIG. 26A. The frequency spectrum of such a waveform has a third harmonic component at about 4 dB below the fundamental frequency. Shown in FIG. 26B shows a modified square wave that has been combined with a sinusoidal signal.

Figure 26C:
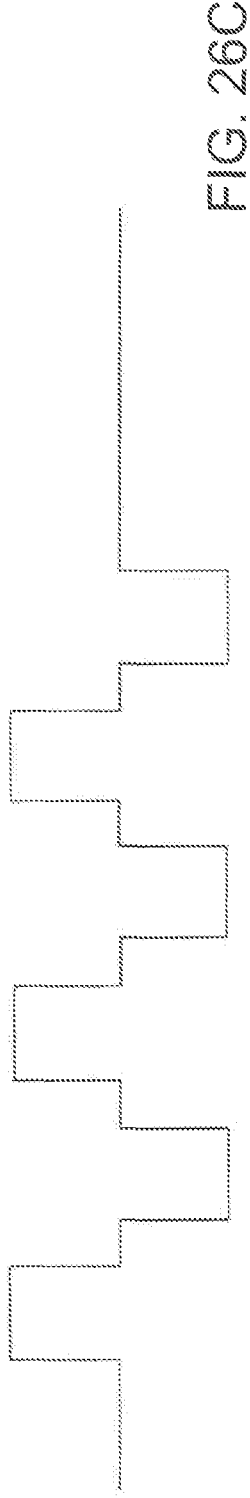
Figure 26D:
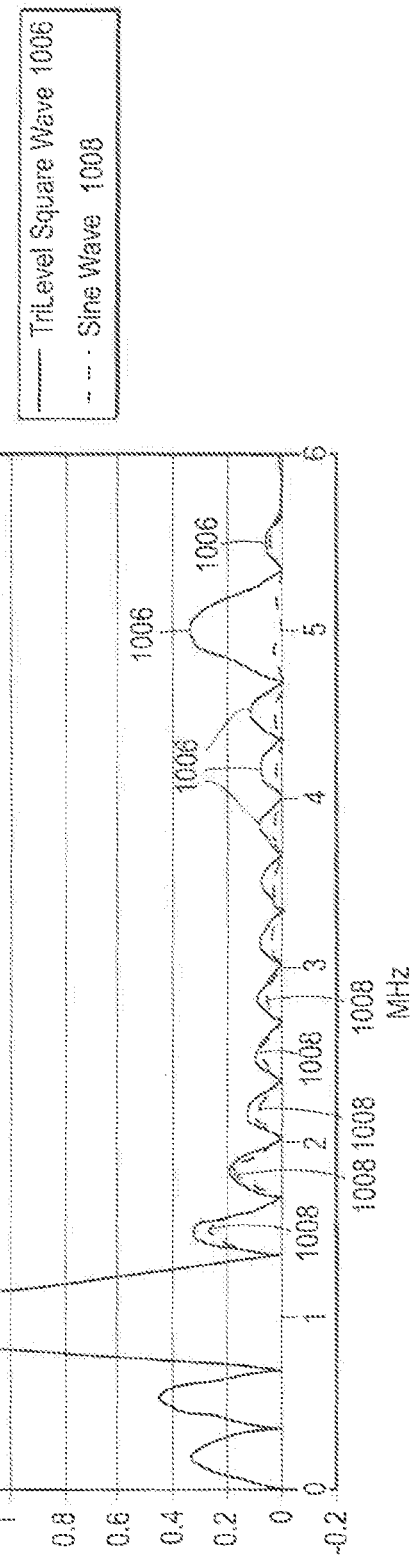

Thus a preferred embodiment of the present invention uses a modified square wave by reducing the pulse high time and pulse low time to two third of the regular square wave. This waveform has a much lower third harmonic component as the regular square wave. Shown in FIG. 26C is a modified 3 cycle square wave with pulse widths reduced to ⅔ of regular square wave. Using Modified Square Wave pulsers, a low harmonic transmitted waveform approximates a sinusoidal waveform, compared with regular square wave. This allows an ultrasound imaging system to use less expensive pulser design for harmonic imaging.

In current ultrasound system, $2^{nd}$ harmonic imaging mode has been widely accepted to image tissue and showed considerable improvements in image quality that reduces artifacts. As a result, it allows physicians to make better diagnoses in several applications compared to the fundamental excitation mode. The improvements were attributed to the effects of wave distortion due to nonlinear propagation in tissue. Current system have used the $2^{nd}$ harmonic imaging. Since the energy in the second harmonic frequency band is much lower than that in the fundamental frequency band, to increase the $2^{nd}$ harmonic sensitivity the spectral overlap between the fundamental and the $2^{nd}$ harmonic has to be minimized, however, in doing so, the $2^{nd}$ harmonic imaging resolution is reduced as a result. The higher harmonics, in particular the $3^{rd}$ harmonic, not only represent an additional important information for tissue imaging and characterization, but also has the advantage that it is easier to filter out the contribution from the fundamental frequency. Unfortunately, with the current settings of existing systems (MI, frequency), the amount of third harmonic energy returning from tissue is much less than that reflected at the fundamental frequency. It requires the ultrasound system to have excellent sensitivity and dynamic range to display the $3^{rd}$ harmonic image. Preferred embodiments of the present invention, use $3^{rd}$ harmonic imaging with coded excitation where additional gain from matched-filter processing is used to overcome the problem with weak $3^{rd}$ harmonic returns.

Two pertinent requirements for a good $3^{rd}$ harmonic coded excitation imaging are, first by, minimum $3^{rd}$ harmonic component in the transmit coded waveform, and secondly, a code selection with a $3^{rd}$ harmonic receive template that has a minimal sidelobe energy after the $3^{rd}$ harmonic matched filtering. A transmit coded waveform with minimum $3^{rd}$ harmonic component. In this section, two $3^{rd}$ harmonic templates for a Golay coded with minimum sidelobe are presented.

Golay complementary pairs (GCP) coded binary sequences are used as in this method, a complementary pairs of matched filter outputs are summed to generate impulse return with minimum sidelode $$a(z)a(z-1) + b(z)b(z-1) = 2N$$

where a(z) and b(z) are complementary pairs. As a result, no image artifacts due to match-filter sidelobes. In the following, the $3^{rd}$ harmonic template of a coded excitation transmit waveform is derived.

Let the Fourier transform of transmit waveform be $$H(j\omega) = \|H(j\omega)\| e^{ju(\omega)}$$

the Fourier transform of 3rd harmonic excited by this transmit waveform should be $$H_{3rdH}(j\omega) = H^3\left(j\frac{\omega}{3}\right) = \left\|H\left(j\frac{\omega}{3}\right)\right\|^3 e^{j3a\left(\frac{\omega}{3}\right)}$$

assuming that the 3rd harmonic is caused by the 3rd power term of the Taylor series of tissue non-linearity. Then the 3rd harmonic waveform is the Inverse Fourier transform. If this is used as a match filter template, there are never significant side lobes since the power spectrum has been changed. For this reason, the following Fourier transform is used to generate match filter templates.

$$\left\|H\left(j\frac{\omega}{3}\right)\right\| e^{j3a\left(\frac{\omega}{3}\right)}$$

Figure 27A:
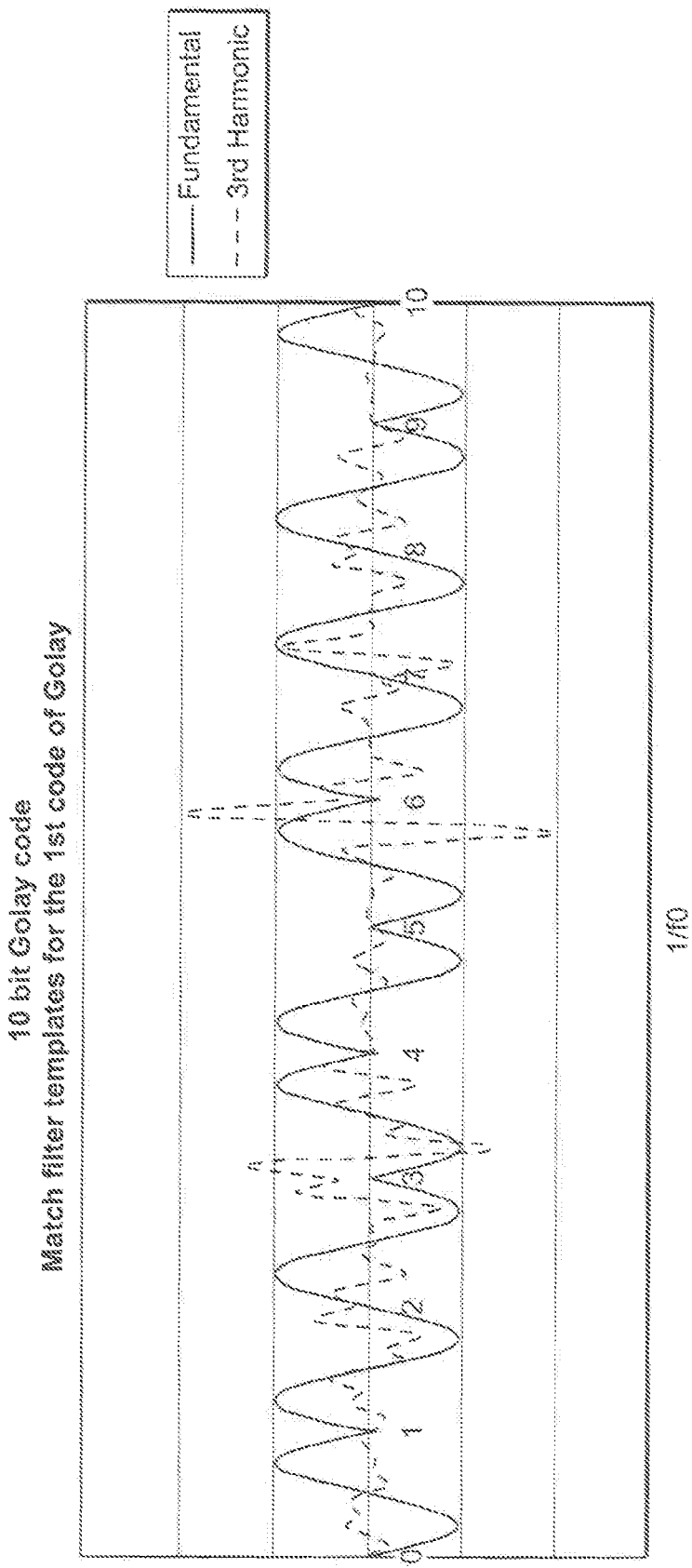
FIGS. 27A and 27B illustrate match filter template for first and second codes of Golay.
Figure 27B:
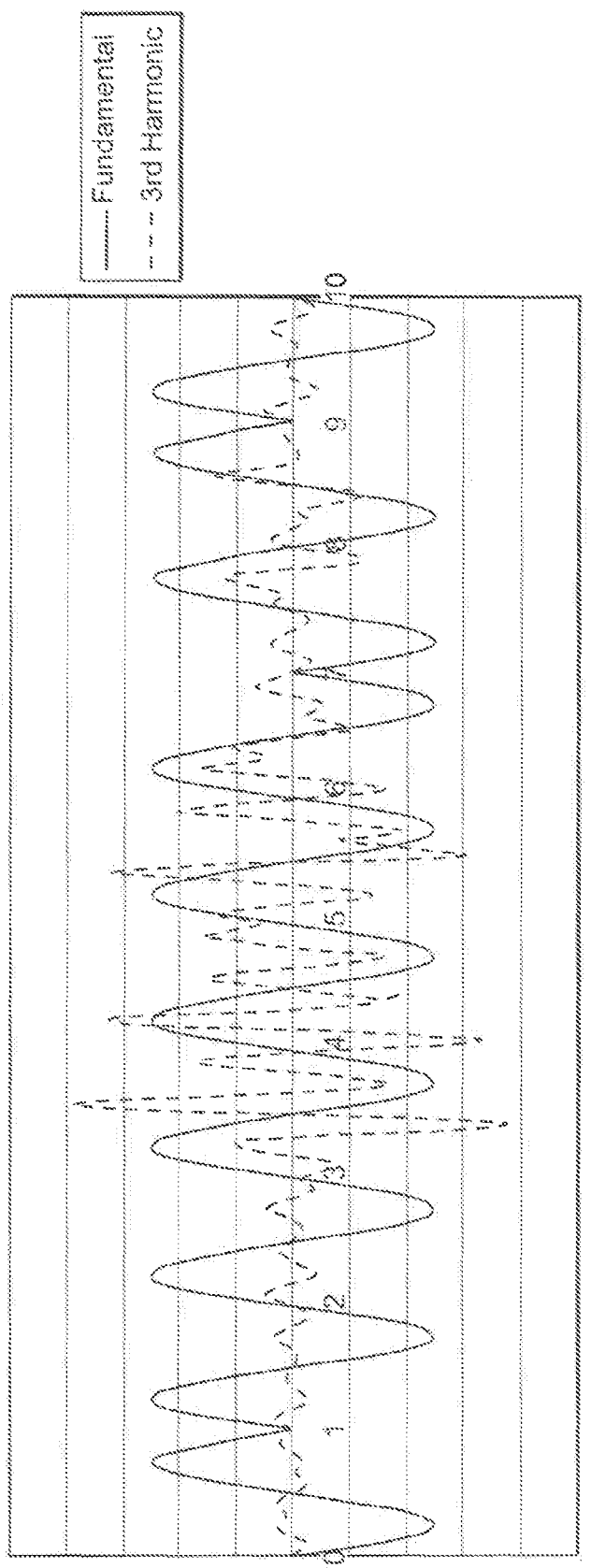
Figure 27C:
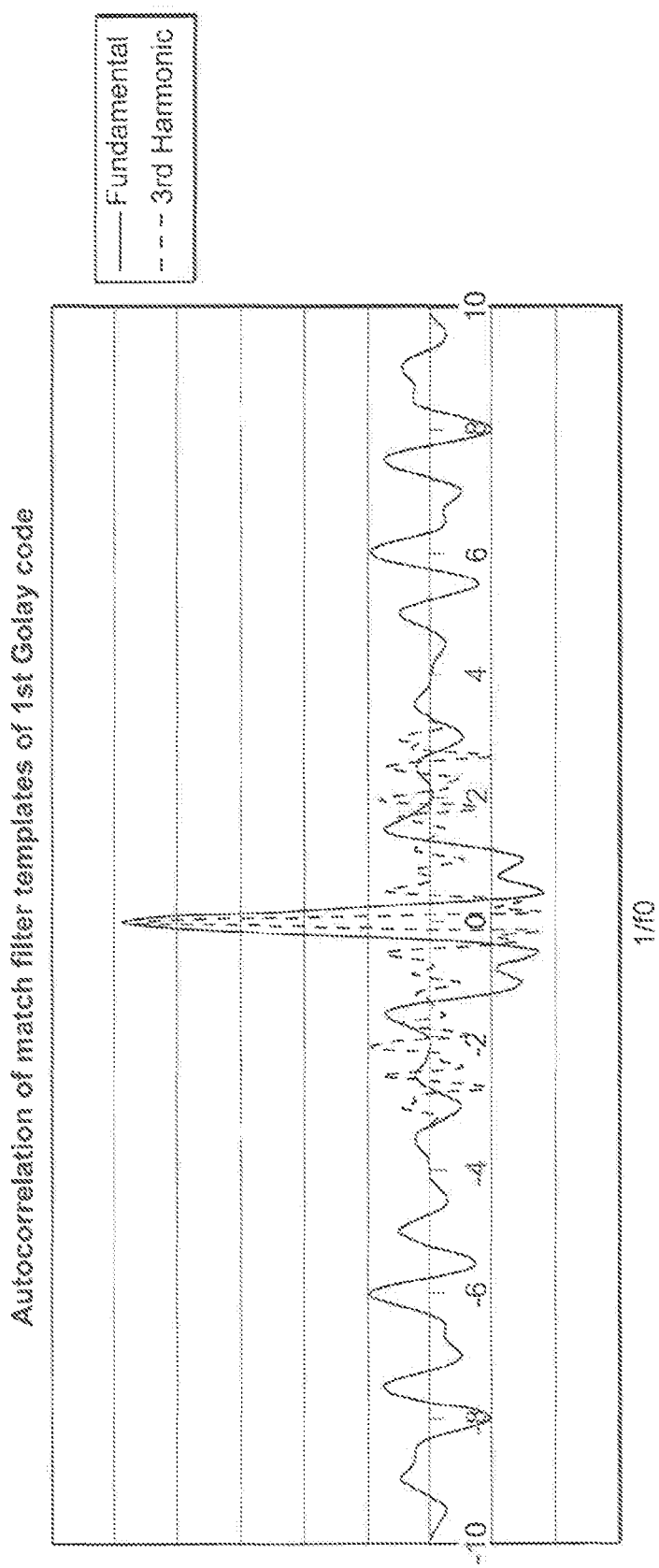
FIGS. 27C and 27D illustrate the autocorrelation of the fundamental and third harmonics for the filter template of the first and second Golay codes.
Figure 27D:
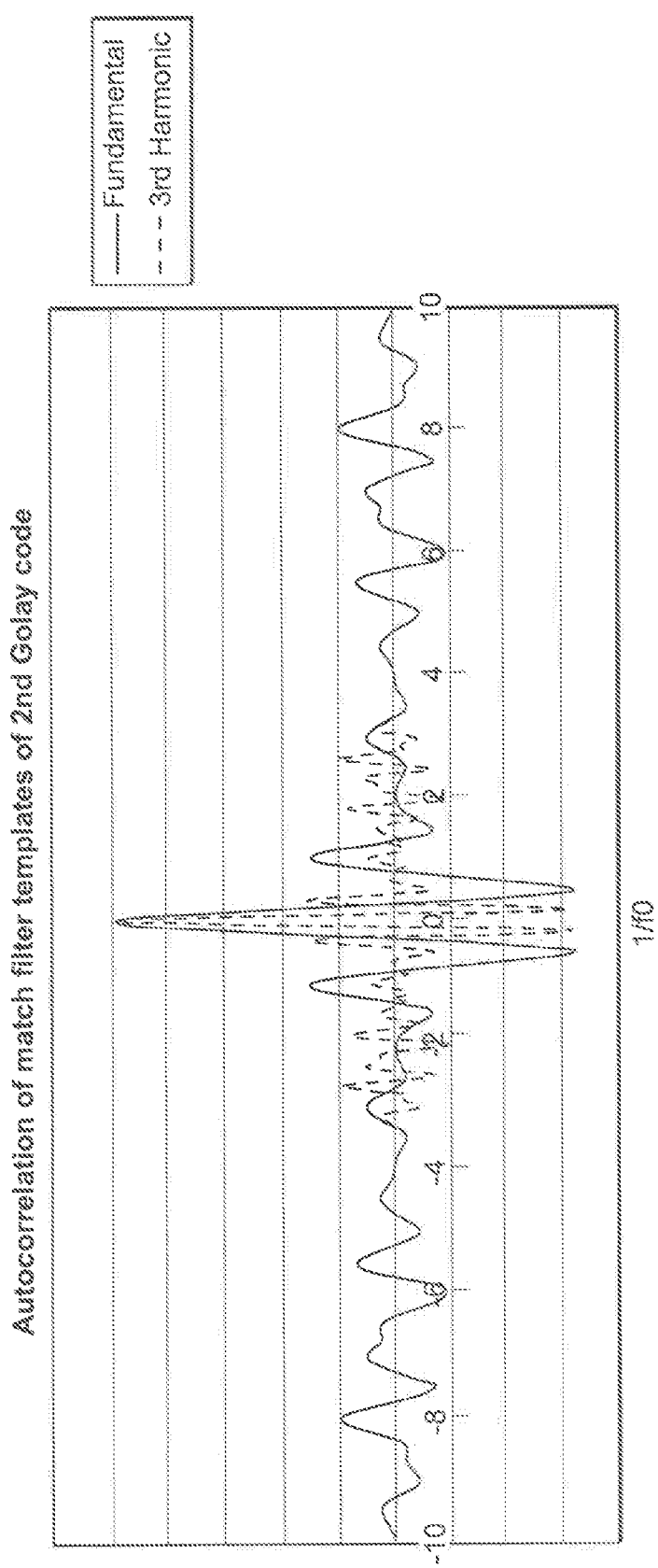
Figure 28:
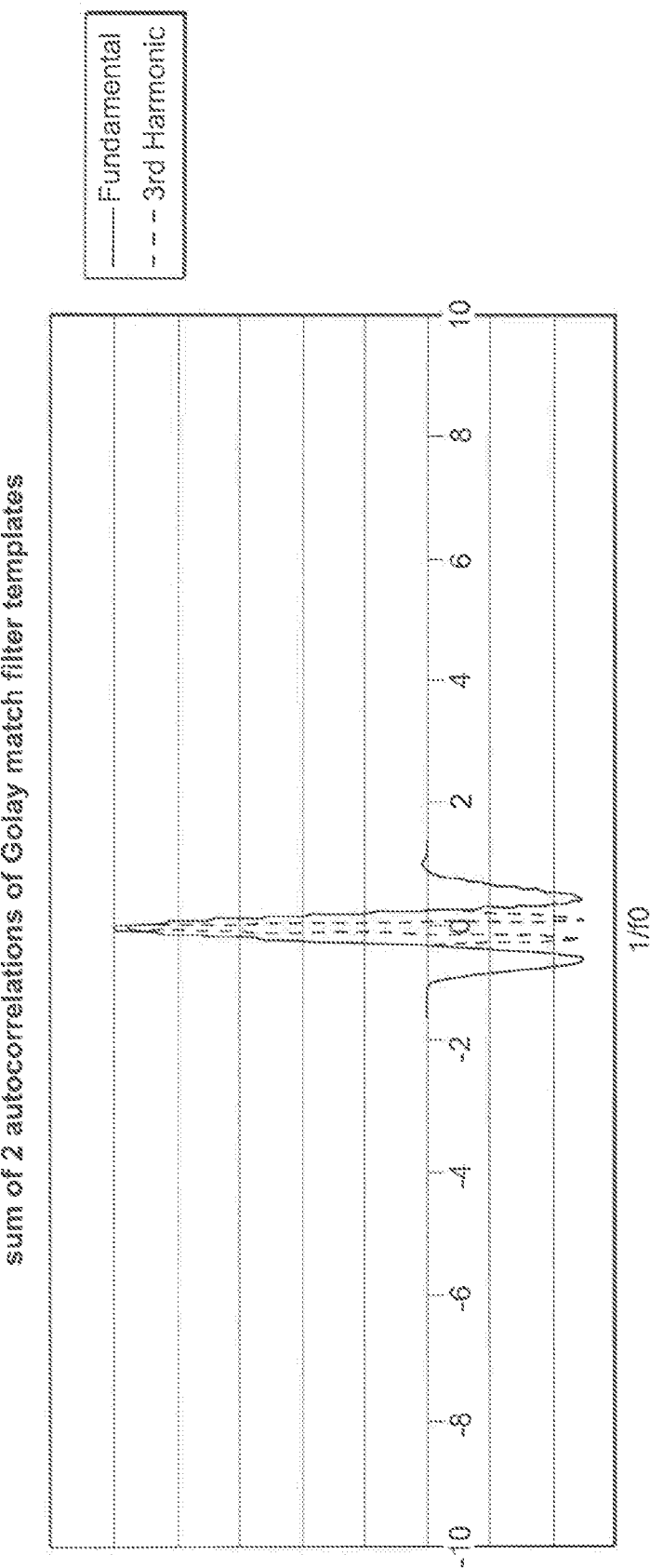
FIG. 28 shows the sum of the two autocorrelation shown in FIGS. 27C and 27D.

Based on the above derivation, the fundamental and $3^{rd}$ harmonic template of a 10-bit Colay code pair is shown in FIGS. 27A and 27B, where GCP1=[−1 1 1 −1 1 −1 1 1 1 −1], GCP2=[−1 1 1 1 1 1 1 −1 −1 1] The fundamental and $3^{rd}$ harmonic matched filter outputs, i.e. the autocorrelation of fundamental and $3^{rd}$ harmonic templates of the selected Golay pair is shown in FIGS. 27C and 27D, respectively. Finally, the same fundamental and third harmonic outputs of the two complementary codes are shown in FIG. 28. The $3^{rd}$ harmonic template of the first 10 bit Colay code is shown in FIG. 29A. A 12 times oversampling for fundamental and 4 times oversampling are used in deriving the code. The $3^{rd}$ harmonic template of the second 10 bit Colay code is shown in FIG. 29B. Again, a 12 times oversampling for fundamental and 4 times oversampling are used in deriving this code.

Figure 30C:
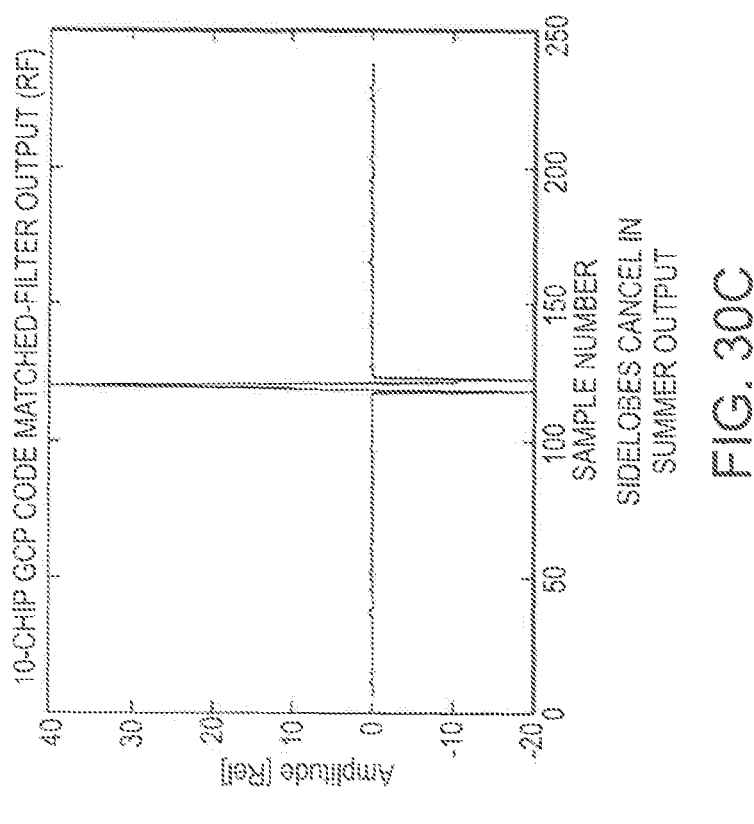
FIGS. 30A-30C illustrate sidelobe cancellation with the summed output.
Figure 30A:
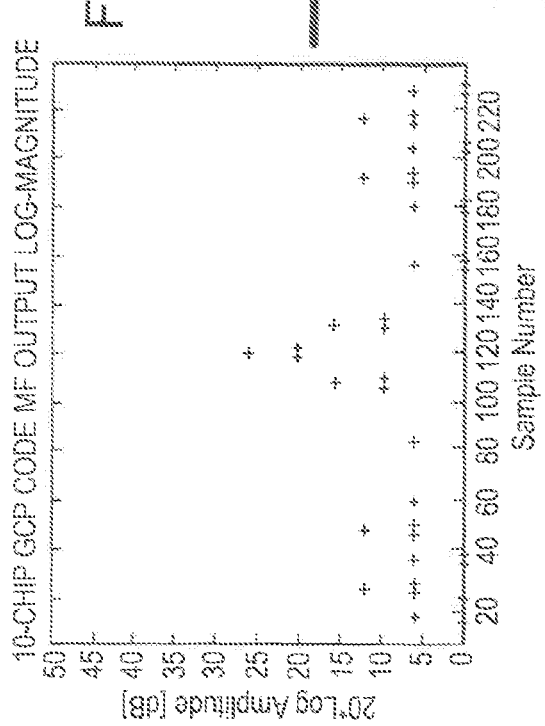
Figure 30B:
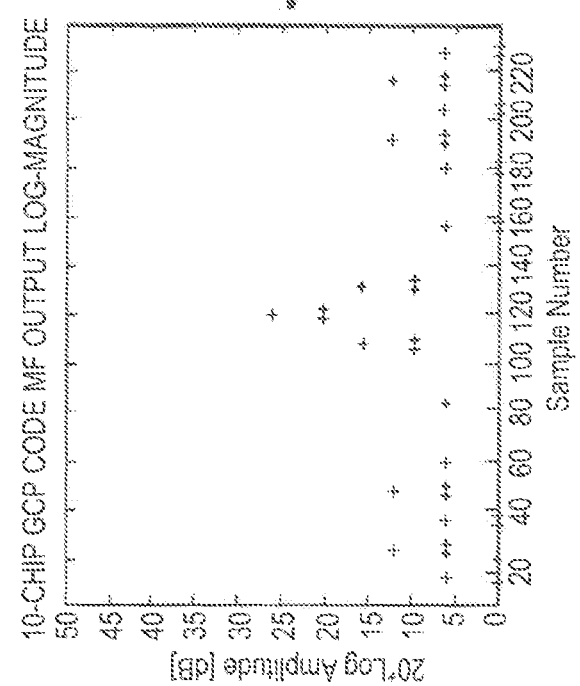

Another technique in selecting the $3^{rd}$ harmonic template is by inserting two zeros after each code word of the fundamental template. The third harmonic matched filter outputs, i.e. the autocorrelation of this alternative $3^{rd}$ harmonic template is shown in FIGS. 30A and 30B. It is demonstrated in FIG. 30C that there is no sidelobe of this matched filter output.

The claims should not be read as limited to the recited order or elements unless stated to that effect. All embodiments that come within the scope and spirit of the following claims and equivalents thereto are claimed as the invention.

The invention claimed is:

1. A medical ultrasound imaging method comprising:
   operating a transducer array having a one-dimensional array or two-dimensional array of transducer elements in a handheld probe housing wherein the transducer array detects signals in response to a controlled pulse transmission from the transducer array;
   processing the detected signals received by the transducer array with a first stage beamformer device in the handheld probe housing, the first stage beamformer device being operative in response to delay control signals from a control circuit in the handheld probe housing wherein the control circuit is connected to a system controller;
   further processing ultrasound data using a second stage beamformer device connected to the first stage beamformer device, the handheld probe housing communicating with an ultrasound processor housing that includes the system controller, a data processor, and a display that is operative in response to the system controller; and
   generating ultrasound image data with the data processor connected to the second stage beamformer device to display an ultrasound image on the display.

2. The method of claim 1 further comprising receiving the image data with the second stage beamformer device from the first stage beamformer device that includes a first plurality of subarray beamforming elements that are connected to the ultrasound processor housing with a cable.

3. The method of claim 1 further comprising operating the second stage beamformer device that includes a digital beamformer.

4. The method of claim 1 further comprising actuating the control circuit to control a transmission, by the transducer array, of a modified square wave with a suppressed third harmonic.

5. The method of claim 1 further comprising:
   configuring delays for the second stage beamformer device having a plurality of second beamformers to receive first beamformer image data from a first plurality of subarray beamformers; and
   operating the first plurality of subarray beamformers in parallel to provide image data.

6. The method of claim 1 further comprising configuring the one-dimensional array or two-dimensional array of transducer elements having subaperture arrays such that a region of interest is sequentially scanned by directing one or more beams in different directions.

7. The method of claim 1 further comprising using the transducer array elements that are connected with a flexible circuit having the first beamformer device mounted thereon.

8. The method of claim 1 further comprising operating the ultrasound processor housing having the system controller, the display, and the data processor weighing less than 15 lbs.

9. The method of claim 1 further comprising connecting the handheld probe housing having a plurality of flexible cables with a transducer subarray to a circuit board.

10. The method of claim 1 further comprising operating a plurality of circuit boards, having at least one of the first plurality of subarray beamformers, a memory that stores beamformer control data and a multiplexor circuit within the handheld probe housing.

11. The method of claim 1 further comprising operating a flexible circuit in the handheld probe housing.

12. The method of claim 11 further comprising configuring the flexible circuit having a flexible cable.

13. The method of claim 11 further comprising configuring the flexible circuit having a flexible printed circuit board.

14. The method of claim 1 further comprising associating a matched filter having a plurality of weights with stages of a delay line.

15. The method of claim 2 further comprising compressing each beam in the first plurality of subarray beamformers.

16. The method of claim 1 further comprising operating the second stage beamformer device with a plurality of digital beamformers.

17. The method of claim 1 further comprising operating the first plurality of subarray beamformers using a charge domain processor.

18. The method of claim 1 further comprising performing an ultrasound imaging procedure with a-scan conversion and Doppler processing of ultrasound signals with the data processor.

19. The method of claim 1 further comprising configuring the transducer array having a 128 element 1D subarray having eight adjacent elements.

20. The method of claim 19 further comprising connecting 128 connection input/output cables to connect the handheld probe housing to the ultrasound processor housing.

21. The method of claim 1 further comprising: integrating sixteen subarray processors having 8 programmable delays within the transducer probe; and connecting a front end integrated transducer probe to the ultrasound processor housing using 16 cables.

22. The method of claim 1 further comprising operating a low power transmit circuit, and a AC/DC converter within the handheld probe housing.

23. The method of claim 10 further comprising configuring the multiplexor circuit with a high voltage switch connecting a cable to a transmit element during a transmit period and to a receive element during a receive period.

24. The method of claim 10 further comprising amplifying a receive signal detected by the transducer array.

25. The method of claim 1 further comprising configuring a separate transmit element and a separate receive element.

26. The method of claim 25 further comprising operating the separate transmit element formed with a first transducer material and the separate receive element formed with a second transducer material.

27. A medical ultrasound imaging system comprising:
a transducer array having a one dimensional array or two dimensional array of transducer elements in a handheld probe housing wherein the transducer array detects signals in response to a controlled pulse transmission from the transducer array;
a first stage beamformer device in the handheld probe housing that processes the detected signals received by the transducer array, the first stage beamformer device being operative in response to delay control signals from a control circuit in the handheld probe housing wherein the control circuit is connected to a system controller;
a second stage beamformer device connected to the first stage beamformer device that processes ultrasound data, the handheld probe housing communicating with an ultrasound processor housing that includes the system controller, a data processor, and a display that is operative in response to the system controller to display ultrasound images; and
wherein the data processor is connected to the second stage beamformer device to process beamformed image data and display an ultrasound image on the display.

28. The system of claim 27 wherein image data is processed with the second stage beamformer device from the first stage beamformer device that includes a first plurality of subarray beamforming elements that are connected to the ultrasound processor housing with a cable and wherein the second stage beamformer device that includes a digital beamformer.

29. The system of claim 27 further comprising a low power transmit circuit, a high voltage switch integrated circuit and a AC/DC converter within the handheld probe housing wherein the one or two dimensional array of transducer elements having subaperture arrays such that a region of interest is sequentially scanned by directing one or more beams in different directions and wherein the ultrasound processor housing having the system controller, the display, and the data processor weighs less than 15 lbs.

30. The system of claim 27 wherein the first stage beamforming device comprises an integrated circuit.

31. The system of claim 27 wherein the second stage beamforming device comprises an integrated circuit.

32. The system of claim 27 wherein the control circuit and the first stage beamformer device are mounted on a circuit board in the handheld probe housing.

33. The system of claim 27 wherein the second stage beamformer device is within the ultrasound processor housing.

34. The system of claim 27 wherein the handheld probe housing further comprises a multiplexor that switches between subarray elements during an ultrasound imaging procedure.

* * * * *